United States Patent
Saltzman et al.

(10) Patent No.: US 11,814,464 B2
(45) Date of Patent: Nov. 14, 2023

(54) POLY(AMINE-CO-ESTER) POLYMERS AND POLYPLEXES WITH MODIFIED END GROUPS AND METHODS OF USE THEREOF

(71) Applicant: Yale University, New Haven, CT (US)

(72) Inventors: W. Mark Saltzman, New Haven, CT (US); Yuhang Jiang, New Haven, CT (US)

(73) Assignee: YALE UNIVERSITY, New Haven, CT (US)

( * ) Notice: Subject to any disclaimer, the term of this patent is extended or adjusted under 35 U.S.C. 154(b) by 620 days.

(21) Appl. No.: 16/862,491

(22) Filed: Apr. 29, 2020

(65) Prior Publication Data

US 2020/0399424 A1  Dec. 24, 2020

Related U.S. Application Data

(60) Provisional application No. 62/840,220, filed on Apr. 29, 2019.

(51) Int. Cl.
*C08G 63/685* (2006.01)
*A61K 47/59* (2017.01)

(52) U.S. Cl.
CPC .......... *C08G 63/685* (2013.01); *A61K 47/595* (2017.08)

(58) Field of Classification Search
CPC .......................... C08G 63/685; A61K 47/595
See application file for complete search history.

(56) References Cited

U.S. PATENT DOCUMENTS

| | | |
|---|---|---|
| 4,415,728 A | 11/1983 | Tremblay |
| 5,034,506 A | 7/1991 | Summerton |
| 5,142,047 A | 8/1992 | Summerton |
| 5,166,315 A | 11/1992 | Summerton |
| 5,217,866 A | 6/1993 | Summerton |
| 5,506,337 A | 4/1996 | Summerton |
| 5,521,063 A | 5/1996 | Summerton |
| 5,527,675 A | 6/1996 | Coull |
| 5,539,082 A | 7/1996 | Nielsen |
| 5,623,049 A | 4/1997 | Lobberding |
| 5,698,546 A | 12/1997 | Bridger |
| 5,698,685 A | 12/1997 | Summerton |
| 5,714,331 A | 2/1998 | Buchardt |
| 5,736,336 A | 4/1998 | Buchardt |
| 5,773,571 A | 6/1998 | Nielsen |
| 5,786,571 A | 7/1998 | Bethel |
| 6,849,272 B1 | 2/2005 | Langer |
| 9,272,043 B2 | 3/2016 | Saltzman |
| 2004/0242831 A1 | 12/2004 | Tian |
| 2008/0166382 A1 | 7/2008 | Hsieh |
| 2011/0008451 A1 | 1/2011 | Saltzman |
| 2014/0342003 A1 | 11/2014 | Saltzman |
| 2015/0073041 A1 | 3/2015 | Saltzman |
| 2016/0251477 A1 | 9/2016 | Cui |
| 2017/0121454 A1 | 5/2017 | Saltzman |
| 2020/0399424 A1 | 12/2020 | Saltzman |

FOREIGN PATENT DOCUMENTS

| | | |
|---|---|---|
| FR | 2873570 | 2/2006 |
| IN | 20130205613 | 6/2014 |
| WO | 1993/012096 | 6/1993 |
| WO | 1993012096 | 6/1993 |
| WO | 2002/010142 | 2/2002 |
| WO | 2002010142 | 2/2002 |
| WO | 02/44321 | 6/2002 |
| WO | 0244321 | 6/2002 |
| WO | 2004073617 | 9/2004 |
| WO | 2013/082529 | 6/2013 |
| WO | 2013082529 | 6/2013 |
| WO | 2017/151623 | 9/2017 |
| WO | 2017151623 | 9/2017 |
| WO | 2017/197128 | 11/2017 |
| WO | 2017197128 | 11/2017 |
| WO | 2020033951 | 2/2020 |

OTHER PUBLICATIONS

Adams, et al., "miR-34a Silences c-SRC to Attenuate Tumor Growth in Triple Negative Breast Cancer", *Cancer Res.*, 76(4): 927-939 (2016).
Akinc, et al., "Synthesis of poly (beta-amino ester)s optimized for highly effective gene delivery", *Bioconj. Chem.*, 14(5): 979-988 (2003).
Al-Dosari, et al., "Nonviral gene delivery: principle, limitations, and recent progress", *AAPS J.*, 11(4):671-681 (2009).
Bernstein, et al., "Role for a bidentate ribonuclease in the initiation step of RNA interference", *Nature*, 409(6818):363-6 (2001).
Braasch, et al., "Locked nucleic acid (LNA): fine-tuning the recognition of DNA and RNA", *Chem. Biol.*, 8(1):1-7 (2001).
Carter, "Introduction to current and future protein therapeutics: a protein engineering perspective", *Exp. Cell Res.*, 317(9): 1261-1269 (2011).
Chamberlin, et al., "New RNA polymerase from *Escherichia coli* infected with bacteriophage T7", *Nature*, 228(5268):227-231 (1970).
Chen, et al. "Targeted nanoparticles deliver siRNA to melanoma", *J. Invest. Dermatol.*, 130(12):2790-2798 (2010).

(Continued)

*Primary Examiner* — Michael P Cohen
(74) *Attorney, Agent, or Firm* — PABST PATENT GROUP LLP

(57) ABSTRACT

Poly(amine-co-ester) polymers, methods of forming active agent-load polyplexes and particles therefrom, and methods of using them for delivery of nucleic acid agents with optimal uptake have been developed. Examples demonstrate critical molecular weights in combination with exposed carboxylic and/or hydroxyl groups, and methods of making. Typically, the compositions are less toxic, more efficient at drug delivery, or a combination thereof compared to a control other transfection reagents. In some embodiments, the compositions are suitable for in vivo delivery, and can be administered systemically to a subject to treat a disease or condition.

27 Claims, 15 Drawing Sheets

Specification includes a Sequence Listing.

(56) References Cited

OTHER PUBLICATIONS

Choosakoonkriang, et al., "Biophysical characterization of PEI/DNA complexes", *J. Pharmaceut. Sci.*, 92(8): 1710-1722 (2003).
Cui, et al., "Ex vivo pretreatment of human vessels with siRNA nanoparticles provides protein silencing in endothelial cells", *Nat. Commun.*, 8(1):191 (2017).
Davanloo, et al., "Cloning and expression of the gene for bacteriophage T7 RNA polymerase", *PNAS*, 81(7):2035-39 (1984).
Efremenko, et al., "A simple and highly effective catalytic nanozyme scavenger for organophosphorus neurotoxins", *J. Control Release*, 247:175-181 (2017).
Elbashir, et al., "RNA interference is mediated by 21and 22-nucleotide RNAs", *Genes Dev.*, 15(2):188-200 (2001a).
Elbashir, et al., "Duplexes of 21±nucleotide RNAs mediate RNA interference in cultured mammalian cells", *Nature*, 411(6836):494 498 (2001b).
Felgner, et al., "Enhanced gene delivery and mechanism studies with a novel series of cationic lipid formulations", *J. Biol. Chem.*, 269(4):2550-2561 (1994).
Felgner, et al., "Lipofection: a highly efficient, lipid-mediated DNA transfection Procedure", *PNAS*, 84(21):7413-7417 (1987).
Fire, et al., "Potent and specific genetic interference by double-stranded RNA in Caenorhabditis elegans", *Nature*, 391(6669):806-11 (1998).
Gao, et al., "The association of autophagy with polyethylenimine-induced cytotoxicity in nephritic and hepatic cell lines", *Biomaterials*, 32(33):8613-8625 (2011).
Hammond, et al., "Hammond SM, Bernstein E, Beach D, Hannon GJAn RNA-directed nuclease mediates post-transcriptional gene silencing in Drosophila cells. Nature 404: 293-296", *Nature*, 404(6775):293-6 (2000).
Hannon, "RNA interference", *Nature*, 418(6894):244-51 (2002).
Harris, et al., "Nano-particle delivery of brain derived neurotrophic factor after focal cerebral ischemia reduces tissue injury and enhances behavioral recovery", *Pharmacol. Biochem. Behav.*, 150-151:48-56 (2016).
Harris, et al., "Tissue-specific gene delivery via nanoparticle coating", *Biomaterials*, 31(5):998-1006 (2010).
Jiang, et al., "Nanoformulation of Brain-Derived Neurotrophic Factor with Target Receptor-Triggered-Release in the Central Nervous System", *Adv. Funct. Mater.*, 28(6):1703982, 24 pages (2018).
Jiang, et al., "SOD1 nanozyme salvages ischemic brain by locally protecting cerebral vasculature", *J. Control Release*, 213:36-44 (2015).
Jiang, et al., "SOD1 nanozyme with reduced toxicity and MPS accumulation", *J. Control Release*, 231:38-49 (2016).
Jiang, "Lipase-catalyzed synthesis of poly(amine-co-esters) via copolymerization of diester with amino-substituted diol.", *Biomacromolecules*, 11(4):1089-1093 (2010).
Johnston, et al., "Regulated Expression of Erythropoietin from an AAV Vector Safely Improves the Anemia of b-Thalassemia in a Mouse Model", *Mol. Ther.*, 7(4):493-497 (2003).
Kafil, et al., "Cytotoxic Impacts of Linear and Branched Polyethylenimine Nanostructures in A431 Cells", *BioImpacts*, 1(1):23-30 (2011).
Kariko, et al., "Increased erythropoiesis in mice injected with submicrogram quantities of pseudouridine-containing mRNA encoding erythropoietin", *Mol. Ther.*, 20(5): 948-953 (2012).
Kauffman, et al., "Optimization of Lipid Nanoparticle Formulations for mRNA Delivery in Vivo with Fractional Factorial and Definitive Screening Designs", *Nano Lett.*, 15(11): 7300-7306 (2015).
Liu, et al., "Nonviral gene delivery: What we know and what is next", *AAPS J.*, 9(1): E92-E104 (2007).
Liu, et al., "Enzyme-synthesized poly(amine-co-esters) as 30 nonviral vectors for gene delivery", *J. Biomed. Mater. Res. A*, 96(2):456-465 (2011).
Liu, et al., "Hydrodynamics-based transfection in animals by systemic administration of plasmid DNA", *Gene Ther.*, 6(7):1258-1266 (1999).
Lv, et al., "Toxicity of cationic lipids and cationic polymers in gene delivery", *J. Contr. Rel.*, 114(1): 100-109 (2006).
Martinez, et al., "Single-stranded antisense siRNAs guide target RNA cleavage in RNAi", *Cell*, 110(5):563-74 (2002).
Nagayama, et al., "Time-dependent changes in opsonin amount associated on nanoparticles alter their hepatic uptake characteristics", *Int. J. Pharm.*, 342:215-21 (2007).
Napoli, et al., "Introduction of a Chimeric Chalcone Synthase Gene into Petunia Results in Reversible Co-Suppression of Homologous Genes in trans", *Plant Cell*, 2(4):279-89 (1990).
Natarajan, et al., "Nanoformulated copper/zinc superoxide dismutase exerts differential effects on glucose vs lipid homeostasis depending on the diet composition possibly via altered AMPK signaling", *Transl. Res.*, 188:10-26 (2017).
Nicol, et al., "Poly-L-glutamate, an anionic polymer, enhances transgene expression for plasmids delivered by intramuscular injection with in vivo electroporation", *Gene. Ther.*, 9(20): 1351-1358 (2002).
Nykanen, et al., "ATP requirements and small interfering RNA structure in the RNA interference pathway", *Cell*, 107(3):309-21 (2001).
Schaffer, et al., "Vector unpacking as a potential barrier for receptor-mediated polyplex gene delivery", *Biotechnol. Bioeng.*, 67(5):598-606 (2000).
Schlegel, et al., "Anionic polymers for decreased toxicity and enhanced in vivo delivery of siRNA complexed with cationic liposomes", *J. Contr. Rel.*, 152:393-401 (2011).
Stirchak, et al., "Uncharged stereoregular nucleic acid analogs. 1. Synthesis of a cytosine-containing oligomer with carbamate internucleoside linkages", *Organic Chem.*, 52(19):4202-4206 (1987).
Suk, et al., "Gene delivery to differentiated neurotypic cells with RGD and HIV Tat peptide functionalized polymeric nanoparticles", *Biomaterials*, 27(29):5143-5150 (2006).
Sunshine, et al., "Uptake and transfection with polymeric nanoparticles are dependent on polymer end-group structure, but largely independent of nanoparticle physical and chemical properties", *Mol. Pharm.*, 9(11):3375-3383 (2012).
Sunshine, et al., "Effects of Base Polymer Hydrophobicity and End Group Modification on Polymeric Gene Delivery", *Biomacromolecules*, 12(10): 3592-3600 (2011).
Templeton, et al., "Improved DNA: liposome complexes for increased systemic delivery and gene expression", *Nat. Biotechnol.*, 15(7):647-652 (1997).
Tros De Ilarduya, et al., "Gene delivery by lipoplexes and polyplexes", *Eur. J. Pharm. Sci.*, 40(3):159-170 (2010).
Tsuchida, et al., "The rôle of the chain length in the stability of polyion complexes", *Makromol. Chem.*, 175(2):593-601 (1974).
Ui-Tei, et al., "Sensitive assay of RNA interference in Drosophila and Chinese hamster cultured cells using firefly luciferase gene as target", *FEBS Lett*, 479(3):79-82 (2000).
Villeval, et al., "Retrovirus-mediated transfer of the erythropoietin gene in hematopoietic cells improves the erythrocyte phenotype in murine beta-thalassemia", *Blood*, 84(3): 928-933 (1994).
Wang, et al., "Synthesis and characterization of cationic micelles self-assembled from a biodegradable copolymer for gene delivery", *Biomacromolecules*, 8(3):1028-1037 (2007a).
Wang, et al., "The self-assembly of biodegradable cationic polymer micelles as vectors for gene transfection", *Biomaterials*, 28:5358-5368 (2007b).
Weising, et al., "Foreign genes in plants: transfer, structure, expression, and applications", *Ann. Rev. Genetics*, 22:421-77 (1988).
Weissman, "mRNA transcript therapy", *Expert Rev. Vaccines*, 14(2): 265-281 (2015).
Zhang, et al., "Galactosylated ternary DNA/polyphosphoramidate nanoparticles mediate high gene transfection efficiency in hepatocytes", *J. Controlled Release*, 102(3):749-63 (2005).
Zhou, et al., "Biodegradable poly(amine-co-ester) terpolymers for targeted gene delivery", *Nature Materials*, 11(1):82-90 (2012).
Chen, et al., "Novel pH-sensitive cationic lipids with linear ortho ester linkers for gene delivery", European Journal of Medicinal Chemistry, 52:159-172 (2012).
Ciuclan, et al., "Imatinib Attenuates Hypoxia-induced Pulmonary Arterial Hypertension Pathology via Reduction in 5-Hydroxytraptamine

(56) References Cited

OTHER PUBLICATIONS through Inhibition of Tryptophan Hydroxylase 1 Expression," Am. Thoracic Society; American journal of respiratory and critical care medicine, 187(1):78-89 (2013).
Izikki, et al., "Endothelial-derived FGF2 contributes to the progression of pulmonary hypertension in humans and rodents", Journal of Clinical Investigation, 119(3):512-523 (2009).
Jiang, et al., "A 'top-down' approach to actuate poly(amine-co-ester) terpolymers for potent and safe mRNA delivery", Biomaterials, 176:122-130 (2018).
Jiang, et al., "Quantitating Endosomal Escape of a Library of Polymers for mRNA Delivery", Nano Letters, 20(2):1117-1123 (2020).
Jin, et al., "Current Progress in Gene Delivery Methods and Nano-carriers", Theranostics, 4(3):240-255 (2014).
Kanaan, et al., "Use of multitarget tyrosine kinase inhibitors to attenuate platelet-derived growth factor signalling in lung disease", Eur Respir Rev; 26: 170061 (2017).
Kauffman, et al., "Tunability of Biodegradable Poly(amine-co-ester) Polymers for Customized Nucleic Acid Delivery and Other Biomedical Applications", Biomacromolecules, 19(9): 3861-3873 (2018).
Kormann, et al. "Expression of therapeutic proteins after delivery of chemically modified mRNA in mice", Nature Biotechnology, 29(2):154-157 (2011).
Liu, et al., "Internal stimuli-responsive nanocarriers for drug delivery: Design strategies and applications", Materials Science and Engineering C Mater. Biol. Appl., 71:1267-1280 (2017).
Liu, et al., "Poly(omega-pentadecalactone-co-butylene-co-succinate) nanoparticles as biodegradable carriers for camptothecin delivery", Biomaterials, 30(29): 5707-5719 (2009).
Luten, et al., "Biodegradable polymers as non-viral carriers for plasmid DNA delivery", J Cont. Rel., 126:97-100 (2008).
Pala, et al., "Nanoparticle-Mediated Drug Delivery for the Treatment of Cardiovascular Diseases", Int. J. Nanomedicine, 15:3741-3769 (2020).
Raudszus, et al., "A new preparation strategy for surface modified PLA nanoparticles to enhance uptake by endothelial cells", Int. J. Pharm., 536(1):211-221 (2018).
Tehrani-Bagha, et al., "Cleavable surfactants", Current Opinion in Colloid and Interface Science, 12(2):81-91 (2007).
Wei, et al., "Biodegradablepoly(-caprolactone)—poly(ethyleneglycol)copolymers asdrugdeliverysystem", International J. of Pharm., 381:1-18 (2009).
Zhang, et al. "Multifunctional Poly(amine-co-ester-co-ortho-ester) for efficient and safe gene delivery", ACS Biomaterials Science and Engineering, 2:2080-2089 (2016).
Zhang, et al., "(491a) Biodegradable, multifunctional Poly(amine-co-ester) with ortho ester in the main chain for the delivery of plasmid DNA and siRNA", AICHE comference proceedings 2014 annual meeting.
Zhang, et al., "Functional lipids and lipoplexes for improved gene delivery", Biochemie, 94(1):42-58 (2012).
Zhang, et al., "Micelles of enzymatically synthesized PEG-poly(amine-co-ester) block copolymers as pH-responsive nanocarriers for docetaxel delivery", Colloids and Surfaces B: Biointerfaces, 115:349-358 (2014b).
Zhong et al., "A versatile family of degradable non-viral gene carriers based on hyperbranched poly( ester amine )s", Journal of Controlled Release, 109:317-329 (2005).
Zhou, et al., "Biodegradable poly(amine-co-ester) terpolymers for targeted gene delivery", Nat Mater., 11(1):82-90 (2012).

POLY(AMINE-CO-ESTER) POLYMERS AND POLYPLEXES WITH MODIFIED END GROUPS AND METHODS OF USE THEREOF

STATEMENT REGARDING FEDERALLY SPONSORED RESEARCH OR DEVELOPMENT

This invention was made with government support under HD090503 and HL147352 awarded by National Institutes of Health. The government has certain rights in the invention.

REFERENCE TO SEQUENCE LISTING

The Sequence Listing submitted as a text file named "YU_7706_ST25.txt," created on Sep. 10, 2020, and having a size of 3,123 bytes is hereby incorporated by reference pursuant to 37 C.F.R. § 1.52(e)(5).

FIELD OF THE INVENTION

The field of the invention is generally related to polymer compositions and methods for improved systemic delivery of diagnostic, prophylactic and/or therapeutic agents, particularly nucleic acid-based agents, in vitro and in vivo.

BACKGROUND OF THE INVENTION

Non-viral vectors for gene delivery have attracted much attention in the past several decades due to their potential for limited immunogenicity, ability to accommodate and deliver large size genetic materials, and potential for modification of their surface structures. Major categories of non-viral vectors include cationic lipids and cationic polymers. Cationic lipid-derived vectors, which were pioneered by Feigner and colleagues, represent some of the most extensively investigated systems for non-viral gene delivery (Feigner, et al. Lipofection: a highly efficient, lipid-mediated DNA-transfection procedure. *PNAS,* 84, 7413-7417 (1987)) (Templeton, et al. Improved DNA: liposome complexes for increased systemic delivery and gene expression. *Nat. Biotechnol.* 15, 647-652 (1997)) (Chen, et al. Targeted nanoparticles deliver siRNA to melanoma. *J. Invest. Dermatol.* 130, 2790-2798 (2010)).

Cationic polymer non-viral vectors have gained increasing attention because of flexibility in their synthesis and structural modifications for specific biomedical applications. Both cationic lipid and cationic polymer systems deliver genes by forming condensed complexes with negatively charged DNA through electrostatic interactions: complex formation protects DNA from degradation and facilitates its cellular uptake and intracellular traffic into the nucleus.

Polyplexes formed between cationic polymers and DNA are generally more stable than lipoplexes formed between cationic lipids and DNA, but both are often unstable in physiological fluids, which contain serum components and salts, and tend to cause the complexes to break apart or aggregate (Al-Dosari, et al. Nonviral gene delivery: principle, limitations, and recent progress. *AAPS J.* 11, 671-681 (2009)) (Tros de Ilarduya, et al. Gene delivery by lipoplexes and polyplexes. *Eur. J. Pharm. Sci.* 40, 159-170 (2010)). Additionally, although some work indicates that anionic polymers or even naked DNA can provide some level of transfection under certain conditions, transfection by both lipids and polymers usually requires materials with excess charge, resulting in polyplexes or lipoplexes with net positive charges on the surface (Nicol, et al. Poly-L-glutamate, an anionic polymer, enhances transgene expression for plasmids delivered by intramuscular injection with in vivo electroporation. *Gene. Ther.* 9, 1351-1358 (2002)) (Schlegel, et al. Anionic polymers for decreased toxicity and enhanced in vivo delivery of siRNA complexed with cationic liposomes. *J. Contr. Rel.* 152, 393-401 (2011)) (Liu, et al, Nonviral gene delivery: What we know and what is next. *AAPS J.* 9, E92-E104 (2007)) (Liu, et al. Hydrodynamics-based transfection in animals by systemic administration of plasmid DNA. *Gene Ther.* 6, 1258-1266 (1999)). When injected into the circulatory system in vivo, the positive surface charge initiates rapid formation of complex aggregates with negatively charged serum molecules or membranes of cellular components, which are then cleared by the reticuloendothelial system (RES).

More importantly, many cationic vectors developed so far exhibit substantial toxicity, which has limited their clinical applicability (Tros de Ilarduya, et al. Gene delivery by lipoplexes and polyplexes. *Eur. J. Pharm. Sci.* 40, 159-170 (2010)) (Gao, et al. The association of autophagy with polyethylenimine-induced cytotoxicity in nephritic and hepatic cell lines. *Biomaterials* 32, 8613-8625 (2011)) (Feigner, et al. Enhanced gene delivery and mechanism studies with a novel series of cationic lipid formulations. *J. Biol. Chem.* 269, 2550-2561 (1994)) (Kafil, et al. Cytotoxic Impacts of Linear and Branched Polyethylenimine Nano-structures in A431 Cells. *BioImpacts* 1, 23-30 (2011)) (Lv, et al. Toxicity of cationic lipids and cationic polymers in gene delivery. *J Contr. Rel.* 114, 100-109 (2006)). This too appears to depend on charge: excess positive charges on the surface of the complexes can interact with cellular components, such as cell membranes, and inhibit normal cellular processes, such as clathrin-mediated endocytosis, activity of ion channels, membrane receptors, and enzymes or cell survival signaling (Gao, et al. The association of autophagy with polyethylenimine-induced cytotoxicity in nephritic and hepatic cell lines. *Biomaterials* 32, 8613-8625 (2011)) (Feigner, et al Enhanced gene delivery and mechanism studies with a novel series of cationic lipid formulations. *J. Biol. Chem.* 269, 2550-2561 (1994)) (Kafil, et al. Cytotoxic Impacts of Linear and Branched Polyethylenimine Nano-structures in A431 Cells. *BioImpacts* 1, 23-30 (2011)).

As a result, cationic lipids often cause acute inflammatory responses in animals and humans, whereas cationic polymers, such as PEI, destabilize the plasma-membrane of red blood cells and induce cell necrosis, apoptosis and autophagy (Tros de Ilarduya, et al. Gene delivery by lipoplexes and polyplexes. *Eur. J. Pharm. Sci.* 40, 159-170 (2010)) (Gao, et al. The association of autophagy with polyethylenimine-induced cytotoxicity in nephritic and hepatic cell lines. *Biomaterials* 32, 8613-8625 (2011)) (Lv, et al. Toxicity of cationic lipids and cationic polymers in gene delivery. *J. Contr. Rel.* 114, 100-109 (2006)). Because of these undesirable effects, there is a need for highly efficient non-viral vectors that have lower charge densities.

Synthesis of a family of biodegradable poly(amine-co-esters) formed via enzymatic copolymerization of diesters with amino-substituted diols is discussed in Liu, et al. Enzyme-synthesized poly(amine-co-esters) as nonviral vectors for gene delivery. *J. Biomed. Mater. Res. A* 96A, 456-465 (2011) and Jiang, Z. Lipase-catalyzed synthesis of poly(amine-co-esters) via copolymerization of diester with amino-substituted diol. *Biomacromolecules* 11, 1089-1093 (2010).

Diesters with various chain length (e.g., from succinate to dodecanedioate) were copolymerized with diethanolamines with either an alkyl (methyl, ethyl, n-butyl, t-butyl) or an aryl (phenyl) substituent on the nitrogen. The high tolerance of the lipase catalyst allowed the copolymerization reactions to complete in one step without protection and deprotection of the amino functional groups. Upon protonation at slightly acidic conditions, these poly(amine-co-esters) readily condense DNA and form nano-sized polyplexes. Screening studies revealed that one of these materials, poly(N-methyldiethyleneamine sebacate) (PMSC), transfected a variety of cells including HEK293, U87-MG, and 9L, with efficiency comparable to that of leading commercial products, such as Lipofectamine 2000 and PEI14. PMSC had been previously used for gene delivery, but the delivery efficiency of the enzymatically synthesized materials was approximately five orders of magnitude higher than any previously reported (Wang, et al. Synthesis and characterization of cationic micelles self-assembled from a biodegradable copolymer for gene delivery. *Biomacromolecules* 8, 1028-1037 (2007)) (Wang, et al. The self-assembly of biodegradable cationic polymer micelles as vectors for gene transfection. *Biomaterials* 28, 5358-5368 (2007)). However, these poly (amine-co-esters) were not effective for systemic delivery of nucleic acids in vivo. This may be due to the fact that the polyplexes formed by these polymers and genetic materials (1) do not have sufficient efficiency for in vivo applications and/or (2) are not stable enough in the blood and fall apart or aggregate during circulation.

Accordingly, there remains a need for non-viral vectors suitable for efficient systemic, in vivo or in vitro delivery of nucleic acids with high transfection efficiency and low toxicity.

There is also a need for polymeric nanocarriers in which the molecular weight, polymer composition, and/or end groups can be easily controlled and modified.

Therefore, it is an object of the invention to provide improved polymers which can effectively deliver therapeutic, diagnostic, and/or prophylactic agents, especially nucleic acids, in vivo or in vitro, and methods of making and using thereof.

It is an object of the invention to provide improved polymers which can effectively deliver genetic materials to cells in high efficiency in vitro and are suitable for in vivo delivery of nucleic acids, and methods of making thereof.

It is also an object of the invention to provide methods of using improved polymers for systemic delivery of nucleic acids in vivo.

SUMMARY OF THE INVENTION

Polymers with improved properties for delivering therapeutic, diagnostic, and/or prophylactic agents are described. Preferably, the agents are nucleic acid-based agents. In preferred embodiments, the polymers and polyplexes and particles formed therefrom, show improved loading, improved cellular transfection, improved intracellular endosomal release, or a combination thereof of a nucleic acid cargo, such as RNA, more particularly mRNA. Poly(amine-co-ester) polymers, methods of forming active agent-load polyplexes and particles therefrom, and methods of using them for delivery of nucleic acid agents with optimal uptake have been developed. Examples demonstrate critical molecular weights in combination with exposed carboxylic and/or hydroxyl groups, and methods of making. Typically, the compositions are less toxic, more efficient at drug delivery, or a combination thereof compared to a control other transfection reagents. In some embodiments, the compositions are suitable for in vivo delivery, and can be administered systemically to a subject to treat a disease or condition.

Polymers having a structure of Formula I are disclosed.

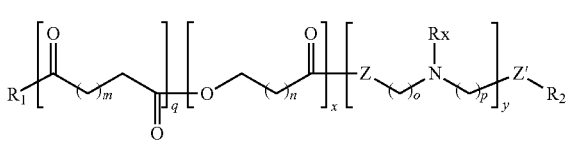

Formula I wherein n is an integer from 1-30,
m, o, and p are independently integers from 1-20,
x, y, and q are independently integers from 1-1000,
$R_x$ is hydrogen, substituted or unsubstituted alkyl, or substituted or unsubstituted aryl, or substituted or unsubstituted alkoxy,
Z and Z' are independently O or NR', wherein R' is hydrogen, substituted or unsubstituted alkyl, or substituted or unsubstituted aryl,
$R_1$ and $R_2$ are chemical entities containing a hydroxyl group, a primary amine group, a secondary amine group, a tertiary amine group, or combinations thereof.
In some forms, Z is the same as Z'.
In some forms, Z is O and Z' is O. In some forms, Z is NR' and Z' is NR'. In some forms, Z is O and Z' is NR'. In some forms, Z is NR' and Z' is O.
In some forms, Z' is O and n is an integer from 1-24, such as 4, 10, 13, or 14. In some forms, Z is also O.
In some forms, Z' is O, n is an integer from 1-24, such as 4, 10, 13, or 14, and m is an integer from 1-10, such as 4, 5, 6, 7, or 8. In some forms, Z is also O.
In some forms, Z' is O, n is an integer from 1-24, such as 4, 10, 13, or 14, m is an integer from 1-10, such as 4, 5, 6, 7, or 8, and o and p are the same integer from 1-6, such 2, 3, or 4. In some forms, Z is also O.
In some embodiments, Z' is O, n is an integer from 1-24, such as 4, 10, 13, or 14, m is an integer from 1-10, such as 4, 5, 6, 7, or 8, and R is alkyl, such a methyl, ethyl, n-propyl, isopropyl, n-butyl, t-butyl, isobutyl, sec-butyl, cyclohexyl, (cyclohexyl)methyl, cyclopropylmethyl, and homologs and isomers of, for example, n-pentyl, n-hexyl, n-heptyl, and n-octyl, or aryl, such as phenyl, naphthalyl, anthracenyl, phenanthryl, chrysenyl, pyrenyl, tolyl, or xylyl. In some forms, Z is also O.
In some forms, n is 14 (e.g., pentadecalactone, PDL), m is 7 (e.g., sebacic acid), o and p are 2 (e.g., N-methyldiethanolamine, MDEA).
In some embodiments, the polyplexes or particles are formed from polymer wherein $R_1$ and/or $R_2$ do not consist of or include

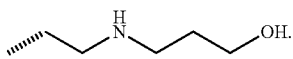

In some embodiments, polyplexes or particles formed from the polymer show improved loading, improved cellular transfection, improved intracellular endosomal release, or a combination thereof of a nucleic acid cargo, such as RNA, more particularly mRNA, relative to corresponding polyplexes or particles wherein $R_1$ and/or $R_2$ consist of or include

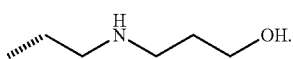

In some forms, the polymer has a structure of Formula II.

Formula II

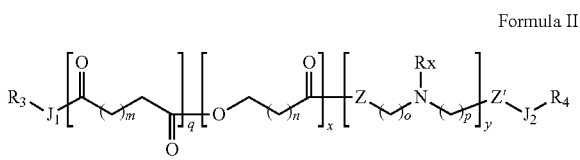

wherein $J_1$ and $J_2$ are independently linking moieties or absent, $R_3$ and $R_4$ are substituted alkyl containing a hydroxyl group, a primary amine group, a secondary amine group, a tertiary amine group, or combinations thereof.

In some forms, $J_1$ is —O— or —NH—.

In some forms, $J_2$ is —C(O)NH— or —C(O)O—.

In some forms, $R_3$ is identical to $R_4$.

Preferably $R_3$ and/or $R_4$ are linear.

In some forms, $R_3$, $R_4$ or both contain a hydroxyl group. In some forms, $R_3$, $R_4$ or both contain a hydroxyl group and one or more amine groups, preferably secondary or tertiary amine groups. In some forms, $R_3$, $R_4$ or both contain a hydroxyl group and no amine group.

In some forms, at least one of $R_3$ and $R_4$ does not contain a hydroxyl group.

In some forms, the polymer has a structure of Formula III.

Formula III

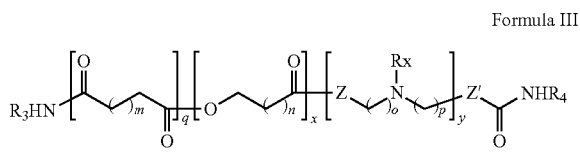

In particular embodiments, the values of x, y, and/or q are such that the weight average molecular weight of the polymer is greater than 20,000 Daltons, greater than 15,000 Daltons, greater than 10,000 Daltons, greater than 5,000 Daltons, greater than 2,000 Daltons. In some forms, the weight average molecular weight of the polymer is between about 2,000 Daltons and about 20,000 Daltons, more preferably between about 5,000 Daltons and about 10,000 Daltons.

The polymer can prepared from one or more lactones, one or more amine-diols (Z and Z'=O) or triamines (Z and Z'=NR'), and one or more diacids or diesters. In those embodiments where two or more different lactone, diacid or diester, and/or triamine or amine-diol monomers are used, the values of n, o, p, and/or m can be the same or different.

In some embodiments, the polymers are between about 2 kDa and 20 kDa, or between about 2 kDa and about 10 kDa, or between about 2 kDa and about 5 kDa.

The polymers can be used to form micro- and/or nanoparticles having encapsulated therein one or more therapeutic, diagnostic, and/or prophylactic agents. The agent to be encapsulated and delivered can be a small molecule agent (e.g., non-polymeric agent having a molecular weight less than 2,000, 1500, 1,000, 750, or 500 Daltons) or a macromolecule (e.g., an oligomer or polymer) such as proteins, enzymes, peptides, nucleic acids, etc. The particles can be used for in vivo and/or in vitro delivery of the agent.

In some forms, the particles have a solid core. Solid core nanoparticles confer the advantage of improved stability of the particles in solution and serum, such as occurs in vivo, relative to non-solid core particles. In some embodiments, the solid core nanoparticles are fabricated using a double emulsion technique.

The particles prepared from the polymers can be coated with surface charge altering materials, such as polypeptides, that increase stability and half-life of the particles in systemic circulation. The charge altering material can include a targeting moiety that increases targeting of the particles to a cell type or cell state of interest.

In some embodiments, the particles have a mean particle size from about 100 nm to about 300 nm, preferably from about 150 nm to about 275 nm. In some embodiments, the weight:weight ratio of polymer:polynucleotide is between about 25:1 and 250:1.

In some embodiments, the polymers can be used to form polymeric nanoparticulate polynucleotide carriers, referred to herein as polyplexes, which are effective for delivering the polynucleotides to cells in vitro and in vivo. The polyplexes have improved efficacy or reduced toxicity in vivo compared to other polynucleotide delivery approaches, enabling the polyplexes to be utilized in a broad range of therapeutic applications, for example, gene therapy. Typically, the polyplexes are less toxic and more efficient at transfecting polynucleotides when compared to a control, such as LIPOFECTAMINE 2000 or polyethylenimine (PEI). In some embodiments, the polyplexes are suitable for in vivo transfection, and can be used when other transfection reagents are too toxic or too inefficient to support in vivo applications. In some embodiments, the in vivo application includes systemic administration of the polyplexes.

In some embodiments, the polynucleotide is an RNA, such as an mRNA.

The polyplexes can be coated with one or more agents that reduce the surface charge of the polyplex at physiological pH. The coating can impart a neutral or negative surface charge to the polyplex. The agent can include, for example, a polypeptide with a series of negatively charged amino acids, such as glutamic acids or aspartic acids. In some embodiments, the polypeptide includes a cell targeting signal or cell targeting domain that enhances targeting of the polyplexes to a specific cell-type or cell-state. For example, the cell targeting domain can enhance targeting of the polyplexes to cancer cells. Exemplary cell targeting domains include RGD, R/KxxR/K (SEQ ID NO:7) where "x" is any amino acid, GdPdLGdVdRG (SEQ ID NO:5), and ASGPR (SEQ ID NO:6). In some embodiments, the stretch of negatively charged amino acids and the cell targeting domain are linked by a linker polypeptide. The linker can be a series of glycines. An exemplary coating including an agent that reduces surface charge and provides cell specific targeting to cancer cells is EEEEEEEEEEEEEEEEGGGGGGRGDK (SEQ ID NO:1).

Polyplexes and particles formed of the polymers have several advantages over nanoparticles formed with hydrophobic polymers. Solid core nanoparticles fabricated from hydrophobic polymers often require the presence of cationic complexing agents to stabilize polynucleotides, particularly negatively charged polynucleotides.

The polynucleotide can include a sequence that encodes a protein (e.g., DNA or mRNA), a sequence that encodes a functional nucleic acid, or can itself be a functional nucleic acid, rRNA, or tRNA. Functional nucleic acids include, but are not limited to, antisense molecules, siRNA, miRNA, aptamers, ribozymes, triplex forming molecules, RNAi, and external guide sequences. In some embodiments, the polynucleotide includes an expression control sequence operably linked to a sequence encoding a protein, functional nucleic acid, rRNA, or tRNA. For example, the polynucleotide can be an expression vector. Exemplary polynucleotides include, but are not limited to mRNA, DNA vectors, antisense molecules, siRNA, miRNA, aptamers, ribozymes, triplex forming molecules, RNAi, external guide sequences, CRISPR/Cas constructs, etc. As discussed in more detail below, in some embodiments the triplex-forming molecule is a tail clamp peptide nucleic acid (tcPNA). The polynucleotide deliverable by the particles can be a functional nucleic acid or can be a vector, RNA, or other polynucleotide encoding a functional nucleic acid and designed for expression thereof in cells of interest. The polynucleotide can be single stranded or double stranded.

Complexing agents are optional in the formulations because, as discussed in more detail below, the nanoparticles contain cationic amines to stabilize negatively charged nucleic acids and hydrophobic domains to condense the nucleic acid into the core of the formed nanoparticles, thus improving encapsulation efficiency. This increase in nucleic acid loading allows the solid core nanoparticles to deliver more nucleic acid per cell without increasing total polymer delivered, further reducing cytotoxicity. Cationic delivery platforms are often limited by high cytotoxicity. In comparison, the nanoparticles offer the advantage of reduced cytotoxicity (low density of cationic amines and high density of hydrophobic domains) and effective nucleic acid transfection. Pharmaceutical compositions including an effective amount of the nanoparticles are also provided, and can be used, for example, for in vitro and in vivo delivery of nucleic acids and other active agents.

Compositions, such as pharmaceutical compositions, containing the particles are also disclosed. The particles can be contacted with cells to transfect the agent, such as a polynucleotide, into the cells. In some embodiments, the contacting occurs in vivo by administering the particles, or a pharmaceutical composition containing the particles, to a subject in an effective amount to treat a disease or condition. The disease or condition can be, for example, a mitochondrial disease, an infectious disease, a cancer, a metabolic disorder, an autoimmune disease, an inflammatory disorder, or an age-related disorder. The particles can be administered parenterally, transdermally, or transmucosally. The particles can be administered systemically or locally.

In some embodiments, contacting the cells with polyplexes to transfect the polynucleotide occurs in vitro, or ex vivo. The cells can be primary cells or cells from a cell line. The primary cells can be harvested from a subject. In some embodiments, the transfected cells are administered back to the subject, or to a different subject as part of a cell-based therapy for treating a disease or condition.

Methods of use are also provided. For example, a method of delivering an active agent to cells can include contacting the cells with an effective amount of nanoparticles including the active agent. In some embodiments in which the active agent is a polynucleotide, and a method of transfecting cells includes contacting the cells with an effective amount of the nanoparticles including the polynucleotide. The method of reducing expression of a target gene can include contacting cells expressing the gene with an effective amount of a pharmaceutical composition including nanoparticles with an inhibitory nucleic acid encapsulated, entrapped, embedded, or dispersed therein, or complexed thereto, to reduce expression of the target gene in the cells. The inhibitory nucleic acid can be, for example, an siRNA, miRNA, or a mimic thereof, for example a construct composed of DNA or synthetic nucleotides, but that can have the same molecular weight as RNA. In some embodiments, the polynucleotide is less than 1,000 nucleotides, less than 500 nucleotides, less than 250 nucleotides, less than 100 nucleotides, between about 10 and about 50 nucleotides in length, between about 18 and 28 nucleotides in length, or between about 20 and 25 nucleotides in length. In a particular embodiment, the polynucleotide is 22 nucleotides in length. The polynucleotide can be single-stranded or double-stranded. The contacting can occur in vitro or in vivo. The pharmaceutical composition can be administered to a subject in an effective amount for the inhibitory nucleic acid to reduce one or more disease or disorder symptoms in a subject in need thereof. In some embodiments, reduced expression of the target gene in the subject is sustained for at least 2 week.

6C-6F are bar graphs showing blood chemistry (AST (FIG. 6C), ALT (FIG. 6D), Urea (FIG. 6E), Creatinine (FIG. 6F)) analysis 24 h and 7 days after IV administration of acetate buffer, free mRNA or mRNA:aPACE polyplexes. Results are presented as mean±SEM of N=3 animals.

Figure 7:
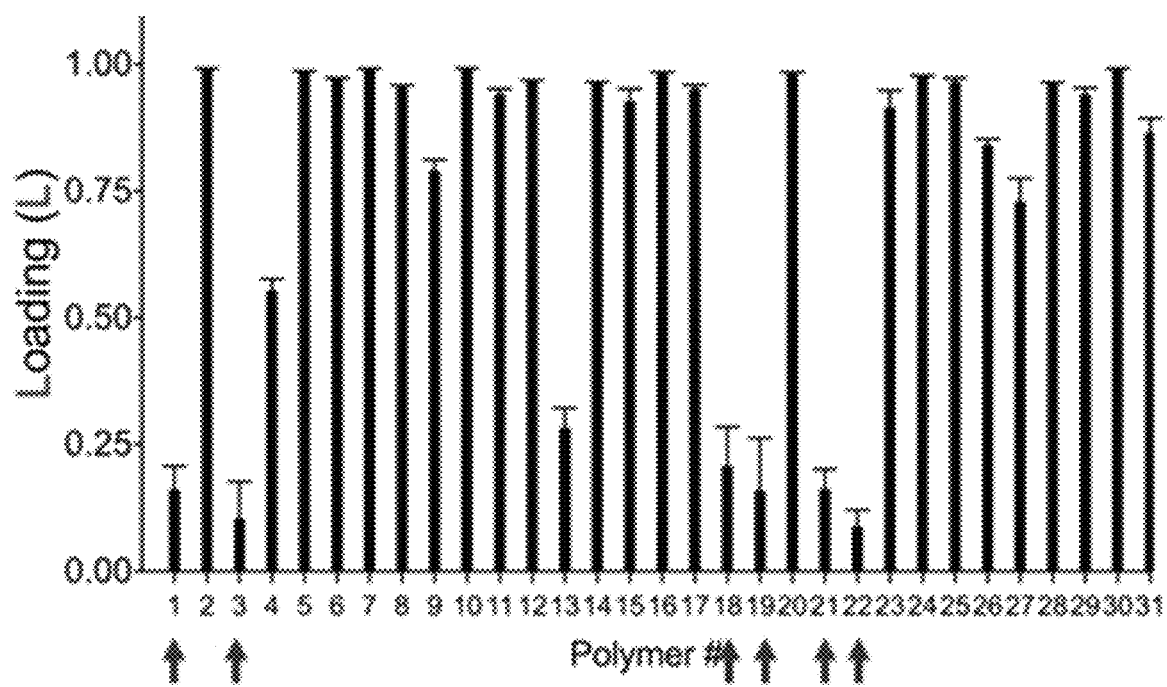

FIG. 7 is a bar graph showing the effect of PACE end group (#corresponding to end groups identified in Example 5 on mRNA loading onto polyplexes.

Figure 8A:
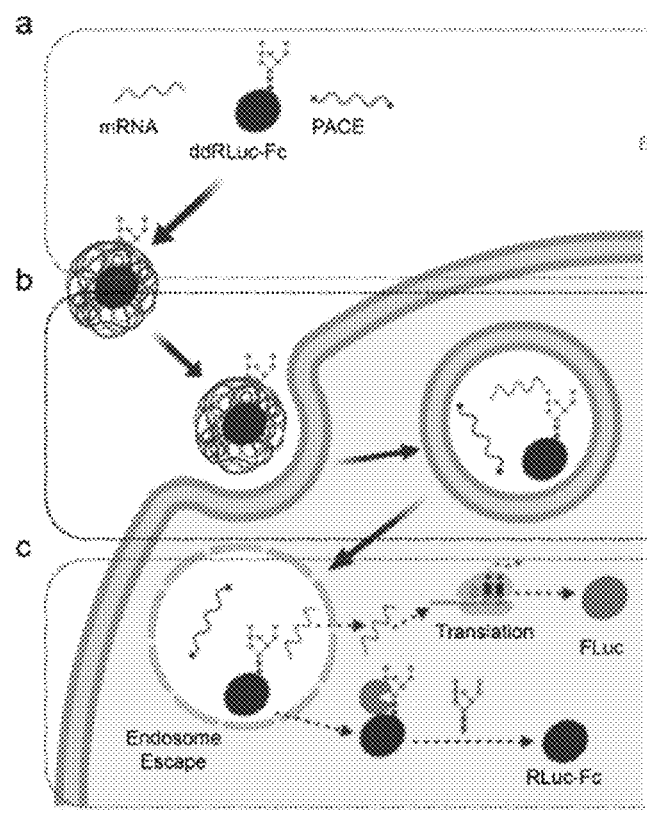
Figure 8B:
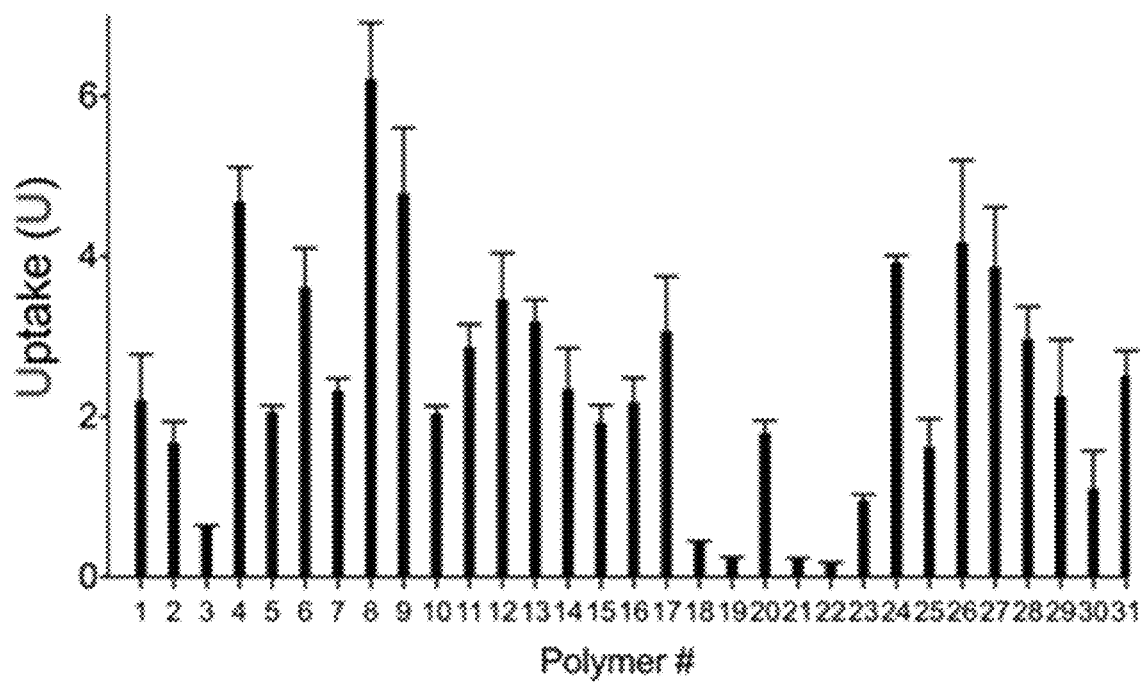
Figure 8C:
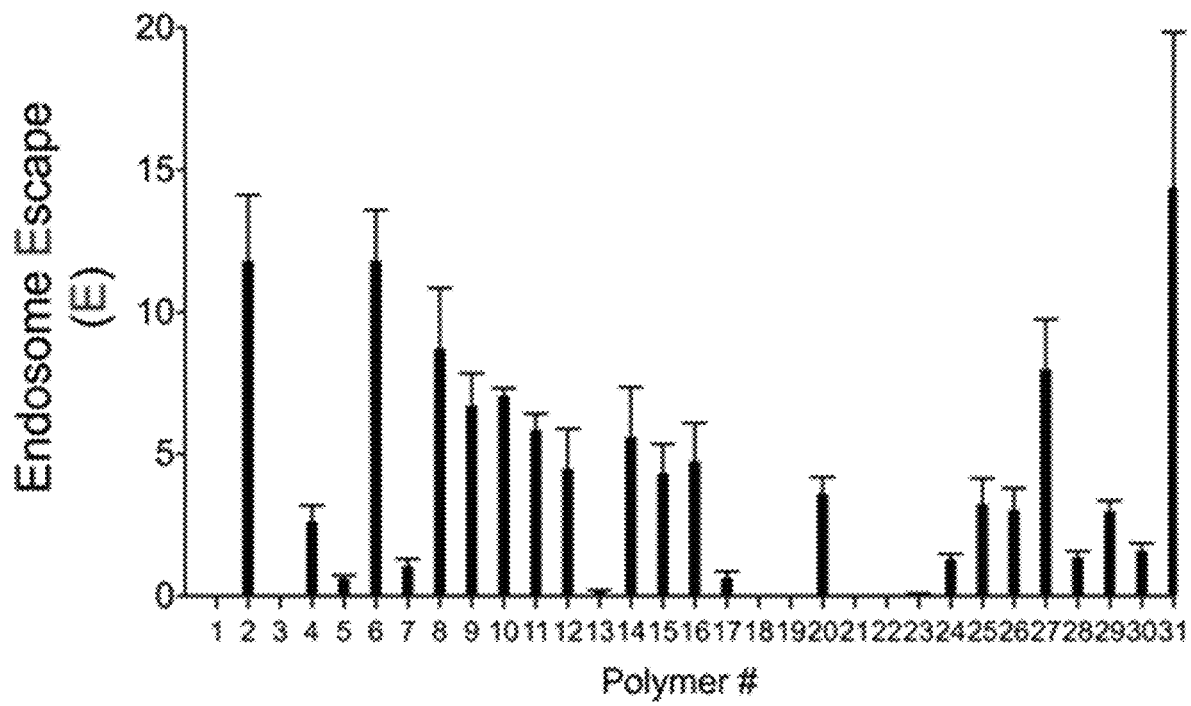
Figure 8D:
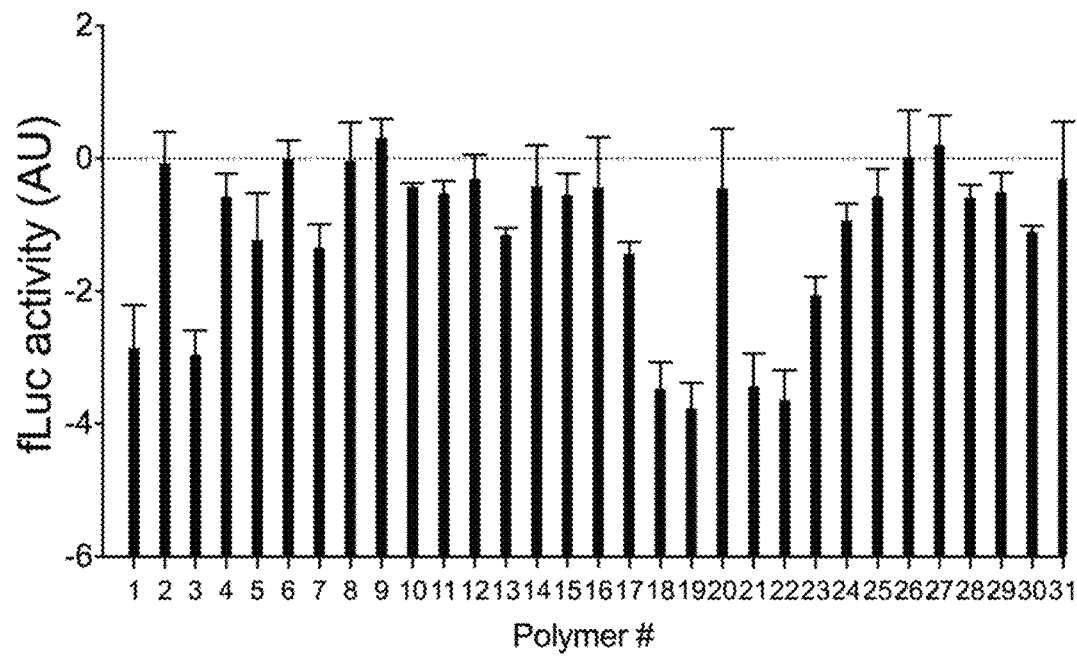

FIG. 8A is a schematic of the mechanisms producing the results show in FIGS. 8B-8D. FIG. 8B is a bar graph showing the effect of PACE end group (#corresponding to end groups identified in Example 5) on cellular uptake of polyplexes. FIG. 8C is a bar graph showing the effect of PACE end group (#corresponding to end groups identified in Example 5) on endosomal escape. FIG. 8D is a bar graph showing the effect of PACE end group (#corresponding to end groups identified in Example 5) on transfection efficiency.

Figure 9A:
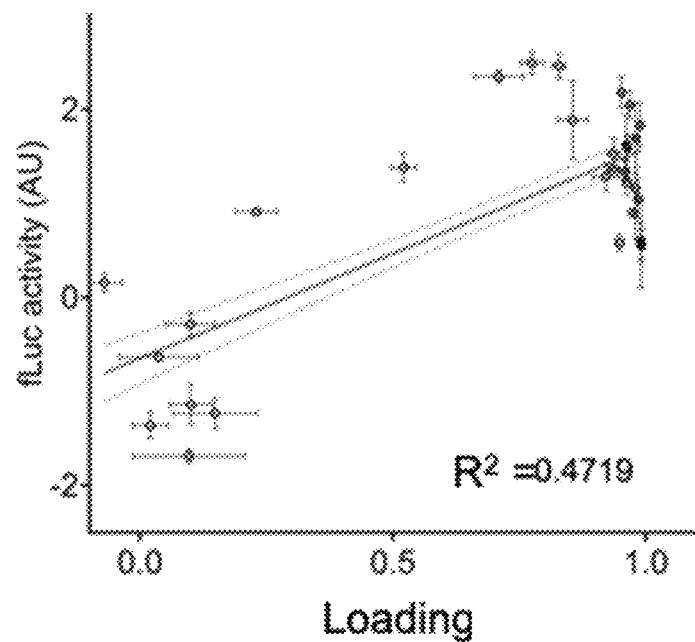
Figure 9B:
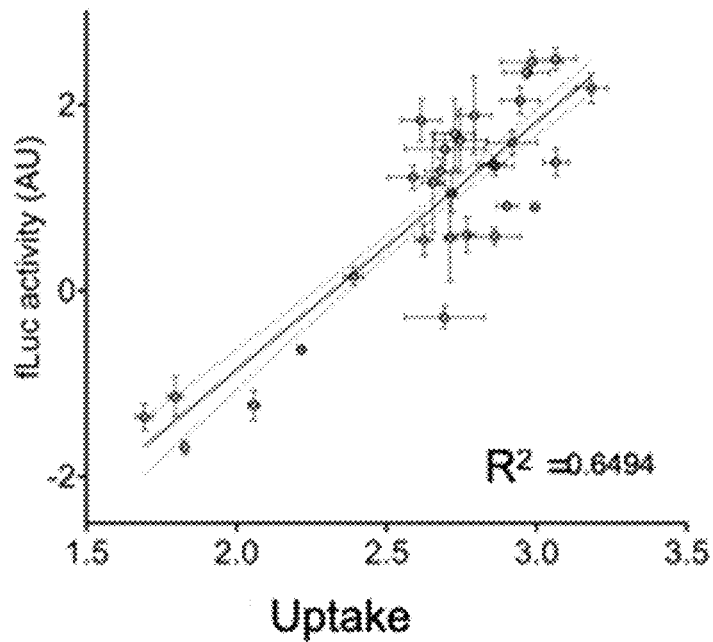
Figure 9C:
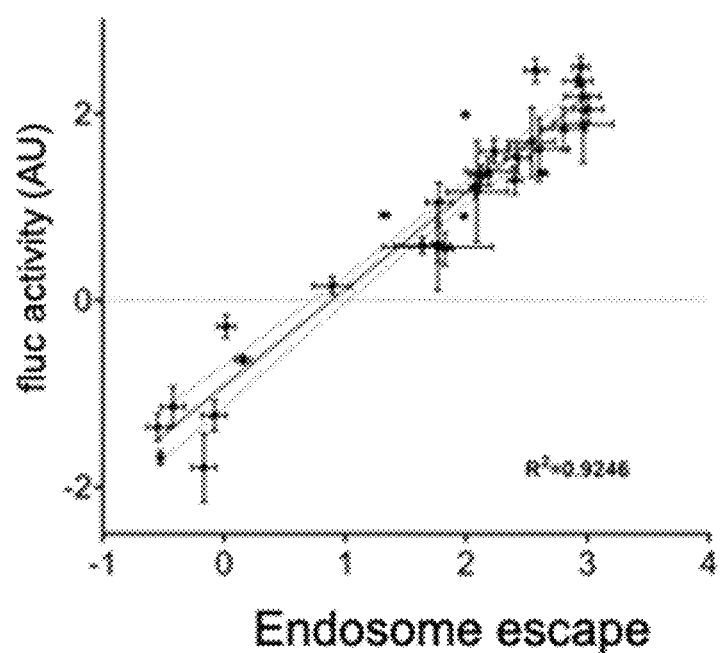

FIGS. 9A-9C are plots showing the linear correlation of transfection efficiency (represented as fluc activity) and different steps of transfection, including mRNA loading (FIG. 9A), uptake (FIG. 9B), and endosome escape (FIG. 9C).

Figure 10A:
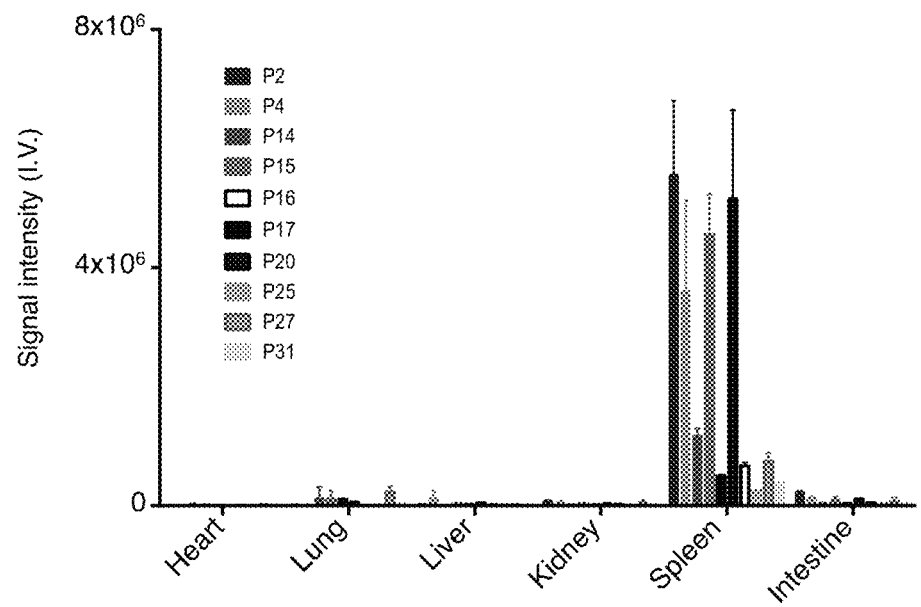
Figure 10B:
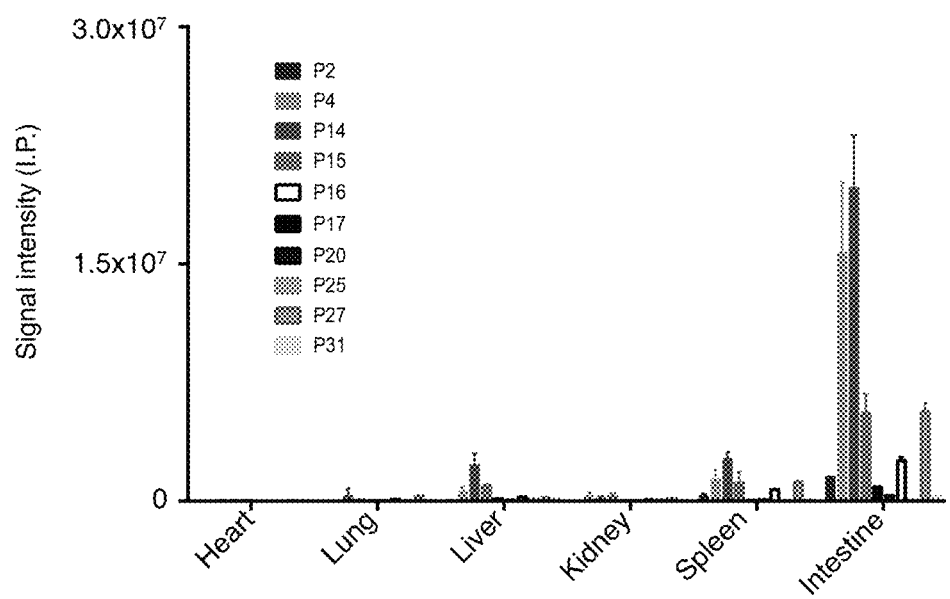

FIGS. 10A and 10B are plots (data from IVIS images) showing the biodistribution of the polyplexes measured by bioluminescence distribution 6 h after I.P. injection (FIG. 10A) and after I.V. injection (FIG. 10B) for, heart, lung, liver, kidney, spleen, intestine.

DETAILED DESCRIPTION OF THE INVENTION

I. Definitions

The terms "lactone" and "lactone unit" are used to describe a chemical compound that includes a cyclic ester, or the open chain chemical structure that results from the cleavage of the ester bond in the cyclic ester. For example, lactone is used to describe the cyclic ester shown below, and the corresponding lactone-derived open chain structure:

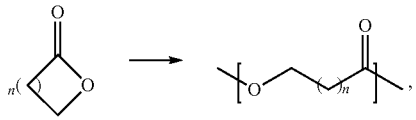

n being an integer. The open chain structure is formed via methods known in the art, including but not limited to, solvolysis, such as hydrolysis, and enzymatic cleavage.

The term "polyplex" as used herein refers to polymeric micro- and/or nanoparticles or micelles typically having encapsulated therein, dispersed within, and/or associated with the surface of, one or more polynucleotides.

The term "solid core" as relates to "particles" is used to describe a plurality of particles in which the core of each particle contains a matrix that includes one or more materials that are used to form the particles. The particles can be microspheres, microcapsules, microparticles, nanospheres, nanocapsules, and nanoparticles, referred to as solid core microspheres, solid core microcapsules, solid core microparticles, solid core nanospheres, solid core capsules, and solid core nanoparticles, respectively.

The term "microspheres" is art-recognized, and includes substantially spherical colloidal structures, e.g., formed from biocompatible polymers such as subject compositions, having a size ranging from about one or greater up to about 1000 microns. In general, "microcapsules," also an art-recognized term, may be distinguished from microspheres, because microcapsules are generally covered by a substance of some type, such as a polymeric formulation. The term "microparticles" is also art-recognized, and includes microspheres and microcapsules, as well as structures that may not be readily placed into either of the above two categories, all with dimensions on average of less than about 1000 microns. A microparticle may be spherical or nonspherical and may have any regular or irregular shape. If the structures are less than about one micron (1000 nm) in diameter, then the corresponding art-recognized terms "nanosphere," "nanocapsule," and "nanoparticle" may be utilized. In certain embodiments, the nanospheres, nanocapsules and nanoparticles have an average diameter of about 500 nm, 200 nm, 100 nm, 50 nm, 10 nm, or 1 nm. In some embodiments, the average diameter of the particles is from about 200 nm to about 600 nm, preferably from about 200 to about 500 nm. Microparticles can be used for gene therapy, particularly for vaccinations.

A composition containing microparticles or nanoparticles may include particles of a range of particle sizes. In certain embodiments, the particle size distribution may be uniform, e.g., within less than about a 20% standard deviation of the mean volume diameter, and in other embodiments, still more uniform, e.g., within about 10%, 8%, 5%, 3%, or 2% of the median volume diameter.

The term "particle" as used herein refers to any particle formed of, having attached thereon or thereto, or incorporating a therapeutic, diagnostic or prophylactic agent, optionally including one or more polymers, liposomes micelles, or other structural material. A particle may be spherical or nonspherical. A particle may be used, for example, for diagnosing a disease or condition, treating a disease or condition, or preventing a disease or condition.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

The terms "subject," "individual," and "patient" refer to any individual who is the target of treatment using the compositions. The subject can be a vertebrate, for example, a mammal. Thus, the subject can be a human. The subjects can be symptomatic or asymptomatic. The term does not denote a particular age or sex. Thus, adult and newborn subjects, whether male or female, are intended to be covered. A subject can include a control subject or a test subject.

The term "biocompatible" as used herein refers to one or more materials that are neither themselves toxic to the host (e.g., an animal or human), nor degrade (if the material degrades) at a rate that produces monomeric or oligomeric subunits or other byproducts at toxic concentrations in the host.

The term "biodegradable" as used herein means that the materials degrades or breaks down into its component subunits, or digestion, e.g., by a biochemical process, of the material into smaller (e.g., non-polymeric) subunits.

The term "diameter" is art-recognized and is used herein to refer to either of the physical diameter or the hydrodynamic diameter. The diameter of an essentially spherical particle may refer to the physical or hydrodynamic diameter. The diameter of a nonspherical particle may refer preferentially to the hydrodynamic diameter. As used herein, the diameter of a non-spherical particle may refer to the largest linear distance between two points on the surface of the particle. When referring to multiple particles, the diameter of the particles typically refers to the average diameter of the particles. Particle diameter can be measured using a variety of techniques in the art including, but not limited to, dynamic light scattering.

"Sustained release" as used herein refers to release of a substance over an extended period of time in contrast to a bolus type administration in which the entire amount of the substance is made biologically available at one time.

The phrases "parenteral administration" and "administered parenterally" are art-recognized terms, and include modes of administration other than enteral and topical administration, such as injections, and include without limitation intravenous, intramuscular, intrapleural, intravascular, intrapericardial, intraarterial, intrathecal, intracapsular, intraorbital, intracardiac, intradennal, intraperitoneal, transtracheal, subcutaneous, subcuticular, intraarticular, subcapsular, subarachnoid, intraspinal and intrasternal injection and infusion.

The term "surfactant" as used herein refers to an agent that lowers the surface tension of a liquid.

The term "targeting moiety" as used herein refers to a moiety that localizes to or away from a specific locale. The moiety may be, for example, a protein, nucleic acid, nucleic acid analog, carbohydrate, or small molecule. Said entity may be, for example, a therapeutic compound such as a small molecule, or a diagnostic entity such as a detectable label. Said locale may be a tissue, a particular cell type, or a subcellular compartment. In one embodiment, the targeting moiety directs the localization of an active entity. The active entity may be a small molecule, protein, polymer, or metal. The active entity may be useful for therapeutic, prophylactic, or diagnostic purposes.

The term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups.

In preferred embodiments, a straight chain or branched chain alkyl has 30 or fewer carbon atoms in its backbone (e.g., $C_1$-$C_{30}$ for straight chains, $C_3$-$C_{30}$ for branched chains), preferably 20 or fewer, more preferably 15 or fewer, most preferably 10 or fewer. All integer values of the number of backbone carbon atoms between one and 30 are contemplated and disclosed for the straight chain or branched chain alkyls. Likewise, preferred cycloalkyls have from 3-10 carbon atoms in their ring structure, and more preferably have 5, 6, or 7 carbons in the ring structure. All integer values of the number of ring carbon atoms between three and 10 are contemplated and disclosed for the cycloalkyls.

The term "alkyl" (or "lower alkyl") as used throughout the specification, examples, and claims is intended to include both "unsubstituted alkyls" and "substituted alkyls", the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

It will be understood by those skilled in the art that the moieties substituted on the hydrocarbon chain can themselves be substituted, if appropriate. For instance, the substituents of a substituted alkyl may include halogen, hydroxy, nitro, thiols, amino, azido, imino, amido, phosphoryl (including phosphonate and phosphinate), sulfonyl (including sulfate, sulfonamido, sulfamoyl and sulfonate), and silyl groups, as well as ethers, alkylthios, carbonyls (including ketones, aldehydes, carboxylates, and esters), —$CF_3$, —CN and the like. Cycloalkyls can be substituted in the same manner.

"Aryl", as used herein, refers to $C_5$-$C_{10}$-membered aromatic, heterocyclic, fused aromatic, fused heterocyclic, biaromatic, or bihetereocyclic ring systems. In some forms, the ring systems have 3-50 carbon atoms. Broadly defined, "aryl", as used herein, includes 5-, 6-, 7-, 8-, 9-, 10- and 24-membered single-ring aromatic groups that may include from zero to four heteroatoms, for example, benzene, naphthalene, anthracene, phenanthrene, chrysene, pyrene, corannulene, coronene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with one or more substituents including, but not limited to, halogen, azide, alkyl, aralkyl, alkenyl, alkynyl, cycloalkyl, hydroxyl, alkoxyl, amino (or quaternized amino), nitro, sulfhydryl, imino, amido, phosphonate, phosphinate, carbonyl, carboxyl, silyl, ether, alkylthio, sulfonyl, sulfonamido, ketone, aldehyde, ester, heterocyclyl, aromatic or heteroaromatic moieties, —$CF_3$, —CN; and combinations thereof.

The term "aryl" also includes polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1, 5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. One or more of the rings can be substituted as defined above for "aryl".

"Alkoxy" refers to an alkyl group as defined above with the indicated number of carbon atoms attached through an oxygen bridge. Examples of alkoxy include, but not limited to, methoxy, ethoxy, n-propoxy, i-propoxy, n-butoxy, s-butoxy, n-pentoxy, s-pentoxy, and derivatives thereof.

Primary amines arise when one of three hydrogen atoms in ammonia is replaced by a substituted or unsubstituted alkyl or a substituted or unsubstituted aryl group. Secondary amines have two organic substituents (substituted or unsubstituted alkyl, substituted or unsubstituted aryl or combinations thereof) bound to the nitrogen together with one hydrogen. In tertiary amines, nitrogen has three organic substituents.

"Substituted", as used herein, means one or more atoms or groups of atoms on the monomer has been replaced with one or more atoms or groups of atoms which are different than the atom or group of atoms being replaced. In some embodiments, the one or more hydrogens on the monomer is replaced with one or more atoms or groups of atoms. Examples of functional groups which can replace hydrogen are listed above in the definition. In some embodiments, one or more functional groups can be added which vary the chemical and/or physical property of the resulting monomer/polymer, such as charge or hydrophilicity/hydrophobicity, etc. Exemplary substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, phosphinate, amino, amido, amidine, imine, cyano, nitro, azido, sulfhydryl, alkylthio, sulfate, sulfonate, sulfamoyl, sulfonamido, sulfonyl, nitro, heterocyclyl, aralkyl, or an aromatic or heteroaromatic moiety.

As used herein, "transient" refers to expression of a non-integrated transgene for a period of hours, days or weeks, wherein the period of time of expression is less than the period of time for expression of the gene if integrated into the genome or contained within a stable plasmid replicon in the host cell.

As used herein, a "promoter site" is a sequence of nucleotides to which an RNA polymerase, such as the DNA-dependent RNA polymerase originally isolated from bacteriophage, described by Davanloo, et al., *Proc. Natl. Acad. Sci. USA*, 81:2035-39 (1984), or from another source, binds with high specificity, as described by Chamberlin, et al., *Nature*, 228:227-231 (1970).

As used herein, a "poly(A)" is a series of adenosines attached by polyadenylation to the mRNA. In the preferred embodiment of a construct for transient expression, the polyA is between 50 and 5000, preferably greater than 64, more preferably greater than 100, most preferably greater than 300 or 400. poly(A) sequences can be modified chemically or enzymatically to modulate mRNA functionality such as localization, stability or efficiency of translation.

As used herein, an "open reading frame" or "ORF" is a series of nucleotides that contains a sequence of bases that could potentially encode a polypeptide or protein. An open reading frame is located between the start-code sequence (initiation codon or start codon) and the stop-codon sequence (termination codon).

The term "construct" refers to a recombinant genetic molecule having one or more isolated polynucleotide sequences.

The term "expression control sequence" refers to a nucleic acid sequence that controls and regulates the transcription and/or translation of another nucleic acid sequence. Control sequences that are suitable for prokaryotes, for example, include a promoter, optionally an operator sequence, a ribosome binding site, and the like. Eukaryotic cells are known to utilize promoters, polyadenylation signals, and enhancers.

The term "gene" refers to a DNA sequence that encodes through its template or messenger RNA a sequence of amino acids characteristic of a specific peptide, polypeptide, or protein. The term "gene" also refers to a DNA sequence that encodes an RNA product. The term gene as used herein with reference to genomic DNA includes intervening, non-coding regions as well as regulatory regions and can include 5' and 3' ends.

The term polypeptide includes proteins and fragments thereof. The polypeptides can be "exogenous," meaning that they are "heterologous," i.e., foreign to the host cell being utilized, such as human polypeptide produced by a bacterial cell. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

"Variant" refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides which do not significantly alter the characteristics of the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties. In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Substitution of like amino acids can also be made on the basis of hydrophilicity, particularly where the biological functional equivalent polypeptide or peptide thereby created is intended for use in immunological embodiments. Amino acid substitutions are generally based on the relative similarity of the amino acid side-chain substituents, for example, their hydrophobicity, hydrophilicity, charge, and size.

Unless otherwise indicated, the disclosure encompasses conventional techniques of molecular biology, microbiology, cell biology and recombinant DNA, which are within the skill of the art. See, e.g., Sambrook and Russell, Molecular Cloning: A Laboratory Manual, 3rd edition (2001); Current Protocols In Molecular Biology [(Ausubel, et al. eds., (1987)]; Coligan, Dunn, Ploegh, Speicher and Wingfeld, eds. (1995) Current Protocols in Protein Science (John Wiley & Sons, Inc.); the series Methods in Enzymology (Academic Press, Inc.): PCR 2: A Practical Approach (M. J. MacPherson, B. D. Hames and G. R. Taylor eds. (1995)].

II. Polymers

Polymers including poly(amine-co-ester), poly(amine-co-amide), or a combination thereof, and polyplexes and solid core particles formed therefrom. Poly(amine-co-ester) are discussed in WO 2013/082529, WO 2017/151623, WO 2017/197128, U.S. Published Application No. 2016/0251477, U.S. Published Application No. 2015/0073041, and U.S. Pat. No. 9,272,043.

When used to deliver gene materials, the transfection efficiency of the polymers is strongly dependent on the end groups on the polymers. When substituting the diester monomer in the polymers with diacid, such as sebacic acid, polymers with a mixture of hydroxyl and carboxyl end groups can be obtained. Both of these two end groups can be activated with 1,1'-carbodiimidazole. The activated product can react with amine-containing molecules to yield polymers with new end groups.

The polymers can be further hydrolyzed to release more active end groups, such as —OH and —COOH, both of which can originate from hydrolysis of ester bonds in the polymers (also referred to herein as "actuation"), typically by incubating the polymers, e.g., at a control temperature (e.g., 37° C. or 100° C.), for days or weeks. In some embodiments, the polymers are not hydrolyzed, and thus can be referred to as "non-actuated."

In some embodiments, the content of a hydrophobic monomer in the polymer is increased relative the content of the same hydrophobic monomer when used to form polyplexes. Increasing the content of a hydrophobic monomer in the polymer forms a polymer that can form solid core nanoparticles in the presence of nucleic acids, including RNAs.

Unlike polyplexes, these particles are stable for long periods of time during incubation in buffered water, or serum, or upon administration (e.g., injection) into animals. They also provide for a sustained release of nucleic acids (e.g., siRNA) which leads to long term activity (e.g., siRNA mediate-knockdown).

A. Polymer Structure

Poly(amine-co-ester)s or poly(amine-co-amide)s are described herein. In some forms, the polymer has a structure as shown in Formula I:

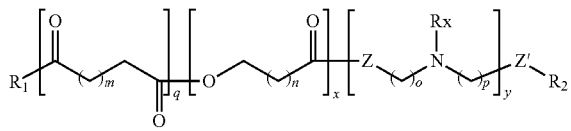

Formula I wherein n is an integer from 1-30,
m, o, and p are independently integers from 1-20,
x, y, and q are independently integers from 1-1000,
$R_x$ is hydrogen, substituted or unsubstituted alkyl, or substituted or unsubstituted aryl, or substituted or unsubstituted alkoxy,
Z and Z' are independently O or NR', wherein R' is hydrogen, substituted or unsubstituted alkyl, or substituted or unsubstituted aryl,
$R_1$ and $R_2$ are chemical entities containing a hydroxyl group, a primary amine group, a secondary amine group, a tertiary amine group, or combinations thereof.

Examples of $R_x$ and R' groups include, but are not limited to, hydrogen, methyl, ethyl, n-propyl, isopropyl, n-butyl, t-butyl, isobutyl, sec-butyl, cyclohexyl, (cyclohexyl)methyl, cyclopropylmethyl, and homologs and isomers of, for example, n-pentyl, n-hexyl, n-heptyl, n-octyl, phenyl, naphthalyl, anthracenyl, phenanthryl, chrysenyl, pyrenyl, tolyl, xylyl, etc.

In particular embodiments, the values of x, y, and/or q are such that the weight average molecular weight of the polymer is greater than 20,000 Daltons, greater than 15,000 Daltons, greater than 10,000 Daltons, greater than 5,000 Daltons, greater than 2,000 Daltons. In some forms, the weight average molecular weight of the polymer is between about 2,000 Daltons and about 20,000 Daltons, more preferably between about 5,000 Daltons and about 10,000 Daltons.

The polymer can be prepared from one or more lactones, one or more amine-diols (Z and Z'=O), triamines (Z and Z'=NR'), or hydroxy-diamines (Z=O and Z'=NR', or Z=NR' and Z'=O) and one or more diacids or diesters. In those embodiments where two or more different lactone, diacid or diester, and/or triamine, amine-diol, or hydroxy-diamine monomers are used, the values of n, o, p, and/or m can be the same or different.

In some forms, the percent composition of the lactone unit is between about 10% and about 100%, calculated lactone unit vs. (lactone unit+diester/diacid). Expressed in terms of a molar ratio, the lactone unit vs. (lactone unit+diester/diacid) content is between about 0.1 and about 1, i.e., x/(x+q) is between about 0.1 and about 1. Preferably, the number of carbon atoms in the lactone unit is between about 10 and about 24, more preferably the number of carbon atoms in the lactone unit is between about 12 and about 16. Most preferably, the number of carbon atoms in the lactone unit is 12 (dodecalactone), 15 (pentadecalactone), or 16 (hexadecalactone).

In some forms, Z is the same as Z'.
In some forms, Z is O and Z' is O. In some forms, Z is NR' and Z' is NR'. In some forms, Z is O and Z' is NR'. In some forms, Z is NR' and Z' is O.
In some forms, Z' is O and n is an integer from 1-24, such as 4, 10, 13, or 14. In some forms, Z is also O.
In some forms, Z' is O, n is an integer from 1-24, such as 4, 10, 13, or 14, and m is an integer from 1-10, such as 4, 5, 6, 7, or 8. In some forms, Z is also O.

In some forms, Z' is O, n is an integer from 1-24, such as 4, 10, 13, or 14, m is an integer from 1-10, such as 4, 5, 6, 7, or 8, and o and p are the same integer from 1-6, such 2, 3, or 4. In some forms, Z is also O.

In some embodiments, Z' is O, n is an integer from 1-24, such as 4, 10, 13, or 14, m is an integer from 1-10, such as 4, 5, 6, 7, or 8, and R is alkyl, such a methyl, ethyl, n-propyl, isopropyl, n-butyl, t-butyl, isobutyl, sec-butyl, cyclohexyl, (cyclohexyl)methyl, cyclopropylmethyl, and homologs and isomers of, for example, n-pentyl, n-hexyl, n-heptyl, and n-octyl, or aryl, such as phenyl, naphthalyl, anthracenyl, phenanthryl, chrysenyl, pyrenyl, tolyl, or xylyl. In some forms, Z is also O.

In some forms, n is 14 (e.g., pentadecalactone, PDL), m is 7 (e.g., sebacic acid), o and p are 2 (e.g., N-methyldiethanolamine, MDEA).

In some embodiments, the polyplexes or particles are formed from polymer wherein R1 and/or R2 are not relative to corresponding polyplexes wherein R1 and/or R2 consist of or include

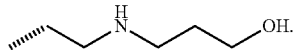

In some embodiments, polyplexes or particles formed from the polymer show improved loading, improved cellular transfection, improved intracellular endosomal release, or a combination thereof of a nucleic acid cargo, such as RNA, more particularly mRNA, relative to corresponding polyplexes wherein R1 and/or R2 consist of or include

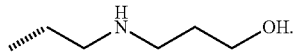

In some forms, the polymer has a structure of Formula II.

Formula II

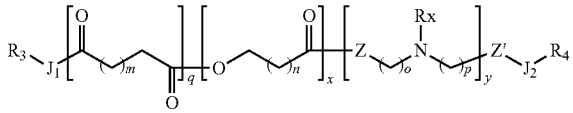

wherein $J_1$ and $J_2$ are independently linking moieties or absent, $R_3$ and $R_4$ are independently substituted alkyl containing a hydroxyl group, a primary amine group, a secondary amine group, a tertiary amine group, or combinations thereof. In some forms, the molecular weight of $R_3$, $R_4$ or both are at or below 500 Daltons, at or below 200 Daltons, or at or below 100 Daltons.

In some forms, $J_1$ is —O— or —NH—.
In some forms, $J_2$ is —C(O)NH— or —C(O)O—.
In some forms, $R_3$ is identical to $R_4$.
Preferably, $R_3$ and/or $R_4$ are linear.
In some forms, $R_3$, $R_4$ or both contain a primary amine group. In some forms, $R_3$, $R_4$ or both contain a primary amine group and one or more secondary or tertiary amine groups.
In some forms, $R_3$, $R_4$ or both contain a hydroxyl group. In some forms, $R_3$, $R_4$ or both contain a hydroxyl group and one or more amine groups, preferably secondary or tertiary amine groups. In some forms, $R_3$, $R_4$ or both contain a hydroxyl group and no amine group.

In some forms, at least one of $R_3$ and $R_4$ does not contain a hydroxyl group.

In some forms, $R_3$, $R_4$ or both are -unsubstituted $C_1$-$C_{10}$ alkylene-Aq-unsubstituted $C_1$-$C_{10}$ alkylene-Bq, -unsubstituted $C_1$-$C_{10}$ alkylene-Aq-substituted $C_1$-$C_{10}$ alkylene-Bq, -substituted $C_1$-$C_{10}$ alkylene-Aq-unsubstituted $C_1$-$C_{10}$ alkylene-Bq, or -substituted $C_1$-$C_{10}$ alkylene-Aq-substituted $C_1$-$C_{10}$ alkylene-Bq, wherein Aq is absent or —$NR_5$—, and Bq is hydroxyl, primary amine, secondary amine, or tertiary amine, wherein $R_5$ is hydrogen, substituted or unsubstituted alkyl, or substituted or unsubstituted aryl.

Figure 1:
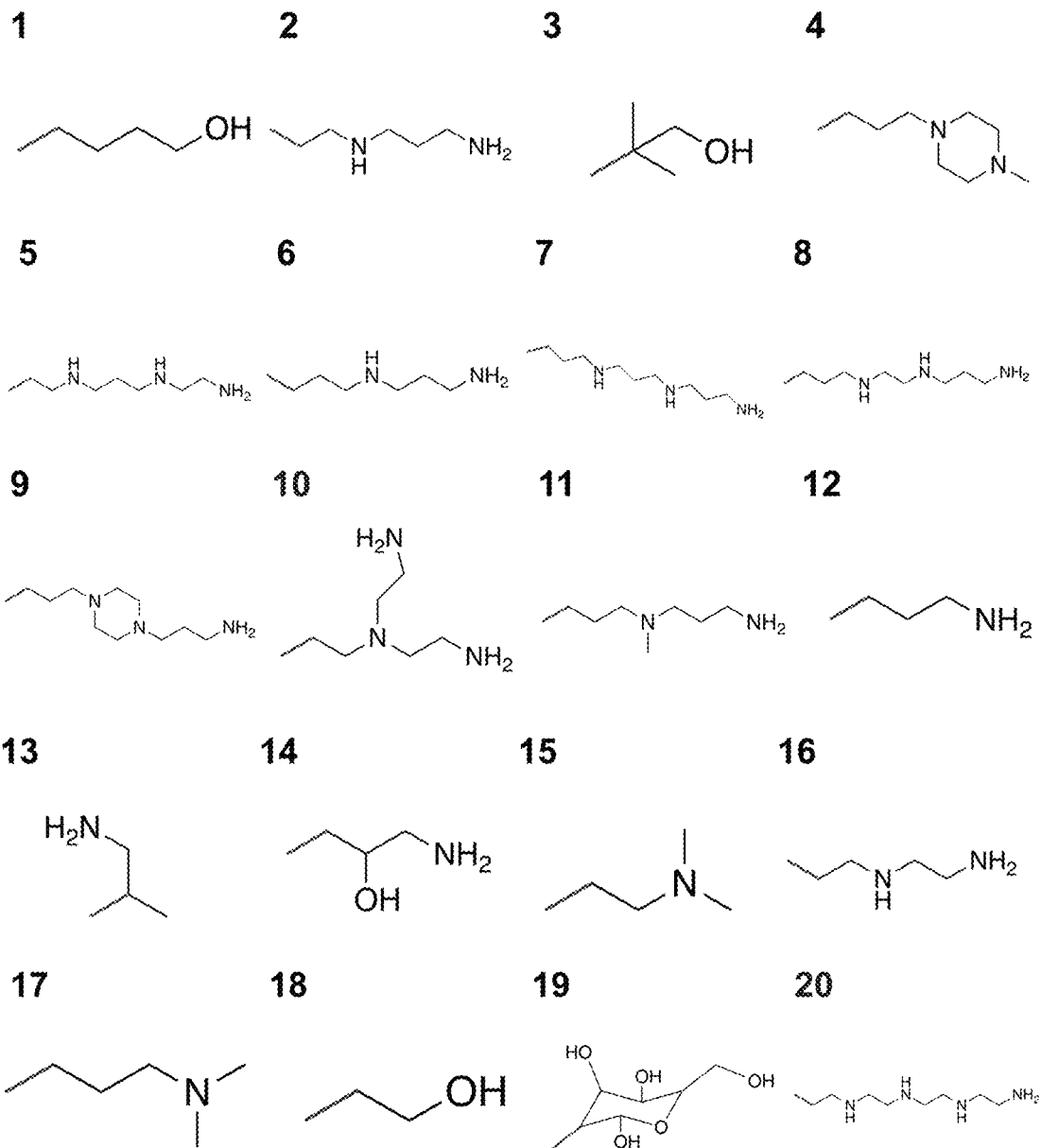
FIG. 1 shows $R_3$ and $R_4$ groups that may be incorporated into Formula I.
Figure 1:
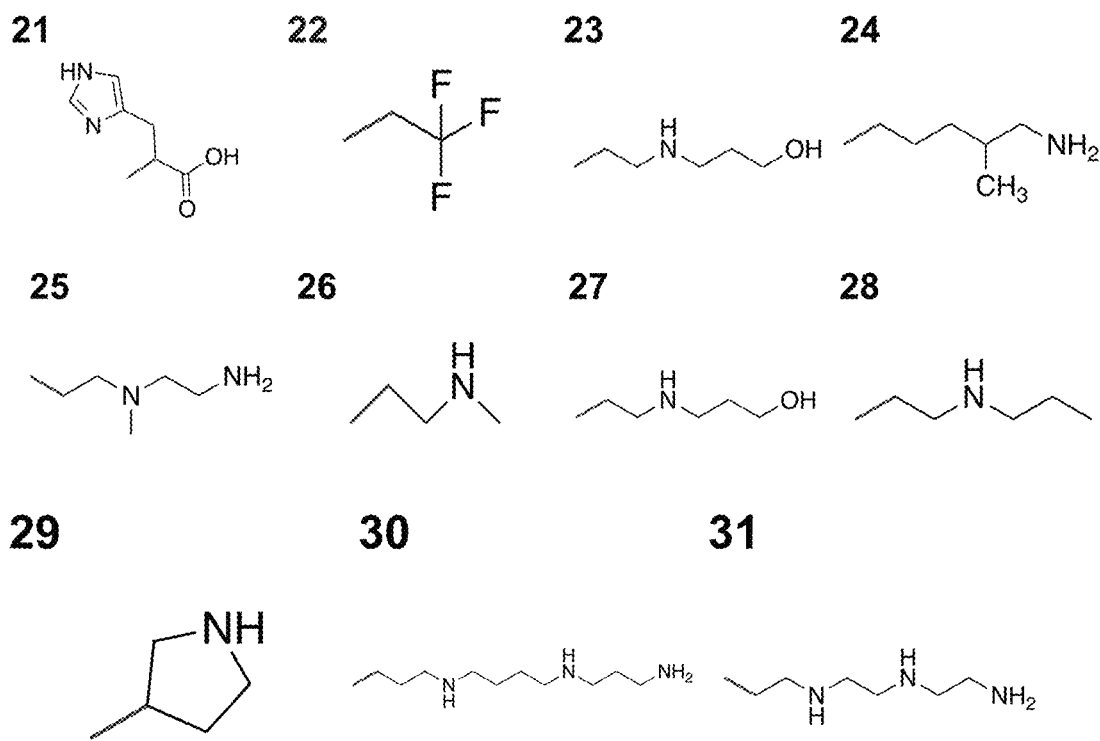

In some forms, $R_3$, $R_4$ or both are selected from the groups shown in FIG. 1.

In some forms, the polymer has a structure of Formula III.

Formula III

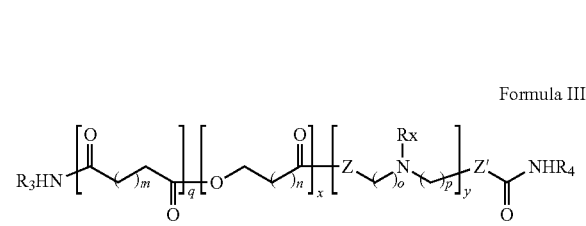

The monomer units can be substituted at one or more positions with one or more substituents. Exemplary substituents include, but are not limited to, alkyl groups, cyclic alkyl groups, alkene groups, cyclic alkene groups, alkynes, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, phosphinate, amino, amido, amidine, imine, cyano, nitro, azido, sulfhydryl, alkylthio, sulfate, sulfonate, sulfamoyl, sulfonamido, sulfonyl, nitro, heterocyclyl, aralkyl, or an aromatic or heteroaromatic moiety.

The polymer is preferably biocompatible. Readily available lactones of various ring sizes are known to possess low toxicity: for example, polyesters prepared from small lactones, such as poly(caprolactone) and poly(p-dioxanone) are commercially available biomaterials which have been used in clinical applications. Large (e.g., $C_{16}$-$C_{24}$) lactones and their polyester derivatives are natural products that have been identified in living organisms, such as bees. Lactones containing ring carbon atoms between 16 and 24 are specifically contemplated and disclosed.

In some forms, the polymers can be further activated via temperature-controlled hydrolysis, thereby exposing one or more activated end group(s). The one or more activated end group(s) can be, for example, hydroxyl or carboxylic acid end groups, both of which can be generated via hydrolysis of ester bonds within the polymers. The activated polymers can have a weight-average molecular weight between about 5 and 25 kDa, preferably between about 5 and 10 kDa. As used herein, the term "about" is meant to minor variations within acceptable parameters. For the sake of clarity, "about" refers to ±10% of a given value. In some forms, the activated polymers contains $R_1$ or $R_2$ at one end, and a hydroxyl or carboxylic acid end group at the other end, generated via hydrolysis.

In some forms, the polymer has a structure of Formula IV.

Formula IV

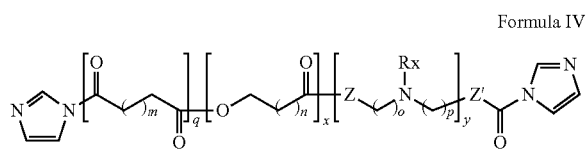

In some forms, the polymer has a structure of Formula V.

Formula V

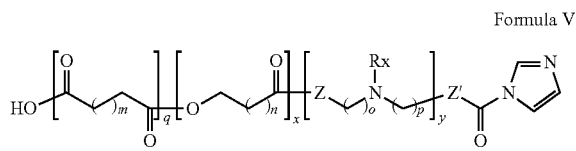

In some forms, the polymer has a structure of Formula VI.

Formula VI

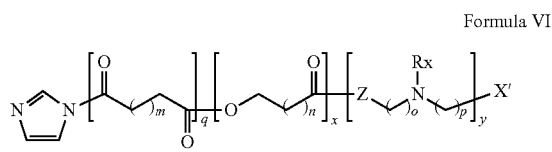

wherein X' is —OH or —NHR'.

Formulas VI, V, and VI are structures of intermediary products. They can be used to synthesize a wide variety of polymers with a structure of Formula I, II or III.

B. Methods of Making the Polymers

The polymers are generally modified from synthetic polymers. Exemplary synthetic polymers include poly(amine-co-ester), formed of a lactone, a dialkyl acid, and a dialkyl amine Methods for the synthesis of poly(amine-co-ester) from a lactone, a dialkyl acid, and a dialkyl amine using an enzyme catalyst, such as a lipase, are also provided. Exemplary lactones are disclosed in U.S. Patent Publication No. US20170121454. In some forms, poly(amine-co-ester) is prepared as shown in Scheme 1:

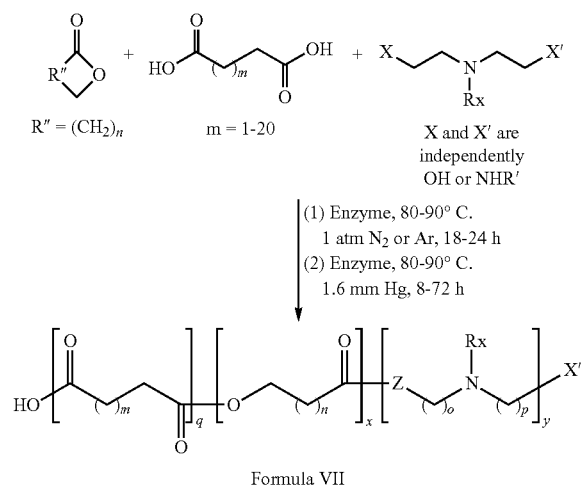

The molar ratio of the monomers (e.g., lactone:aminodiol:diacid) can vary, for example from about 10:90:90 to about 90:10:10. In some embodiments, the ratio is 10:90:90, 20:80:80, 40:60:60, 60:40:40, or 80:20:20. The weight average molecular weight, as determined by GPC using narrow polydispersity polystyrene standards, can vary for example from about 2,000 Daltons to about 50,000 Daltons, preferably from about 2,000 Daltons to about 20,000 Daltons, more preferably from about 5000 Daltons to about 20,000 Daltons, most preferably from about 5000 Daltons to about 10,000 Daltons.

The hydrophobicity of the polymers can be adjusted by varying the percentages of lactone, such as between about 10% and about 100% (calculated lactone unit vs. (lactone unit+diester/diacid)). The molecular weight of the polymers can be adjusted by tuning the second stage reaction time, such as between about 8 and about 72 h.

The enzymatic method allows for the synthesis of polymers with diverse chain structures and tunable hydrophobicities. In some embodiments, the hydrophobicity is varied by varying the ring size and/or molar amount of the lactone monomer. Lactone with a wide range of ring sizes (e.g., $C_4$-$C_{24}$, preferably $C_6$-$C_{24}$, more preferably from $C_6$-$C_{16}$) can be used as comonomers. The reaction can be performed in a single step without protection and deprotection of the amino group(s). Such amino-bearing copolyesters are extremely difficult to prepare using conventional organometallic catalysts, as such catalysts are often sensitive to or deactivated by organic amines. These catalysts are also known to be inefficient for polymerizing large lactone ring monomers. Enzymatic catalysts have distinct advantages for producing biomedical polymers owing to the high activity and selectivity of the enzyme and the resulting high purity of products that are metal-free.

Polymers with a structure of Formula IV, V, or VI can be synthesized via reacting the unmodified polymer of Formula VII with 1,1'-carbonyldiimidazole (CDI), at a molar ratio from about 1:10 to about 1:60, preferably at about 1:40.

Polymers with a structure of Formulas I or II can be obtained via modification of the end groups of the unmodified polymer of Formula VII using coupling reactions known in the art. For example, polymers with a structure of Formula III can be synthesized via (1) reacting the unmodified polymer of Formula VII with CDI to obtain a polymer of Formula IV, and (2) reacting the polymer of Formula IV with $R_3$—$NH_2$ and $R_4$—$NH_2$. In some forms, $R_3$, $R_4$, or both are selected from those shown in FIG. 1. Preferably, $R_3$ and $R_4$ are the same.

Alternatively, polymers with a structure of Formula III can be synthesized via (1) reacting the unmodified polymer of Formula VII with CDI to obtain a polymer of Formula V or VI, (2) protecting the —COOH group or the —X' group in the polymer from step (1), (3) reacting the protected polymer from step (2) with $R_4$—$NH_2$ or $R_3$—$NH_2$, (4) deprotecting the —COOH group or the —X' group in the polymer from step (3), and (5) reacting the deprotected polymer from step (4) with $R_3$—$NH_2$ or $R_4$—$NH_2$.

Hydrolysis-mediated activation of the polymers of Formula I, II, or III can be performed in a temperature-controlled manner for up to 30 days or more. The length of hydrolysis may vary depending on the molecular weight of the polymers to be activated. Larger molecular weight polymers (e.g., about 20-25 kDa) are optimally hydrolyzed for longer periods of time, for example, for about 30 to 40 days. Smaller molecular weight polymers (e.g., about 5-7 kDa) are optimally hydrolyzed for shorter periods of time, for example, for about 4 to 10 days.

In some forms, the polymers are hydrolyzed at a temperature from about 30° C. to 42° C., or any in the range of up to about 100° C. The PACE polymers can be hydrolyzed at a temperature from about 35° C. to 40° C., e.g., about 37° C.

In some forms, the polymers are hydrolyzed, for example, at about 1 atm. Higher pressures accelerate the process (e.g., pressures from about 1 to about 100 atm). The rate for the process would be determined by one of skill in the art for the specific formulations being made.

The weight-average molecular weight of the resulting hydrolysis product can vary from about 5 kDa to about 25 kDa, preferably between about 5 and about 10 kDa.

Preferably, one or more of the ester bond in the polymers are hydrolyzed. The hydrolysis product can have $R_1$ or $R_2$ at one end and a carboxyl or a hydroxyl group at the other end, generated via hydrolysis.

III. Microparticles Formed from the Polymers

The polymers can be used to prepare micro- and/or nanoparticles having encapsulated therein one or more therapeutic, diagnostic, or prophylactic agents. The agent can be encapsulated within the particle, dispersed within the polymer matrix that forms the particle, covalently or non-covalently associated with the surface of the particle or combinations thereof.

In other embodiments, the polymer is biocompatible and biodegradable. The nucleic acid(s) encapsulated by and/or associated with the particles can be released through different mechanisms, including diffusion and degradation of the polymeric matrix. The rate of release can be controlled by varying the monomer composition of the polymer and thus the rate of degradation. For example, if simple hydrolysis is the primary mechanism of degradation, increasing the hydrophobicity of the polymer may slow the rate of degradation and therefore increase the time period of release. In all case, the polymer composition is selected such that an effective amount of nucleic acid(s) is released to achieve the desired purpose/outcome.

The polymers can be used to encapsulate, be mixed with, or be ionically or covalently coupled to any of a variety of therapeutic, prophylactic or diagnostic agents. A wide variety of biologically active materials can be encapsulated or incorporated, either for delivery to a site by the polymer, or to impart properties to the polymer, such as bioadhesion, cell attachment, enhancement of cell growth, inhibition of bacterial growth, and prevention of clot formation.

In some forms, the agent to be encapsulated and delivered can be a small molecule agent (i.e., non-polymeric agent having a molecular weight less than 2,000, 1500, 1,000, 750, or 500 Dalton) or a macromolecule (e.g., an oligomer or polymer) such as proteins, peptides, nucleic acids, etc. Suitable small molecule active agents include organic, inorganic, and/or organometallic compounds. The particles can be used for in vivo and/or in vitro delivery of the agent.

Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Compounds with a wide range of molecular weight can be encapsulated, for example, between 100 and 500,000 grams or more per mole. Examples of suitable materials include proteins such as antibodies, receptor ligands, and enzymes, peptides such as adhesion peptides, saccharides and polysaccharides, synthetic organic or inorganic drugs, and nucleic acids. Examples of materials which can be encapsulated include enzymes, blood clotting factors, inhibitors or clot dissolving agents such as streptokinase and tissue plasminogen activator; antigens for immunization; hormones and growth factors; polysaccharides such as heparin; oligonucleotides such as antisense oligonucleotides and ribozymes and retroviral vectors for use in gene therapy. The polymer can also be used to encapsulate cells and tissues.

Exemplary therapeutic agents that can be incorporated into the particles include, but are not limited to. tumor antigens, CD4+ T-cell epitopes, cytokines, chemotherapeutic agents, radionuclides, small molecule signal transduction inhibitors, photothermal antennas, monoclonal antibodies, immunologic danger signaling molecules, other immunotherapeutics, enzymes, antibiotics, antivirals (especially protease inhibitors alone or in combination with nucleosides for treatment of HIV or Hepatitis B or C), anti-parasitics (helminths, protozoans), growth factors, growth inhibitors, hormones, hormone antagonists, antibodies and bioactive fragments thereof (including humanized, single chain, and chimeric antibodies), antigen and vaccine formulations (including adjuvants), peptide drugs, anti-inflammatories, immunomodulators (including ligands that bind to Toll-Like Receptors to activate the innate immune system, molecules that mobilize and optimize the adaptive immune system, molecules that activate or up-regulate the action of cytotoxic T lymphocytes, natural killer cells and helper T-cells, and molecules that deactivate or down-regulate suppressor or regulatory T-cells), agents that promote uptake of the particles into cells (including dendritic cells and other antigen-presenting cells), nutraceuticals such as vitamins, and oligonucleotide drugs (including DNA, RNAs, antisense, aptamers, small interfering RNAs, ribozymes, external guide sequences for ribonuclease P, and triplex forming agents).

Representative anti-cancer agents include, but are not limited to, alkylating agents (such as cisplatin, carboplatin, oxaliplatin, mechlorethamine, cyclophosphamide, chlorambucil, dacarbazine, lomustine, carmustine, procarbazine, chlorambucil and ifosfamide), antimetabolites (such as fluorouracil (5-FU), gemcitabine, methotrexate, cytosine arabinoside, fludarabine, and floxuridine), antimitotics (including taxanes such as paclitaxel and decetaxel and vinca alkaloids such as vincristine, vinblastine, vinorelbine, and vindesine), anthracyclines (including doxorubicin, daunorubicin, valrubicin, idarubicin, and epirubicin, as well as actinomycins such as actinomycin D), cytotoxic antibiotics (including mitomycin, plicamycin, and bleomycin), topoisomerase inhibitors (including camptothecins such as camptothecin, irinotecan, and topotecan as well as derivatives of epipodophyllotoxins such as amsacrine, etoposide, etoposide phosphate, and teniposide), antibodies to vascular endothelial growth factor (VEGF) such as bevacizumab (AVASTIN®), other anti-VEGF compounds; thalidomide (THALOMID®) and derivatives thereof such as lenalidomide (REVLIMID®); endostatin; angiostatin; receptor tyrosine kinase (RTK) inhibitors such as sunitinib (SUTENT®); tyrosine kinase inhibitors such as sorafenib (Nexavar®), erlotinib (Tarceva®), pazopanib, axitinib, and lapatinib; transforming growth factor-α or transforming growth factor-β inhibitors, and antibodies to the epidermal growth factor receptor such as panitumumab (VECTIBIX®) and cetuximab (ERBITUX®).

Exemplary immunomodulatory agents include cytokines, xanthines, interleukins, interferons, oligodeoxynucleotides, glucans, growth factors (e.g., TNF, CSF, GM-CSF and G-CSF), hormones such as estrogens (diethylstilbestrol, estradiol), androgens (testosterone, HALOTESTIN® (fluoxymesterone)), progestins (MEGACE® (megestrol acetate), PROVERA® (medroxyprogesterone acetate)), and corticosteroids (prednisone, dexamethasone, hydrocortisone).

Examples of immunological adjuvants that can be associated with the particles include, but are not limited to, TLR ligands, C-Type Lectin Receptor ligands, NOD-Like Receptor ligands, RLR ligands, and RAGE ligands. TLR ligands can include lipopolysaccharide (LPS) and derivatives thereof, as well as lipid A and derivatives there of including, but not limited to, monophosphoryl lipid A (MPL), glycopyranosyl lipid A, PET-lipid A, and 3-O-desacyl-4'-monophosphoryl lipid A.

The particles may also include antigens and/or adjuvants (i.e., molecules enhancing an immune response). Peptide, protein, and DNA based vaccines may be used to induce immunity to various diseases or conditions. Cell-mediated immunity is needed to detect and destroy virus-infected cells. Most traditional vaccines (e.g. protein-based vaccines) can only induce humoral immunity. DNA-based vaccine represents a unique means to vaccinate against a virus or parasite because a DNA based vaccine can induce both humoral and cell-mediated immunity. In addition, DNA based vaccines are potentially safer than traditional vaccines. DNA vaccines are relatively more stable and more cost-effective for manufacturing and storage. DNA vaccines consist of two major components—DNA carriers (or delivery vehicles) and DNAs encoding antigens. DNA carriers protect DNA from degradation, and can facilitate DNA entry to specific tissues or cells and expression at an efficient level.

Representative diagnostic agents are agents detectable by x-ray, fluorescence, magnetic resonance imaging, radioactivity, ultrasound, computer tomography (CT) and positron emission tomography (PET). Ultrasound contrast agents are typically a gas such as air, oxygen or perfluorocarbons. Exemplary diagnostic agents include paramagnetic molecules, fluorescent compounds, magnetic molecules, and radionuclides, and x-ray imaging agents.

In some embodiments, particles produced using the methods described here in contain less than 80%, less then 75%, less than 70%, less than 60%, less than 50% by weight, less than 40% by weight, less than 30% by weight, less than 20% by weight, less than 15% by weight, less than 10% by weight, less than 5% by weight, less than 1% by weight, less than 0.5% by weight, or less than 0.1% by weight of the agent. In some embodiments, the agent may be a mixture of pharmaceutically active agents. The percent loading is dependent on a variety of factors, including the agent to be encapsulated, the polymer used to prepare the particles, and the method used to prepare the particles.

The particles may provide controlled release of the drug. For example, the unaltered particles may provide release of an effective amount of the drug over time based on the rate of diffusion of the drug form the particle and/or the rate of degradation of the polymer. The polymer composition can be varied to manipulate the degradation behavior of the polymer and thus the release rate/time of the agent to be delivered. Alternatively, the particle can be coated with one or more materials to provide controlled release, such as sustained release or delayed release of the agent or agents to be delivered.

Sustained release and delayed release materials are well known in the art. Solid esters of fatty acids, which are hydrolyzed by lipases, can be spray coated onto microparticles or drug particles. Zein is an example of a naturally water-insoluble protein. It can be coated onto drug containing microparticles or drug particles by spray coating or by wet granulation techniques. In addition to naturally water-insoluble materials, some substrates of digestive enzymes can be treated with cross-linking procedures, resulting in the formation of non-soluble networks. Many methods of cross-linking proteins, initiated by both chemical and physical means, have been reported. One of the most common methods to obtain cross-linking is the use of chemical cross-linking agents. Examples of chemical cross-linking agents include aldehydes (gluteraldehyde and formaldehyde), epoxy compounds, carbodiimides, and genipin. In addition to these cross-linking agents, oxidized and native sugars have been used to cross-link gelatin. Cross-linking can also be accomplished using enzymatic means; for example, transglutaminase has been approved as a GRAS substance for cross-linking seafood products. Finally, cross-linking can be initiated by physical means such as thermal treatment, UV irradiation and gamma irradiation.

To produce a coating layer of cross-linked protein surrounding drug containing microparticles or drug particles, a water-soluble protein can be spray coated onto the microparticles and subsequently cross-linked by the one of the methods described above. Alternatively, drug-containing microparticles can be microencapsulated within protein by coacervation-phase separation (for example, by the addition of salts) and subsequently cross-linked. Some suitable proteins for this purpose include gelatin, albumin, casein, and gluten.

Polysaccharides can also be cross-linked to form a water-insoluble network. For many polysaccharides, this can be accomplished by reaction with calcium salts or multivalent cations, which cross-link the main polymer chains. Pectin, alginate, dextran, amylose and guar gum are subject to cross-linking in the presence of multivalent cations. Complexes between oppositely charged polysaccharides can also be formed; pectin and chitosan, for example, can be complexed via electrostatic interactions.

Controlled release polymers known in the art include acrylic acid and methacrylic acid copolymers, methyl methacrylate, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamine copolymer poly(methyl methacrylate), poly(methacrylic acid)(anhydride), polymethacrylate, polyacrylamide, poly(methacrylic acid anhydride), and glycidyl methacrylate copolymers.

In certain preferred embodiments, the acrylic polymer is comprised of one or more ammonio methacrylate copolymers Ammonio methacrylate copolymers are well known in the art, and are described in NF XVII as fully polymerized copolymers of acrylic and methacrylic acid esters with a low content of quaternary ammonium groups.

In one preferred embodiment, the acrylic polymer is an acrylic resin lacquer such as that which is commercially available from Rohm Pharma under the tradename EUDRAGIT®. In further preferred embodiments, the acrylic polymer comprises a mixture of two acrylic resin lacquers commercially available from Rohm Pharma under the tradenames EUDRAGIT® RL30D and EUDRAGIT® RS30D, respectively. EUDRAGIT® RL30D and EUDRAGIT® RS30D are copolymers of acrylic and methacrylic esters with a low content of quaternary ammonium groups, the molar ratio of ammonium groups to the remaining neutral (meth)acrylic esters being 1:20 in EUDRAGIT® RL30D and 1:40 in EUDRAGIT® RS30D. The mean molecular weight is about 150,000. EUDRAGIT® S-100 and EUDRAGIT® L-100 are also preferred. The code designations RL (high permeability) and RS (low permeability) refer to the permeability properties of these agents. EUDRAGIT® RL/RS mixtures are insoluble in water and in digestive fluids. However, multiparticulate systems formed to include the same are swellable and permeable in aqueous solutions and digestive fluids.

The polymers such as EUDRAGIT® RL/RS may be mixed together in any desired ratio in order to ultimately obtain a sustained-release formulation having a desirable dissolution profile. Desirable sustained-release multiparticulate systems may be obtained, for instance, from 100% EUDRAGIT®RL, 50% EUDRAGIT®RL and 50% EUDRAGIT® RS, AND 10% EUDRAGIT® RL and 90% EUDRAGIT®RS. One skilled in the art will recognize that other acrylic polymers may also be used, such as, for example, EUDRAGIT®L.

Other controlled release materials include methyl acrylate-methyl methacrylate, polyvinyl chloride, and polyethylene. Hydrophilic polymers include, but are not limited to, cellulosic polymers such as methyl and ethyl cellulose, hydroxyalkylcelluloses such as hydroxypropyl-cellulose, hydroxypropylmethylcellulose, sodium carboxymethylcellulose, and Carbopol® 934, polyethylene oxides and mixtures thereof. Fatty compounds include, but are not limited to, various waxes such as carnauba wax and glyceryl tristearate and wax-type substances including hydrogenated castor oil or hydrogenated vegetable oil, or mixtures thereof.

Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename EUDRAGIT® (Rohm Pharma; Westerstadt, Germany), including EUDRAGIt® L30D-55 and L100-55 (soluble at pH 5.5 and above), EUDRAGIT® L-100 (soluble at pH 6.0 and above), EUDRAGIT® S (soluble at pH 7.0 and above, as a result of a higher degree of esterification), and EUDRAGITS® NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac.

A. Compositions for Transfection of Polynucleotides

It has been discovered that the gene delivery ability of polycationic polymers is due to multiple factors, including polymer molecular weight, hydrophobicity, and charge density. Many synthetic polycationic materials have been tested as vectors for non-viral gene delivery, but almost all are ineffective due to their low efficiency or high toxicity. Most polycationic vectors described previously exhibit high charge density, which has been considered a major requirement for effective DNA condensation. As a result, they are able to deliver genes with high efficiency in vitro but are limited for in vivo applications because of toxicity related to the excessive charge density.

High molecular weight polymers, particularly terpolymers, and methods of making them using enzyme-catalyzed copolymerization of a lactone with a dialkyl diester and an amino diol are disclosed. These poly(amine-co-ester) terpolymers have a low charge density. In addition, their hydrophobicity can be varied by selecting a lactone comonomer with specific ring size and by adjusting lactone content in the polymers. High molecular weight and increased hydrophobicity of the lactone-diester-amino diol terpolymers compensate for the low charge density to provide efficient gene delivery with minimal toxicity.

In preferred embodiments, the terpolymers exhibit efficient gene delivery with reduced toxicity. The terpolymers can be significantly more efficient the commercially available non-viral vectors. For examples, the terpolymers can be more than 100× more efficient than commercially available non-viral vectors such as PEI and LIPOFECTAMINE® 2000 based on luciferase expression assay while exhibiting minimal toxicity at doses of up to 0.5 mg/ml toxicity compared to these commercially available non-viral vectors. Preferably, the terpolymer is non-toxic at concentrations suitable for both in vitro and in vivo transfection of nucleic acids. For example, in some embodiments, the terpolymers cause less non-specific cell death compared to other approaches of cell transfection.

As described in more detail below, in some embodiments, the terpolymer is w-pentadecalactone-diethyl sebacate-N-methyldiethanolamine terpolymer containing 20% PDL (also referred to as terpolymer 111-20% PDL).

IV. Micelles Formed from the Polymers

A. Micelle Properties

1. Micelle Size

The polymers, such as PEG-block containing polymers, can be used to prepare micelles. The average micelle size is typically in the range from about 100 to about 500 nm, preferably from about 100 to about 400 nm, more preferably from about 100 to about 300 nm, more preferably from about 150 to about 200 nm, most preferably from about 160 to about 190 nm, which were stable at physiological pH of 7.4 in the presence of serum proteins. The copolymers possess high blood compatibility and exhibit minimal activity to induce hemolysis and agglutination.

2. Surface Charge

Figure 5A:
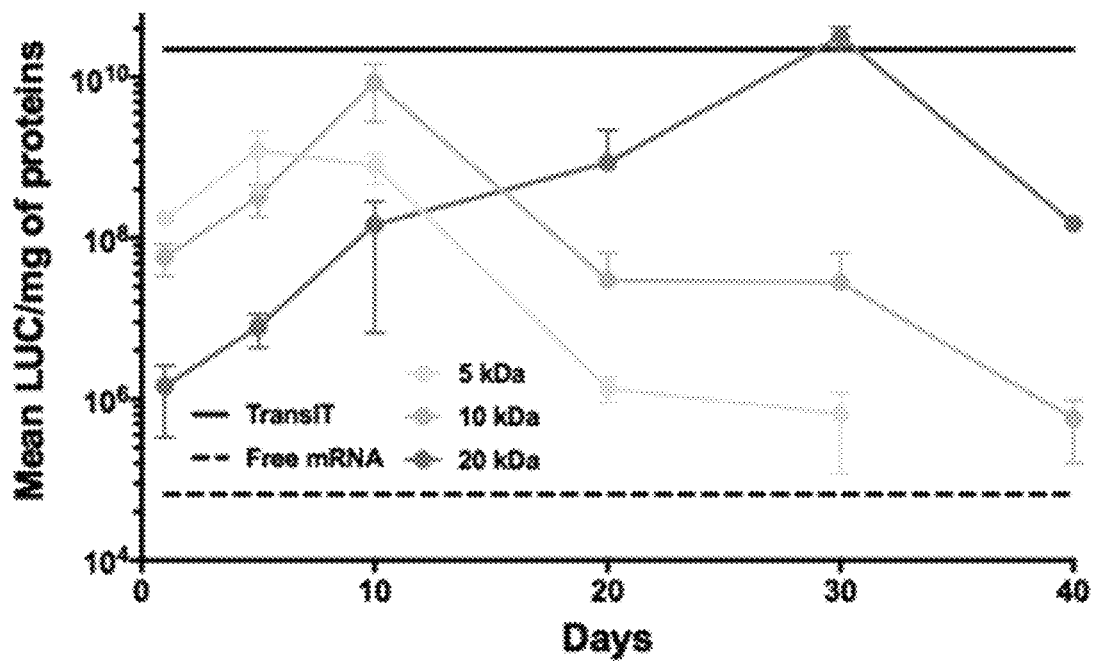
FIG. 5A is a line graph showing Luciferase mRNA transfection efficiency (Mean LUC/mg proteins) depending on the actuation time (days) demonstrating a preferred actuation time for each MW (lines identified as 20 kDa—bottom data point at 0 days; 10 kDa middle data point at 0 days; 5 kDa—top data point at 0 days).

The size and zeta potential of the micelles were found to change significantly when the pH of the aqueous medium accommodating the micelles was varied. For example, the trends in the size-pH and zeta-pH curves are remarkably similar for the micelles of the three PEG2K-PPMS copolymers with different PDL contents (11%, 30%, and 51%). It is evident that the average size of the micelle samples gradually increases upon decreasing the medium pH from 7.4 to 5.0, and then remains nearly constant when the pH value is below 5.0. This pH-responsive behavior observed for the micelles is expected upon decreasing the pH from 7.4 to 5.0, the PPMS cores of the micelles become protonated and more hydrophilic, thus absorbing more water molecules from the aqueous medium to cause swelling of the micelles. The micelle cores are already fully protonated at pH of 5.0, and as a result, the sizes of the micelles remain fairly constant with further decreasing of the pH from 5.0. The effects of the PDL content in the PEG2K-PPMS copolymers on the magnitude of the micelle size change between 7.4 and 5.0 pH values are also notable. With decreasing PDL content and increasing tertiary amino group content in the copolymer, the capacity of the micelle cores to absorb protons and water molecules is expected to increase. Thus, upon decreasing pH from 7.4 to 5.0, the change in average micelle size was more significant for PEG2K-PPMS-11% PDL (from 200 nm to 234 nm) as compared to PEG2K-PPMS-30% PDL (from 184 nm to 214 nm) and PEG2K-PPMS-51% PDL (from 163 nm to 182 nm) (FIG. 5A).

The zeta potential of the micelles in aqueous medium also exhibits substantial pH-dependence. At physiological and alkaline pH (7.4 to 8.5), the surface charges of blank PEG2K-PPMS copolymer micelles were negative, which changed to positive when the pH of the medium decreased to acidic range (4.0-6.0). For example, the micelles of PEG2K-PPMS-11% PDL, PEG2K-PPMS-30% PDL, and PEG2K-PPMS-51% PDL possessed zeta potential values of −5.8, −7.1, −5.1 mV, respectively, at pH of 7.4, which turned to +7.6, +5.8, +4.0 mV, correspondingly, at a lower pH of 5.0. On the basis of the above discussions, this surface charge dependence on pH is attributable to the protonation or deprotonation of the PPMS cores of the micelles at different medium pH. At an alkaline pH (7.4-8.5), most of the amino groups in the micelles presumably are not protonated, and the micelle particles remain negatively charged due to the absorption of HPO42- and/or H2PO4-anions in PBS by the micelles. In particular, at pH of 8.5, the zeta-potential values were −8.1 mV, −7.9 mV, −9.0 mV for PEG2K-PPMS-11% PDL, PEG2K-PPMS-30% PDL, and PEG2K-PPMS-51% PDL, respectively. Upon decreasing pH from 7.4 to 5.0, the tertiary amino moieties in the micelle PPMS cores become mostly protonated, turning the micelles to positively charged particles. Consistently, among the three micelle samples, PEG2K-PPMS-11% PDL micelles with the largest capacity to absorb protons displayed the highest zeta potential values at pH of 4.0-5.0, whereas PEG2K-PPMS-51% PDL micelles with the smallest protonation capacity showed the lowest zeta potentials. The observed micelle surface charge responses to the medium pH are highly desirable since the negative surface charge of the micelles at physiological pH can alleviate the interaction of the micelles with serum protein in the blood and prolong their in vivo circulation time. On the other hand, the reverse to positive surface charge at the tumor extracellular pH of approximately 6.5 could enhance the uptake of these micelles by target tumor cells.

The surface charge of the particles/micelles were slightly negative in PBS solution (0.01M, pH=7.4), which are beneficial for in vivo drug delivery applications of the micelles. It is known that nanoparticles with nearly neutral surface charge (zeta potential between −10 and +10 mV) can decrease their uptake by the reticuloendothelial system (RES) and prolong their circulation time in the blood. The negative surface charges of the micelles could result from the absorption of $HPO_4^{2-}$ and/or $H_2PO_4^-$ anions in PBS by the micelle particles via hydrogen bonding interactions between the anions and the ether groups of PEG shells or the amino groups of PPMS cores. For amphiphilic block copolymer micelles, it is anticipated that hydrophilic chain segments (e.g., PEG) in the outer shell of the micelles can shield the charges in the micelle core with the long chain blocks being more effective in reducing zeta potential than the short chain blocks. Thus, significantly lower zeta potential values were observed for PEGS K-PPMS copolymer micelles as compared to PEG2K-PPMS copolymer micelles.

The copolymer micelles are pH-responsive: decreasing the medium pH from 7.4 to 5.0, the sizes of the micelles significantly increased micelle size while the micelle surface charges reversed from negative charges to positive charges. Correspondingly, DTX-encapsulated copolymer micelles showed gradual sustained drug release at pH of 7.4, but remarkably accelerated DTX release at acidic pH of 5.0. This phenomenon can be exploited to improve release of agents at tumor site, since it is known that the tumor microenvironment is typically weakly acidic (e.g., 5.7-7.0) as the result of lactic acid accumulation due to poor oxygen perfusion. In contrast, the extracellular pH of the normal tissue and blood is slightly basic (pH of 7.2-7.4). Thus, enhanced drug delivery efficiency is anticipated for anticancer drug-loaded micelles that are pH-responsive and can be triggered by acidic pH to accelerate the drug release. Furthermore, even more acidic conditions (pH=4.0-6.0) are encountered in endosomes and lysosomes after uptake of the micelles by tumor cells via endocytosis pathways, which may further increase the cytotoxicity of the drug-encapsulated micelles.

V. Therapeutic, Prophylactic and Diagnostic Agents

The polymers can form various polymer compositions, which are useful for preparing a variety of biodegradable medical devices and for drug delivery. Devices prepared from the PHA copolymers can be used for a wide range of different medical applications. Examples of such applications include controlled release of therapeutic, prophylactic or diagnostic agents; drug delivery; tissue engineering scaffolds; cell encapsulation; targeted delivery; biocompatible coatings; biocompatible implants; guided tissue regeneration; wound dressings; orthopedic devices; prosthetics and bone cements (including adhesives and/or structural fillers); and diagnostics.

The polymers can be used to encapsulate, be mixed with, or be ionically or covalently coupled to any of a variety of therapeutic, prophylactic or diagnostic agents. A wide variety of biologically active materials can be encapsulated or incorporated, either for delivery to a site by the polymer, or to impart properties to the polymer, such as bioadhesion, cell attachment, enhancement of cell growth, inhibition of bacterial growth, and prevention of clot formation.

Examples of suitable therapeutic and prophylactic agents include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. Compounds with a wide range of molecular weight can be encapsulated, for example, between 100 and 500,000 grams or more per mole. Examples of suitable materials include proteins such as antibodies, receptor ligands, and enzymes, peptides such as adhesion peptides, saccharides and polysaccharides, synthetic organic or inorganic drugs, and nucleic acids. Examples of materials which can be encapsulated include enzymes, blood clotting factors, inhibitors or clot dissolving agents such as streptokinase and tissue plasminogen activator; antigens for immunization; hormones and growth factors; polysaccharides such as heparin; oligonucleotides such as antisense oligonucleotides and ribozymes and retroviral vectors for use in gene therapy. The polymer can also be used to encapsulate cells and tissues. Representative diagnostic agents are agents detectable by x-ray, fluorescence, magnetic resonance imaging, radioactivity, ultrasound, computer tomography (CT) and positron emission tomography (PET). Ultrasound diagnostic agents are typically a gas such as air, oxygen or perfluorocarbons. In a preferred embodiment, the polymers are used for delivery of nucleic acids.

A. Polynucleotides

As discussed in more detail below, the terpolymers can be used to transfect cells with nucleic acids. Accordingly, polyplexes including terpolymers and one or more polynucleotides are also disclosed.

The polynucleotide can encode one or more proteins, functional nucleic acids, or combinations thereof. The polynucleotide can be monocistronic or polycistronic. In some embodiments, polynucleotide is multigenic.

In some embodiments, the polynucleotide is transfected into the cell and remains extrachromosomal. In some embodiments, the polynucleotide is introduced into a host cell and is integrated into the host cell's genome. As discussed in more detail below, the compositions can be used in methods of gene therapy. Methods of gene therapy can include the introduction into the cell of a polynucleotide that alters the genotype of the cell. Introduction of the polynucleotide can correct, replace, or otherwise alter the endogenous gene via genetic recombination. Methods can include introduction of an entire replacement copy of a defective gene, a heterologous gene, or a small nucleic acid molecule such as an oligonucleotide. For example, a corrective gene can be introduced into a non-specific location within the host's genome.

In some embodiments, the polynucleotide is incorporated into or part of a vector. Methods to construct expression vectors containing genetic sequences and appropriate transcriptional and translational control elements are well known in the art. These methods include in vitro recombinant DNA techniques, synthetic techniques, and in vivo genetic recombination. Expression vectors generally contain regulatory sequences and necessary elements for the translation and/or transcription of the inserted coding sequence, which can be, for example, the polynucleotide of interest. The coding sequence can be operably linked to a promoter and/or enhancer to help control the expression of the desired gene product. Promoters used in biotechnology are of different types according to the intended type of control of gene expression. They can be generally divided into constitutive promoters, tissue-specific or development-stage-specific promoters, inducible promoters, and synthetic promoters.

For example, in some embodiments, the polynucleotide of interest is operably linked to a promoter or other regulatory elements known in the art. Thus, the polynucleotide can be a vector such as an expression vector. The engineering of polynucleotides for expression in a prokaryotic or eukaryotic system may be performed by techniques generally known to those of skill in recombinant expression. An expression vector typically comprises one of the compositions under the control of one or more promoters. To bring a coding sequence "under the control of" a promoter, one positions the 5' end of the translational initiation site of the reading frame generally between about 1 and 50 nucleotides "downstream" of (i.e., 3' of) the chosen promoter. The "upstream" promoter stimulates transcription of the inserted DNA and promotes expression of the encoded recombinant protein. This is the meaning of "recombinant expression" in the context used here.

Many standard techniques are available to construct expression vectors containing the appropriate nucleic acids and transcriptional/translational control sequences in order to achieve protein or peptide expression in a variety of host-expression systems. Cell types available for expression include, but are not limited to, bacteria, such as E. coli and B. subtilis transformed with recombinant phage DNA, plasmid DNA or cosmid DNA expression vectors. It will be appreciated that any of these vectors may be packaged and delivered using the polymers.

Expression vectors for use in mammalian cells ordinarily include an origin of replication (as necessary), a promoter located in front of the gene to be expressed, along with any necessary ribosome binding sites, RNA splice sites, polyadenylation site, and transcriptional terminator sequences. The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

The promoters may be derived from the genome of mammalian cells (e.g., metallothionein promoter) or from mammalian viruses (e.g., the adenovirus late promoter; the vaccinia virus 7.5K promoter). Further, it is also possible, and may be desirable, to utilize promoter or control sequences normally associated with the desired gene sequence, provided such control sequences are compatible with the host cell systems.

A number of viral based expression systems may be utilized, for example, commonly used promoters are derived from polyoma, Adenovirus 2, cytomegalovirus and Simian Virus 40 (SV40). The early and late promoters of SV40 virus are useful because both are obtained easily from the virus as a fragment which also contains the SV40 viral origin of replication. Smaller or larger SV40 fragments may also be used, provided there is included the approximately 250 bp sequence extending from the HindIII site toward the BglI site located in the viral origin of replication.

In cases where an adenovirus is used as an expression vector, the coding sequences may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing proteins in infected hosts.

Specific initiation signals may also be required for efficient translation of the compositions. These signals include the ATG initiation codon and adjacent sequences. Exogenous translational control signals, including the ATG initiation codon, may additionally need to be provided. One of ordinary skill in the art would readily be capable of determining this need and providing the necessary signals. It is well known that the initiation codon must be in-frame (or in-phase) with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements or transcription terminators.

In eukaryotic expression, one will also typically desire to incorporate into the transcriptional unit an appropriate polyadenylation site if one was not contained within the original cloned segment. Typically, the poly A addition site is placed about 30 to 2000 nucleotides "downstream" of the termination site of the protein at a position prior to transcription termination.

For long-term, high-yield production of recombinant proteins, stable expression is preferred. For example, cell lines that stably express constructs encoding proteins may be engineered. Rather than using expression vectors that contain viral origins of replication, host cells can be transformed with vectors controlled by appropriate expression control elements (e.g., promoter, enhancer, sequences, transcription terminators, polyadenylation sites, etc.), and a selectable marker. Following the introduction of foreign DNA, engineered cells may be allowed to grow for 1-2 days in an enriched medium, and then are switched to a selective medium. The selectable marker in the recombinant plasmid confers resistance to the selection and allows cells to stably integrate the plasmid into their chromosomes and grow to form foci, which in turn can be cloned and expanded into cell lines.

In preferred embodiments, the polynucleotide cargo is an RNA, such as an mRNA. The mRNA can encode a polypeptide of interest.

In some embodiments, the mRNA has a cap on the 5' end and/or a 3' poly(A) tail which can modulate ribosome binding, initiation of translation and stability mRNA in the cell.

B. Polypeptide of Interest

The polynucleotide can encode one or more polypeptides of interest. The polypeptide can be any polypeptide. For example, the polypeptide encoded by the polynucleotide can be a polypeptide that provides a therapeutic or prophylactic effect to an organism or that can be used to diagnose a disease or disorder in an organism. For example, for treatment of cancer, autoimmune disorders, parasitic, viral, bacterial, fungal or other infections, the polynucleotide(s) to be expressed may encode a polypeptide that functions as a ligand or receptor for cells of the immune system, or can function to stimulate or inhibit the immune system of an organism. As discussed in the example below, a polynucleotide encoding TNF-related apoptosis-inducing ligand (TRAIL) can be delivered to tumor cells using the polyplexes in a method of treating cancer.

In some embodiments, the polynucleotide supplements or replaces a polynucleotide that is defective in the organism.

In some embodiments, the polynucleotide includes a selectable marker, for example, a selectable marker that is effective in a eukaryotic cell, such as a drug resistance selection marker. This selectable marker gene can encode a factor necessary for the survival or growth of transformed host cells grown in a selective culture medium. Typical selection genes encode proteins that confer resistance to antibiotics or other toxins, e.g., ampicillin, neomycin, methotrexate, kanamycin, gentamycin, Zeocin, or tetracycline, complement auxotrophic deficiencies, or supply critical nutrients withheld from the media.

In some embodiments, the polynucleotide includes a reporter gene. Reporter genes are typically genes that are not present or expressed in the host cell. The reporter gene typically encodes a protein which provides for some phenotypic change or enzymatic property. Examples of such genes are provided in Weising et al. *Ann. Rev. Genetics*, 22, 421 (1988). Preferred reporter genes include glucuronidase (GUS) gene and GFP genes.

C. Functional Nucleic Acids

The polynucleotide can be, or can encode a functional nucleic acid. Functional nucleic acids are nucleic acid molecules that have a specific function, such as binding a target molecule or catalyzing a specific reaction. Functional nucleic acid molecules can be divided into the following non-limiting categories: antisense molecules, siRNA, miRNA, aptamers, ribozymes, triplex forming molecules, RNAi, and external guide sequences. The functional nucleic acid molecules can act as effectors, inhibitors, modulators, and stimulators of a specific activity possessed by a target molecule, or the functional nucleic acid molecules can possess a de novo activity independent of any other molecules.

Functional nucleic acid molecules can interact with any macromolecule, such as DNA, RNA, polypeptides, or carbohydrate chains. Thus, functional nucleic acids can interact with the mRNA or the genomic DNA of a target polypeptide or they can interact with the polypeptide itself. Often functional nucleic acids are designed to interact with other nucleic acids based on sequence homology between the target molecule and the functional nucleic acid molecule. In other situations, the specific recognition between the functional nucleic acid molecule and the target molecule is not based on sequence homology between the functional nucleic acid molecule and the target molecule, but rather is based on the formation of tertiary structure that allows specific recognition to take place.

Antisense molecules are designed to interact with a target nucleic acid molecule through either canonical or non-canonical base pairing. The interaction of the antisense molecule and the target molecule is designed to promote the destruction of the target molecule through, for example, RNAseH mediated RNA-DNA hybrid degradation. Alternatively the antisense molecule is designed to interrupt a processing function that normally would take place on the target molecule, such as transcription or replication. Antisense molecules can be designed based on the sequence of the target molecule. There are numerous methods for optimization of antisense efficiency by finding the most accessible regions of the target molecule. Exemplary methods include in vitro selection experiments and DNA modification studies using DMS and DEPC. It is preferred that antisense molecules bind the target molecule with a dissociation constant ($K_d$) less than or equal to $10^{-6}$, $10^{-8}$, $10^{-10}$, or $10^{-12}$.

Aptamers are molecules that interact with a target molecule, preferably in a specific way. Typically aptamers are small nucleic acids ranging from 15-50 bases in length that fold into defined secondary and tertiary structures, such as stem-loops or G-quartets. Aptamers can bind small molecules, such as ATP and theophiline, as well as large molecules, such as reverse transcriptase and thrombin. Aptamers can bind very tightly with $K_d$'s from the target molecule of less than $10^{-12}$ M. It is preferred that the aptamers bind the target molecule with a $K_d$ less than $10^{-6}$, $10^{-8}$, $10^{-10}$, or $10^{-12}$. Aptamers can bind the target molecule with a very high degree of specificity. For example, aptamers have been isolated that have greater than a 10,000 fold difference in binding affinities between the target molecule and another molecule that differ at only a single position on the molecule. It is preferred that the aptamer have a $K_d$ with the target molecule at least 10, 100, 1000, 10,000, or 100,000 fold lower than the $K_d$ with a background binding molecule. It is preferred when doing the comparison for a molecule such as a polypeptide, that the background molecule be a different polypeptide.

Ribozymes are nucleic acid molecules that are capable of catalyzing a chemical reaction, either intramolecularly or intermolecularly. It is preferred that the ribozymes catalyze intermolecular reactions. There are a number of different types of ribozymes that catalyze nuclease or nucleic acid polymerase type reactions which are based on ribozymes found in natural systems, such as hammerhead ribozymes. There are also a number of ribozymes that are not found in natural systems, but which have been engineered to catalyze specific reactions de novo. Preferred ribozymes cleave RNA or DNA substrates, and more preferably cleave RNA substrates. Ribozymes typically cleave nucleic acid substrates through recognition and binding of the target substrate with subsequent cleavage. This recognition is often based mostly on canonical or non-canonical base pair interactions. This property makes ribozymes particularly good candidates for target specific cleavage of nucleic acids because recognition of the target substrate is based on the target substrates sequence.

Triplex forming functional nucleic acid molecules are molecules that can interact with either double-stranded or single-stranded nucleic acid. When triplex molecules interact with a target region, a structure called a triplex is formed in which there are three strands of DNA forming a complex dependent on both Watson-Crick and Hoogsteen base-pairing. Triplex molecules are preferred because they can bind target regions with high affinity and specificity. It is preferred that the triplex forming molecules bind the target molecule with a $K_d$ less than $10^{-6}$, $10^{-8}$, $10^{-10}$, or $10^{-12}$.

External guide sequences (EGSs) are molecules that bind a target nucleic acid molecule forming a complex, which is recognized by RNase P, which then cleaves the target molecule. EGSs can be designed to specifically target a RNA molecule of choice. RNAse P aids in processing transfer RNA (tRNA) within a cell. Bacterial RNAse P can be recruited to cleave virtually any RNA sequence by using an EGS that causes the target RNA:EGS complex to mimic the natural tRNA substrate. Similarly, eukaryotic EGS/RNAse P-directed cleavage of RNA can be utilized to cleave desired targets within eukarotic cells. Representative examples of how to make and use EGS molecules to facilitate cleavage of a variety of different target molecules are known in the art.

Gene expression can also be effectively silenced in a highly specific manner through RNA interference (RNAi). This silencing was originally observed with the addition of double stranded RNA (dsRNA) (Fire, et al. (1998) Nature, 391:806-11; Napoli, et al. (1990) Plant Cell 2:279-89; Hannon, (2002) Nature, 418:244-51). Once dsRNA enters a cell, it is cleaved by an RNase III—like enzyme, Dicer, into double stranded small interfering RNAs (siRNA) 21-23 nucleotides in length that contains 2 nucleotide overhangs on the 3' ends (Elbashir, et al. (2001) Genes Dev., 15:188-200; Bernstein, et al. (2001) Nature, 409:363-6; Hammond, et al. (2000) Nature, 404:293-6). In an ATP dependent step, the siRNAs become integrated into a multi-subunit protein complex, commonly known as the RNAi induced silencing complex (RISC), which guides the siRNAs to the target RNA sequence (Nykanen, et al. (2001) Cell, 107:309-21). At some point the siRNA duplex unwinds, and it appears that the antisense strand remains bound to RISC and directs degradation of the complementary mRNA sequence by a combination of endo and exonucleases (Martinez, et al. (2002) Cell, 110:563-74). However, the effect of iRNA or siRNA or their use is not limited to any type of mechanism.

Short Interfering RNA (siRNA) is a double-stranded RNA that can induce sequence-specific post-transcriptional gene silencing, thereby decreasing or even inhibiting gene expression. In one example, an siRNA triggers the specific degradation of homologous RNA molecules, such as mRNAs, within the region of sequence identity between both the siRNA and the target RNA. For example, WO 02/44321 discloses siRNAs capable of sequence-specific degradation of target mRNAs when base-paired with 3' overhanging ends, herein incorporated by reference for the method of making these siRNAs. Sequence specific gene silencing can be achieved in mammalian cells using synthetic, short double-stranded RNAs that mimic the siRNAs produced by the enzyme dicer (Elbashir, et al. (2001) Nature, 411:494 498) (Ui-Tei, et al. (2000) FEBS Lett 479:79-82). siRNA can be chemically or in vitro-synthesized or can be the result of short double-stranded hairpin-like RNAs (shRNAs) that are processed into siRNAs inside the cell. Synthetic siRNAs are generally designed using algorithms and a conventional DNA/RNA synthesizer. Suppliers include Ambion (Austin, Texas), ChemGenes (Ashland, Massachusetts), Dharmacon (Lafayette, Colorado), Glen Research (Sterling, Virginia), MWB Biotech (Esbersberg, Germany), Proligo (Boulder, Colorado), and Qiagen (Vento, The Netherlands). siRNA can also be synthesized in vitro using kits such as Ambion's SILENCER® siRNA Construction Kit.

The production of siRNA from a vector is more commonly done through the transcription of a short hairpin RNAse (shRNAs). Kits for the production of vectors comprising shRNA are available, such as, for example, Imgenex's GENESUPPRESSOR™ Construction Kits and Invitrogen's BLOCK-IT™ inducible RNAi plasmid and lentivirus vectors.

Composition of the Polynucleotides

The polynucleotide can be DNA or RNA nucleotides which typically include a heterocyclic base (nucleic acid base), a sugar moiety attached to the heterocyclic base, and a phosphate moiety which esterifies a hydroxyl function of the sugar moiety. The principal naturally-occurring nucleotides comprise uracil, thymine, cytosine, adenine and guanine as the heterocyclic bases, and ribose or deoxyribose sugar linked by phosphodiester bonds.

The polynucleotide can be composed of nucleotide analogs that have been chemically modified to improve stability, half-life, or specificity or affinity for a target sequence, relative to a DNA or RNA counterpart. The chemical modifications include chemical modification of nucleobases, sugar moieties, nucleotide linkages, or combinations thereof. As used herein "modified nucleotide" or "chemically modified nucleotide" defines a nucleotide that has a chemical modification of one or more of the heterocyclic base, sugar moiety or phosphate moiety constituents. In some embodiments, the charge of the modified nucleotide is reduced compared to DNA or RNA oligonucleotides of the same nucleobase sequence. For example, the oligonucleotide can have low negative charge, no charge, or positive charge. Modifications should not prevent, and preferably enhance, the ability of the oligonucleotides to enter a cell and carry out a function such inhibition of gene expression as discussed above.

Typically, nucleoside analogs support bases capable of hydrogen bonding by Watson-Crick base pairing to standard polynucleotide bases, where the analog backbone presents the bases in a manner to permit such hydrogen bonding in a sequence-specific fashion between the oligonucleotide analog molecule and bases in a standard polynucleotide (e.g., single-stranded RNA or single-stranded DNA). Preferred analogs are those having a substantially uncharged, phosphorus containing backbone.

As discussed in more detail below, in one preferred embodiment, the oligonucleotide is a morpholino oligonucleotide.

1. Heterocyclic Bases

The principal naturally-occurring nucleotides include uracil, thymine, cytosine, adenine and guanine as the heterocyclic bases. The oligonucleotides can include chemical modifications to their nucleobase constituents. Chemical modifications of heterocyclic bases or heterocyclic base analogs may be effective to increase the binding affinity or stability in binding a target sequence. Chemically-modified heterocyclic bases include, but are not limited to, inosine, 5-(1-propynyl) uracil (pU), 5-(1-propynyl) cytosine (pC), 5-methylcytosine, 8-oxo-adenine, pseudocytosine, pseudoisocytosine, 5 and 2-amino-5-(2'-deoxy-.beta.-D-ribofuranosyl)pyridine (2-aminopyridine), and various pyrrolo- and pyrazolopyrimidine derivatives.

2. Sugar Modifications

Polynucleotides can also contain nucleotides with modified sugar moieties or sugar moiety analogs. Sugar moiety modifications include, but are not limited to, 2'-O-aminoetoxy, 2'-O-amonioethyl (2'-OAE), 2'-O-methoxy, 2'-O-methyl, 2-guanidoethyl (2'-OGE), 2'-0,4'-C-methylene (LNA), 2'-O-(methoxyethyl) (2'-OME) and 2'-O—(N-(methyl)acetamido) (2'-OMA). 2'-O-aminoethyl sugar moiety substitutions are especially preferred because they are protonated at neutral pH and thus suppress the charge repulsion between the TFO and the target duplex. This modification stabilizes the C3'-endo conformation of the ribose or dexyribose and also forms a bridge with the i−1 phosphate in the purine strand of the duplex.

The polynucleotide can be a morpholino oligonucleotide. Morpholino oligonucleotides are typically composed of two more morpholino monomers containing purine or pyrimidine base-pairing moieties effective to bind, by base-specific hydrogen bonding, to a base in a polynucleotide, which are linked together by phosphorus-containing linkages, one to three atoms long, joining the morpholino nitrogen of one monomer to the 5' exocyclic carbon of an adjacent monomer. The purine or pyrimidine base-pairing moiety is typically adenine, cytosine, guanine, uracil or thymine. The synthesis, structures, and binding characteristics of morpholino oligomers are detailed in U.S. Pat. Nos. 5,698,685, 5,217,866, 5,142,047, 5,034,506, 5,166,315, 5,521,063, and 5,506,337.

Important properties of the morpholino-based subunits typically include: the ability to be linked in a oligomeric form by stable, uncharged backbone linkages; the ability to support a nucleotide base (e.g. adenine, cytosine, guanine, thymidine, uracil or inosine) such that the polymer formed can hybridize with a complementary-base target nucleic acid, including target RNA, with high $T_m$, even with oligomers as short as 10-14 bases; the ability of the oligomer to be actively transported into mammalian cells; and the ability of an oligomer:RNA heteroduplex to resist RNAse degradation. In some embodiments, oligonucleotides employ morpholino-based subunits bearing base-pairing moieties, joined by uncharged linkages.

3. Internucleotide Linkages

Internucleotide bond refers to a chemical linkage between two nucleoside moieties. Modifications to the phosphate backbone of DNA or RNA oligonucleotides may increase the binding affinity or stability polynucleotides, or reduce the susceptibility of polynucleotides to nuclease digestion. Cationic modifications, including, but not limited to, diethyl-ethylenediamide (DEED) or dimethyl-aminopropylamine (DMAP) may be especially useful due to decrease electrostatic repulsion between the oligonucleotide and a target. Modifications of the phosphate backbone may also include the substitution of a sulfur atom for one of the non-bridging oxygens in the phosphodiester linkage. This substitution creates a phosphorothioate internucleoside linkage in place of the phosphodiester linkage. Oligonucleotides containing phosphorothioate internucleoside linkages have been shown to be more stable in vivo.

Examples of modified nucleotides with reduced charge include modified internucleotide linkages such as phosphate analogs having achiral and uncharged intersubunit linkages (e.g., Sterchak, et al., Organic Chem., 52:4202, (1987)), and uncharged morpholino-based polymers having achiral inter-subunit linkages (see, e.g., U.S. Pat. No. 5,034,506), as discussed above. Some internucleotide linkage analogs include morpholidate, acetal, and polyamide-linked heterocycles.

In another embodiment, the oligonucleotides are composed of locked nucleic acids. Locked nucleic acids (LNA) are modified RNA nucleotides (see, for example, Braasch, et al., Chem. Biol., 8(1):1-7 (2001)). LNAs form hybrids with DNA which are more stable than DNA/DNA hybrids, a property similar to that of peptide nucleic acid (PNA)/DNA hybrids. Therefore, LNA can be used just as PNA molecules would be. LNA binding efficiency can be increased in some embodiments by adding positive charges to it. Commercial nucleic acid synthesizers and standard phosphoramidite chemistry are used to make LNAs.

In some embodiments, the oligonucleotides are composed of peptide nucleic acids. Peptide nucleic acids (PNAs) are synthetic DNA mimics in which the phosphate backbone of the oligonucleotide is replaced in its entirety by repeating N-(2-aminoethyl)-glycine units and phosphodiester bonds are typically replaced by peptide bonds. The various heterocyclic bases are linked to the backbone by methylene carbonyl bonds. PNAs maintain spacing of heterocyclic bases that is similar to conventional DNA oligonucleotides, but are achiral and neutrally charged molecules. Peptide nucleic acids are comprised of peptide nucleic acid monomers.

Other backbone modifications include peptide and amino acid variations and modifications. Thus, the backbone constituents of oligonucleotides such as PNA may be peptide linkages, or alternatively, they may be non-peptide peptide linkages. Examples include acetyl caps, amino spacers such as 8-amino-3,6-dioxaoctanoic acid (referred to herein as 0-linkers), amino acids such as lysine are particularly useful if positive charges are desired in the PNA, and the like. Methods for the chemical assembly of PNAs are well known. See, for example, U.S. Pat. Nos. 5,539,082, 5,527, 675, 5,623,049, 5,714,331, 5,736,336, 5,773,571, and 5,786, 571.

Polynucleotides optionally include one or more terminal residues or modifications at either or both termini to increase stability, and/or affinity of the oligonucleotide for its target. Commonly used positively charged moieties include the amino acids lysine and arginine, although other positively charged moieties may also be useful. For example, lysine and arginine residues can be added to a bis-PNA linker or can be added to the carboxy or the N-terminus of a PNA strand. Polynucleotides may further be modified to be end capped to prevent degradation using a 3' propylamine group. Procedures for 3' or 5' capping oligonucleotides are well known in the art.

VI. Coating Agents for Polyplexes

Efficiency of polynucleotide delivery using the polymers can be affected by the positive charges on the polyplex surface. For example, a zeta potential of the polyplex of +8.9 mV can attract and bind with negatively charged plasma proteins in the blood during circulation and lead to rapid clearance by the reticuloendothelial system (RES). Efficiency can also be affected by instability of the polyplex nanoparticles. For example, as discussed in the Examples below, polyplex particles incubated in NaAc buffer solution containing 10% serum nearly doubled in size within 15 minutes and increased by over 10-fold after 75 minutes. As a result of this increase in size, enlarged polyplexes might be cleared from the circulation by uptake in the liver. Therefore, in some embodiments the polyplexes are treated or coated to improve polynucleotide delivery efficiency. In some embodiments, the coating improves cell specific targeting of the polyplex, improves the stability (i.e., stabilizes the size of the polyplex in vivo), increases the half-life of the polyplex in vivo (i.e., in systemic circulation), or combinations thereof compared to a control. In some embodiments, the control is a polyplex without a coating.

An exemplary polyplex coating for targeting tumor cells is polyE-mRGD. As used herein, polyE-mRGD refers to a synthetic peptide containing three segments: a first segment including a polyglutamic acid (polyE) stretch, which is negatively charged at physiological pH and, therefore, capable of electrostatic binding to the positively charged surface of the polyplexes; a second segment including a neutral polyglycine stretch, which serves as a neutral linker; and a third segment that includes a RGD sequence that binds the tumor endothelium through the interaction of RGD with $\alpha_v\beta_3$ and $\alpha_v\beta_5$.

As discussed in more detail below, the polyE-mRGD used in the Examples reversed the surface charge of 111-20% PDL/pLucDNA polyplex. When polyE-mRGD was added at 5:1 peptide/DNA weight ratio, the zeta potential of the polyplex changed from +8.9 mV to −5.8 mV. Peptide coated polyplexes were stable upon incubation in NaAc buffer containing 10% serum and resistant to aggregation indicating that the modified polyplexes can escape clearance by RES during circulation in vivo.

In one embodiment, polyE-mRGD includes the sequence EEEEEEEEEEEEEEEGGGGGGRGDK (SEQ ID NO:1), or RGDKGGGGGG EEEEEEEEEEEEEEE (SEQ ID NO:2), or a variant thereof with 85%, 90%, 95%, or more than 95% sequence identity to SEQ ID NO:1 or 2.

Another exemplary coating that can be used to prepare charge neutral, or negatively charged particles that maintain their size in vivo are described in Harris, et al., *Biomaterials*, 31:998-1006 (2010)), and can include the amino acid sequence GGGGGGEEEEEEEEEEEEEEEE (SEQ ID NO:3, poly-E), for non-specific systemic administration, or the amino acids sequence GdPdLGdVdRG-GGGGGG-EE-EEEEEEEEEEEEE-CONH2 (SEQ ID NO:4, poly-E-cat), which contains a polycationic sequence that increase targeting to the spleen, spine, sternum, and femur. In some embodiments, the polypeptide used in the coating is a variant SEQ ID NO:3 or 4, with 85%, 90%, 95%, or more than 95% sequence identity to SEQ ID NO:3 or 4

In vitro studies have indicated that adsorption of immunoglobulin G (IgG) and complement protein C3 to nanoparticles increases their uptake by Kupffer cells and incubation in serum increases hepatic uptake in vivo following liver perfusion (Nagayama, et al., *Int. J. Pharm.*, 342:215-21 (2007)). Reports also indicate that galactose can be used to guide polymeric gene delivery particles to hepatocytes via the asialoglycoprotein receptor (ASGPR (SEQ ID NO:6) (Zhang, et al., *J. Controlled Release*, 102:749-63 (2005)).

A. Compositions for Altering Surface Charge

Polynucleotide delivery efficiency of the polyplexes can be improved by coating the particles with an agent that is negatively charged at physiological pH. Preferably, the negatively charged agent is capable of electrostatic binding to the positively charged surface of the polyplexes. The negatively charged agent can neutralize the charge of the polyplex, or reverse the charge of the polyplex. Therefore, in some embodiments, the negatively charged agent imparts a net negative charge to the polyplex.

In some embodiments, the negatively charged agent is a negatively charged polypeptide. For example, the polypeptide can include aspartic acids, glutamic acids, or a combination therefore, such that the overall charge of the polypeptide is a negative at neutral pH. In some embodiments, the polypeptide is a poly aspartic acid polypeptide consisting of 3, 4, 5, 6, 7, 8, 9, 10, 11, 12, 13, 14, 15, 16, 17, 18, 19, 20, or more than 20 aspartic acid residues. In some embodiments, the polypeptide is a poly glutamic acid polypeptide consisting of 3, 4, 5, 6, 7, 8, 9, 10, 11, 12, 13, 14, 15, 16, 17, 18, 19, 20, or more than 20 glutamic acid residues. Other negatively charged molecules include small molecules (i.e., MW less than 1500, 100, 750, or 500 Daltons) such as hyaluronic acid.

Increasing the negative charge on the surface of the particle can reduce or prevent the negative interactions described above, wherein more positively charged particles attract and bind negatively charged plasma proteins in the blood during circulation and lead to rapid clearance by the reticuloendothelial system (RES). In some embodiments, the zeta potential of the particles is from about −15 mV to about 10 mV, preferably from about −15 mV to about 8 mV, more preferably from about −10 mV to about 8 mV, more preferably from about −8 mV to about 8 mV. The zeta potential can be more negative or more positive than the ranges above provided the particles are stable (i.e., don't aggregate, etc.) and not readily cleared from the blood stream The zeta potential can be manipulated by coating or functionalizing the particle surface with one or more moieties which varies the surface charge. Alternatively, the monomers themselves can be functionalized and/or additional monomers can be introduced into the polymer, which vary the surface charge.

B. Targeting Moieties

In some embodiments, the polyplexes include a cell-type or cell-state specific targeting domain or targeting signal. Examples of moieties which may be linked or unlinked to the polyplexes include, for example, targeting moieties which provide for the delivery of molecules to specific cells. The targeting signal or sequence can be specific for a host, tissue, organ, cell, organelle, non-nuclear organelle, or cellular compartment. For example, the compositions herein can be modified with galactosyl-terminating macromolecules to target the compositions to the liver or to liver cells. The modified compositions selectively enter hepatocytes after interaction of the carrier galactose residues with the asialoglycoprotein receptor present in large amounts and high affinity only on these cells. Moreover, the compositions here can be targeted to other specific intercellular regions, compartments, or cell types.

In one embodiment, the targeting signal binds to its ligand or receptor which is located on the surface of a target cell such as to bring the vector and cell membranes sufficiently close to each other to allow penetration of the vector into the cell. Additional embodiments of the present disclosure are directed to specifically delivering polynucleotides to specific tissue or cell types, wherein the polynucleotides can encode a polypeptide or interfere with the expression of a different polynucleotide. The polynucleotides delivered to the cell can encode polypeptides that can enhance or contribute to the functioning of the cell.

The targeting moiety can be an antibody or antigen binding fragment thereof, an antibody domain, an antigen, a T-cell receptor, a cell surface receptor, a cell surface adhesion molecule, a major histocompatibility locus protein, a viral envelope protein and a peptide selected by phage display that binds specifically to a defined cell.

One skilled in the art will appreciate that the tropism of the polyplexes described can be altered by merely changing the targeting signal. It is known in the art that nearly every cell type in a tissue in a mammalian organism possesses some unique cell surface receptor or antigen. Thus, it is possible to incorporate nearly any ligand for the cell surface receptor or antigen as a targeting signal. For example, peptidyl hormones can be used a targeting moieties to target delivery to those cells which possess receptors for such hormones. Chemokines and cytokines can similarly be employed as targeting signals to target delivery of the complex to their target cells. A variety of technologies have been developed to identify genes that are preferentially expressed in certain cells or cell states and one of skill in the art can employ such technology to identify targeting signals which are preferentially or uniquely expressed on the target tissue of interest.

Tumor Targeting

In one embodiment, the targeting signal is used to selectively target tumor cells. Tumor cells express cell surface markers which may only be expressed in the tumor or present in non-tumor cells but preferentially presented in tumor cells. Such markers can be targeted to increase delivery of the polyplexes to cancer cells.

For example, in some embodiments, the targeting moiety is a polypeptide including an arginine-glycine-aspartic acid sequence. For example, the targeting moiety can be an arginine-glycine-aspartic acid-lysine (RGDK, mRGD) other polypeptide that includes the RGD sequence and is capable of binding to tumor endothelium through the interaction of RGD with $\alpha_v\beta_3$ and $\alpha_v\beta_5$. In some embodiments, a targeting moiety includes the polypeptide sequence R/KxxR/K (SEQ ID NO:7), where "x" is any amino acid, and which allows binding to neuropilin-1. Binding with integrins or neuropilin-1 are two approaches for improving tumor-targeted and tissue-penetrating delivery to tumors in vivo. Similar approaches have been reported to facilitate ligand-specific gene delivery in vitro and targeted gene delivery to liver, spleen, and bone marrow in vivo.

Other, exemplary tumor specific cell surface markers include, but are not limited to, alfa-fetoprotein (AFP), C-reactive protein (CRP), cancer antigen-50 (CA-50), cancer antigen-125 (CA-125) associated with ovarian cancer, cancer antigen 15-3 (CA15-3) associated with breast cancer, cancer antigen-19 (CA-19) and cancer antigen-242 associated with gastrointestinal cancers, carcinoembryonic antigen (CEA), carcinoma associated antigen (CAA), chromogranin A, epithelial mucin antigen (MC5), human epithelium specific antigen (HEA), Lewis(a)antigen, melanoma antigen, melanoma associated antigens 100, 25, and 150, mucin-like carcinoma-associated antigen, multidrug resistance related protein (MRPm6), multidrug resistance related protein (MRP41), Neu oncogene protein (C-erbB-2), neuron specific enolase (NSE), P-glycoprotein (mdr1 gene product), multidrug-resistance-related antigen, p170, multidrug-resistance-related antigen, prostate specific antigen (PSA), CD56, NCAM, EGFR, CD44, and folate receptor. In one embodiment, the targeting signal consists of antibodies which are specific to the tumor cell surface markers.

Antibodies

Another embodiment provides an antibody or antigen binding fragment thereof bound to the polyplex acts as the targeting signal. The antibodies or antigen binding fragment thereof are useful for directing the polyplex to a cell type or cell state. In one embodiment, the polyplex is coated with a polypeptide that is an antibody binding domain, for example from a protein known to bind antibodies such as Protein A and Protein G from *Staphylococcus aureus*. Other domains known to bind antibodies are known in the art and can be substituted. The antibody binding domain links the antibody, or antigen binding fragment thereof, to the polyplex.

In certain embodiments, the antibody that serves as the targeting signal is polyclonal, monoclonal, linear, humanized, chimeric or a fragment thereof. Representative antibody fragments are those fragments that bind the antibody binding portion of the non-viral vector and include Fab, Fab', F(ab'), Fv diabodies, linear antibodies, single chain antibodies and bispecific antibodies known in the art.

In some embodiments, the targeting signal includes all or part of an antibody that directs the polyplex to the desired target cell type or cell state. Antibodies can be monoclonal or polyclonal, but are preferably monoclonal. For human gene therapy purposes, antibodies can be derived from human genes and are specific for cell surface markers, and are produced to reduce potential immunogenicity to a human host as is known in the art. For example, transgenic mice which contain the entire human immunoglobulin gene cluster are capable of producing "human" antibodies can be utilized. In one embodiment, fragments of such human antibodies are employed as targeting signals. In a preferred embodiment, single chain antibodies modeled on human antibodies are prepared in prokaryotic culture.

In one embodiment, the targeting signal is directed to cells of the nervous system, including the brain and peripheral nervous system. Cells in the brain include several types and states and possess unique cell surface molecules specific for the type. Furthermore, cell types and states can be further characterized and grouped by the presentation of common cell surface molecules.

In one embodiment, the targeting signal is directed to specific neurotransmitter receptors expressed on the surface of cells of the nervous system. The distribution of neurotransmitter receptors is well known in the art and one so skilled can direct the compositions described by using neurotransmitter receptor specific antibodies as targeting signals. Furthermore, given the tropism of neurotransmitters for their receptors, in one embodiment the targeting signal consists of a neurotransmitter or ligand capable of specifically binding to a neurotransmitter receptor.

In one embodiment, the targeting signal is specific to cells of the nervous system which may include astrocytes, microglia, neurons, oligodendrites and Schwann cells. These cells can be further divided by their function, location, shape, neurotransmitter class and pathological state. Cells of the nervous system can also be identified by their state of differentiation, for example stem cells Exemplary markers specific for these cell types and states are well known in the art and include, but are not limited to CD133 and Neurosphere.

In one embodiment, the targeting signal is directed to cells of the musculoskeletal system. Muscle cells include several types and possess unique cell surface molecules specific for the type and state. Furthermore, cell types and states can be further characterized and grouped by the presentation of common cell surface molecules.

In one embodiment, the targeting signal is directed to specific neurotransmitter receptors expressed on the surface of muscle cells. The distribution of neurotransmitter receptors is well known in the art and one so skilled can direct the compositions described by using neurotransmitter receptor specific antibodies as targeting signals. Furthermore, given the tropism of neurotransmitters for their receptors, in one embodiment the targeting signal consists of a neurotransmitter. Exemplary neurotransmitters expressed on muscle cells that can be targeted include but are not limited to acetycholine and norepinephrine.

In one embodiment, the targeting signal is specific to muscle cells which consist of two major groupings, Type I and Type II. These cells can be further divided by their function, location, shape, myoglobin content and pathological state. Muscle cells can also be identified by their state of differentiation, for example muscle stem cells. Exemplary markers specific for these cell types and states are well known in the art include, but are not limited to MyoD, Pax7, and MR4.

C. Linkers

In some embodiments the polyplex can be coated with both a negatively charged agent and a targeting moiety. In some embodiments, the negatively charged agent and the targeting moiety are linked together by a linker. The linker can be a polypeptide, or any other suitable linker that is known in the art, for example, poly ethylene glycol (PEG).

In some embodiments, the linker is polypeptide that has approximately neutral charge at physiological pH. In some embodiments, the linker polypeptide is a polyglycine. For example, in some embodiments the linker consists of 3, 4, 5, 6, 7, 8, 9, 10, 11, 12, 13, 14, 15, 16, 17, 18, 19, 20, or glycine residues. In a preferred embodiment, the linker is a 6-residue polyglycine.

In some embodiments, the negatively charged agent alone, or in combination with a targeting moiety is linked to the polyplex by electrostatic interactions. In some embodiments, the negative charged agent, the targeting moiety, or a combination thereof is linked to the polyplex by covalent conjugation to the polymer backbone or to a side chain attached to the polymer backbone.

D. Size of Polyplexes and Methods of Reducing Aggregation

Resistance to aggregation can be important because maintaining a small particle size limits clearance by the liver and maintains transfection ability of polyplex particles into target cells. Therefore, in preferred embodiments, the polyplexes are resistant to aggregation. Preferably, polyplexes with or without coating are between about 1 nm and 1000 nm in radius, more preferably between about 1 nm and about 500 nm in radius, most preferably between about 15 nm and about 250 nm in radius. For example, in some embodiments, coated polyplexes loaded with polynucleotide are between about 150 nm and 275 nm in radius.

The ratio of polynucleotide weight to polymer weight (polynucletide:polymer), the content and quantity of polyplex coating, or a combination thereof can be used to adjust the size of the polyplexes.

For example, the Examples below show that in some embodiments, transfection efficiency of particles with 25:1 polymer to DNA ratio is lower than the transfection efficiency of particles with 50:1, 100:1, 150:1, and 200:1 polymer:DNA ratios. The most preferred polymer:polynucleotide ratio for a particular formulation can be determined empirically using the methods that are known in the art, such as those described in the Examples below. Generally, the weight:weight ratio of polymer:polynucleotide is preferably greater than about 10:1, more preferably greater than about 50:1, most preferably greater than about 100:1. The weight:weight ratio of polymer:polynucleotide is preferably between about 10:1 and 500:1, more preferably between about 25:1 and 250:1, most preferably between about 50:1 and 150:1. In some embodiments, the weight ratio of polymer:polynucleotide is about 100:1. Preferably, the polyplexes has are spherical in shape.

The examples also show that in some embodiments, transfection efficiency of particles by the ratio of coating agent molecules to polynucleotide molecules (coating agent:polynucleotide). The ratio is expressed by weight. The most preferred coating agent:polynucleotide ratio for a particular formulation can be determined empirically using the methods that are known in the art, such as those described in the Examples below. Generally, the ratio of coating agent:polynucleotide is greater than 0, and preferably lower than about 50:1, more preferably lower than about 25:1, most preferably lower than about 10:1. The ratio coating agent:polynucleotide is preferably between about 1:1 and 10:1, more preferably between about 2.5:1 and 7.5:1. In some embodiments, the ratio of coating agent:polynucleotide is about 5:1. Ratios of coating agent:polynucleotide of 10:1, 5:1, and 2.5:1 are also referred to herein as 10×, 5×, and 2.5× respectively. Preferably, the polyplexes are spherical in shape.

E. PEG-Blocking Containing Polymers

The polymers can be used for drug delivery, for example, in the formation of particles, such as microparticles or nanoparticles, or micelles which can release one or more therapeutic, prophylactic, and/or diagnostic agents in a controlled release manner over a desirable period of time.

pH-responsive micelle nanocarriers are often formed via self-assembly of amphiphilic block copolymers and consist of a hydrophilic (e.g. PEG) outer shell and a hydrophobic inner core capable of response to medium pH. Typically, upon changing the medium pH from neutral or slightly basic to mildly acidic, the micelle cores undergo accelerated degradation, become completely soluble in water, or swell substantially in aqueous medium. As the result, the drug-encapsulated micelles with a slow drug-release rate at the physiological pH can be triggered by an acidic pH to rapidly unload the drug molecules. The polymer segments constituting the micelle cores in previous reports include poly (ortho esters), poly(β-amino esters), poly(L-histidine), and others. The major disadvantages with most of the previous micelle systems are the multiple steps required for preparing the copolymers and the difficulty of controlling the polymer molecular weight and adjusting the polymer composition during the copolymer synthesis.

The copolymers exhibited variation in the rate of release as a function of pH. In vitro drug release behaviors of the DTX-encapsulated micelles of PEG2K-PPMS copolymer samples (PEG2K-PPMS-11% PDL, PEG2K-PPMS-30% PDL, and PEG2K-PPMS-51% PDL) were studied in PBS solution at both physiological pH of 7.4 and acidic pH of 5.0. In general, the DTX release from all micelle samples followed biphasic release kinetics and exhibited remarkable pH-dependence. The DTX-loaded PEG2K-PPMS copolymer micelles release 25-45% drug rapidly during the initial 12 h, followed by a more gradual release of additional 25-40% drug for the subsequent 132 h. The influence of the medium pH on the drug release rate is substantial. For example, at the end of the incubation period (144 h), the values of accumulated DTX released from the micelles of PEG2K-PPMS-11% PDL, PEG2K-PPMS-30% PDL, and PEG2K-PPMS-51% PDL copolymers are respectively 66%, 60%, and 55% at physiological pH of 7.4, which increase correspondingly to 85%, 81%, and 75% at acidic pH of 5.0. The observed pH-triggered acceleration of DTX release from the PEG2K-PPMS copolymer micelles is consistent with the earlier observation that changing of the medium pH from 7.4 to 5.0 causes significant swelling of the micelles due to the protonation and size increase of the micelle PPMS cores. This pH-triggered micelle size expansion would certainly facilitate the diffusion and release of entrapped DTX from the micelle cores to the aqueous medium. At a given pH, the DTX release rate is presumably controlled by the interactions between the drug and the PPMS matrix in the micelle cores. Since PDL-rich PEG2K-PPMS copolymers are expected to form strong hydrophobic domains in their micelle inner cores to better trap and retain hydrophobic DTX molecules, the drug release from such copolymer micelles should be more gradual and sustained. This hypothesis is supported by the experimental result showing that at both pH of 7.4 and 5.0, the DTX release rate from PEG2K-PPMS copolymer micelles decreases with increasing PDL content in the PPMS chain segments of the copolymer.

It is known that upon uptake of micelles by tumor cells, the micelle particles are subjected to entrapment in endosomes with pH ranging from 5.5 to 6.0 and in lysosomes with pH ranging from 4.5 to 5.0. As the above results clearly show, these acidic environments would inevitably trigger fast DTX release from PEG2K-PPMS copolymer micelles, thus enhancing the cytotoxicity of the drug-loaded micelles. The amino groups in the copolymers would act as proton sponges to facilitate endosomal escape. Therefore, the pH-responsive properties exhibited by the PEG2K-PPMS copolymer micelles are highly desirable, which render them to be superior carriers for delivery of anticancer drugs.

VII. Formulations

Formulations are prepared using a pharmaceutically acceptable "carrier" composed of materials that are considered safe and effective and may be administered to an individual without causing undesirable biological side effects or unwanted interactions. The "carrier" is all components present in the pharmaceutical formulation other than the active ingredient or ingredients. The term "carrier" includes but is not limited to diluents, binders, lubricants, desintegrators, fillers, and coating compositions. For detailed information concerning materials, equipment and processes for preparing tablets and delayed release dosage forms, see Pharmaceutical Dosage Forms: Tablets, eds. Lieberman et al. (New York: Marcel Dekker, Inc., 1989), and Ansel et al., Pharmaceutical Dosage Forms and Drug Delivery Systems, 6.sup.th Ed. (Media, PA: Williams & Wilkins, 1995).

VIII. Methods of Preparing Polyplexes

A. Methods for Making Particles

Particles can be prepared using a variety of techniques known in the art. The technique to be used can depend on a variety of factors including the polymer used to form the nanoparticles, the desired size range of the resulting particles, and suitability for the material to be encapsulated.

Methods known in the art that can be used to prepare nanoparticles include, but are not limited to, polyelectrolyte condensation (see Suk et al., *Biomaterials*, 27, 5143-5150 (2006)); single and double emulsion; nanoparticle molding, and electrostatic self-assembly (e.g., polyethylene imine-DNA or liposomes).

In one embodiment, the loaded particles are prepared by combining a solution of the polymer, typically in an organic solvent, with the polynucleotide of interest. The polymer solution is prepared by dissolving or suspending the polymer in a solvent. The solvent should be selected so that it does not adversely effect (e.g., destabilize or degrade) the nucleic acid to be encapsulated. Suitable solvents include, but are not limited to DMSO and methylene chloride. The concentration of the polymer in the solvent can be varied as needed. In some embodiments, the concentration is for example 25 mg/ml. The polymer solution can also be diluted in a buffer, for example, sodium acetate buffer.

Next, the polymer solution is mixed with the agent to be encapsulated, such as a polynucleotide. The agent can be dissolved in a solvent to form a solution before combining it with the polymer solution. In some embodiments, the agent is dissolved in a physiological buffer before combining it with the polymer solution. The ratio of polymer solution volume to agent solution volume can be 1:1. The combination of polymer and agent are typically incubated for a few minutes to form particles before using the solution for its desired purpose, such as transfection. For example, a polymer/polynucleotide solution can be incubated for 2, 5, 10, or more than 10 minutes before using the solution for transfection. The incubation can be at room temperature.

In some embodiments, the particles are also incubated with a solution containing a coating agent prior to use. The particle solution can be incubated with the coating agent for 2, 5, 10, or more than 10 minutes before using the polyplexes for transfection. The incubation can be at room temperature.

In some embodiments, if the agent is a polynucleotide, the polynucleotide is first complexed to a polycation before mixing with polymer. Complexation can be achieved by mixing the polynucleotides and polycations at an appropriate molar ratio. When a polyamine is used as the polycation species, it is useful to determine the molar ratio of the polyamine nitrogen to the polynucleotide phosphate (N/P ratio). In a preferred embodiment, inhibitory RNAs and polyamines are mixed together to form a complex at an N/P ratio of between approximately 1:1 to 1:25, preferably between about 8:1 to 15:1. The volume of polyamine solution required to achieve particular molar ratios can be determined according to the following formula:

$$V_{NH2} = \frac{C_{inhRNA,final} \times M_{w,inhRNA}/C_{inhRNA,final} \times M_{w,P} \times \Phi_{N:P} \times \Phi V_{final}}{C_{NH2}/M_{w,NH2}}$$

where $M_{w,inhRNA}$=molecular weight of inhibitory RNA, $M_{w,P}$=molecular weight of phosphate groups of inhibitory RNA, $\Phi_{N:P}$=N:P ratio (molar ratio of nitrogens from polyamine to the ratio of phosphates from the inhibitory RNA), $C_{NH2}$, stock=concentration of polyamine stock solution, and $M_{w,NH2}$=molecular weight per nitrogen of polyamine Methods of mixing polynucleotides with polycations to condense the polynucleotide are known in the art. See for example U.S. Published Application No. 2011/0008451.

The term "polycation" refers to a compound having a positive charge, preferably at least 2 positive charges, at a selected pH, preferably physiological pH. Polycationic moieties have between about 2 to about 15 positive charges, preferably between about 2 to about 12 positive charges, and more preferably between about 2 to about 8 positive charges at selected pH values. Many polycations are known in the art. Suitable constituents of polycations include basic amino acids and their derivatives such as arginine, asparagine, glutamine, lysine and histidine; cationic dendrimers; and amino polysaccharides. Suitable polycations can be linear, such as linear tetralysine, branched or dendrimeric in structure.

Exemplary polycations include, but are not limited to, synthetic polycations based on acrylamide and 2-acrylamido-2-methylpropanetrimethylamine, poly(N-ethyl-4-vinylpyridine) or similar quartemized polypyridine, diethylaminoethyl polymers and dextran conjugates, polymyxin B sulfate, lipopolyamines, poly(allylamines) such as the strong polycation poly(dimethyldiallylammonium chloride), polyethyleneimine, polybrene, and polypeptides such as protamine, the histone polypeptides, polylysine, polyarginine and polyornithine.

In some embodiments, the polycation is a polyamine. Polyamines are compounds having two or more primary amine groups. Suitable naturally occurring polyamines include, but are not limited to, spermine, spermidine, cadaverine and putrescine. In a preferred embodiment, the polyamine is spermidine.

In another embodiment, the polycation is a cyclic polyamine Cyclic polyamines are known in the art and are described, for example, in U.S. Pat. No. 5,698,546, WO 1993/012096 and WO 2002/010142. Exemplary cyclic polyamines include, but are not limited to, cyclen.

Spermine and spermidine are derivatives of putrescine (1,4-diaminobutane) which is produced from L-ornithine by action of ODC (ornithine decarboxylase). L-ornithine is the product of L-arginine degradation by arginase. Spermidine is a triamine structure that is produced by spermidine synthase (SpdS) which catalyzes monoalkylation of putrescine (1,4-diaminobutane) with decarboxylated S-adenosylmethionine (dcAdoMet) 3-aminopropyl donor. The formal alkylation of both amino groups of putrescine with the 3-aminopropyl donor yields the symmetrical tetraamine spermine. The biosynthesis of spermine proceeds to spermidine by the effect of spermine synthase (SpmS) in the presence of dcAdoMet. The 3-aminopropyl donor (dcAdoMet) is derived from S-adenosylmethionine by sequential transformation of L-methionine by methionine adenosyltransferase followed by decarboxylation by AdoMetDC (S-adenosylmethionine decarboxylase). Hence, putrescine, spermidine and spermine are metabolites derived from the amino acids L-arginine (L-ornithine, putrescine) and L-methionine (dcAdoMet, aminopropyl donor).

IX. Methods of Using the Particles/Micelles

A. Drug Delivery

The particles can be use to deliver an effective amount of one or more therapeutic, diagnostic, and/or prophylactic agents to a patient in need of such treatment. The amount of agent to be administered can be readily determine by the prescribing physician and is dependent on the age and weight of the patient and the disease or disorder to be treated.

The particles are useful in drug delivery (as used herein "drug" includes therapeutic, nutritional, diagnostic and prophylactic agents), whether injected intravenously, subcutaneously, or intramuscularly, administered to the nasal or pulmonary system, injected into a tumor milieu, administered to a mucosal surface (vaginal, rectal, buccal, sublingual), or encapsulated for oral delivery. The particles may be administered as a dry powder, as an aqueous suspension (in water, saline, buffered saline, etc), in a hydrogel, organogel, or liposome, in capsules, tablets, troches, or other standard pharmaceutical excipient.

B. Transfection

The compositions can be for cell transfection of polynucleotides. As discussed in more detail below, the transfection can occur in vitro or in vivo, and can be applied in applications including gene therapy and disease treatment. The compositions can be more efficient, less toxic, or a combination thereof when compared to a control. In some embodiments, the control is cells treated with an alternative transfection reagent such as LIPOFECTAMINE 2000 or polyethylenimine (PEI).

Transfection is carried out by contacting cells with the solution containing the polyplexes. For in vivo methods, the contacting typically occurs in vivo after the solution is administered to the subject. For in vitro methods, the solution is typically added to a culture of cells and allowed to contact the cells for minutes, hours, or days. The cells can subsequently be washed to move excess polyplexes.

The particular polynucleotide delivered by the polyplex can be selected by one of skill in the art depending on the condition or disease to be treated. The polynucleotide can be, for example, a gene or cDNA of interest, mRNA, a functional nucleic acid such as an inhibitory RNA, a tRNA, an rRNA, or an expression vector encoding a gene or cDNA of interest, a functional nucleic acid a tRNA, or an rRNA. In some embodiments two or more polynucleotides are administered in combination.

The compositions can be used in a method of delivering polynucleotides to cells in vitro. For example, the polyplexes can be used for in vitro transfection of cells. The method typically involves contacting the cells with polyplex including a polynucleotide in an effective amount to introduce the polynucleotide into the cell's cytoplasm. In some embodiments, the polynucleotide is delivered to the cell in an effective amount to change the genotype or a phenotype of the cell. The cells can primary cells isolated from a subject, or cells of an established cell line. The cells can be of a homogenous cell type, or can be a heterogeneous mixture of different cells types. For example, the polyplexes can be introduced into the cytoplasm of cells from a heterogenous cell line possessing cells of different types, such as in a feeder cell culture, or a mixed culture in various states of differentiation. The cells can be a transformed cell line that can be maintained indefinitely in cell culture. Exemplary cell lines are those available from American Type Culture Collection including tumor cell lines.

Any eukaryotic cell can be transfected to produce cells that express a specific nucleic acid, for example a metabolic gene, including primary cells as well as established cell lines. Suitable types of cells include but are not limited to undifferentiated or partially differentiated cells including stem cells, totipotent cells, pluripotent cells, embryonic stem cells, inner mass cells, adult stem cells, bone marrow cells, cells from umbilical cord blood, and cells derived from ectoderm, mesoderm, or endoderm. Suitable differentiated cells include somatic cells, neuronal cells, skeletal muscle, smooth muscle, pancreatic cells, liver cells, and cardiac cells. In another embodiment, siRNA, antisense polynucleotides (including siRNA or antisense polynucleotides) or inhibitory RNA can be transfected into a cell using the compositions.

The methods are particularly useful in the field of personalized therapy, for example, to repair a defective gene, de-differentiate cells, or reprogram cells. For example, target cells are first isolated from a donor using methods known in the art, contacted with the polyplexes including a polynucleotide causing a change to the in vitro (ex vivo), and administered to a patient in need thereof. Sources or cells include cells harvested directly from the patient or an allographic donor. In preferred embodiments, the target cells to be administered to a subject will be autologous, e.g. derived from the subject, or syngenic. Allogeneic cells can also be isolated from antigenically matched, genetically unrelated donors (identified through a national registry), or by using target cells obtained or derived from a genetically related sibling or parent.

Cells can be selected by positive and/or negative selection techniques. For example, antibodies binding a particular cell surface protein may be conjugated to magnetic beads and immunogenic procedures utilized to recover the desired cell type. It may be desirable to enrich the target cells prior to transient transfection. As used herein in the context of compositions enriched for a particular target cell, "enriched" indicates a proportion of a desirable element (e.g. the target cell) which is higher than that found in the natural source of the cells. A composition of cells may be enriched over a natural source of the cells by at least one order of magnitude, preferably two or three orders, and more preferably 10, 100, 200, or 1000 orders of magnitude. Once target cells have been isolated, they may be propagated by growing in suitable medium according to established methods known in the art. Established cell lines may also be useful in for the methods. The cells can be stored frozen before transfection, if necessary.

Next the cells are contacted with the composition in vitro to repair, de-differentiate, re-differentiate, and/or re-program the cell. The cells can be monitored, and the desired cell type can be selected for therapeutic administration.

Following repair, de-differentiation, and/or re-differentiation and/or reprogramming, the cells are administered to a patient in need thereof. In the most preferred embodiments, the cells are isolated from and administered back to the same patient. In alternative embodiments, the cells are isolated from one patient, and administered to a second patient. The method can also be used to produce frozen stocks of altered cells which can be stored long-term, for later use. In one embodiment, fibroblasts, keratinocytes or hematopoietic stem cells are isolated from a patient and repaired, de-differentiated, or reprogrammed in vitro to provide therapeutic cells for the patient.

C. In Vivo Methods

The compositions can be used in a method of delivering polynucleotides to cells in vivo. It has been discovered that the polymers are more efficient and/or less toxic for systemic in vivo transfection of polynucleotides than alternative transfection reagents includes LIPOFECTAMINE 2000, PEI, and even other PMSCs. Accordingly, in some embodiments, the cell specific polyplexes including a therapeutic polynucleotide are administered systemically in vivo to a treat a disease, for example cancer.

In some in vivo approaches, the compositions are administered to a subject in a therapeutically effective amount. As used herein the term "effective amount" or "therapeutically effective amount" means a dosage sufficient to treat, inhibit, or alleviate one or more symptoms of the disorder being treated or to otherwise provide a desired pharmacologic and/or physiologic effect. The precise dosage will vary according to a variety of factors such as subject-dependent variables (e.g., age, immune system health, etc.), the disease, and the treatment being effected.

Pharmaceutical compositions can be for administration by parenteral (intramuscular, intraperitoneal, intravenous (IV) or subcutaneous injection), transdermal (either passively or using iontophoresis or electroporation), or transmucosal (nasal, vaginal, rectal, or sublingual) routes of administration or using bioerodible inserts and can be formulated in dosage forms appropriate for each route of administration.

In some embodiments, the compositions are administered systemically, for example, by intravenous or intraperitoneal administration, in an amount effective for delivery of the compositions to targeted cells. Other possible routes include trans-dermal or oral.

In certain embodiments, the compositions are administered locally, for example by injection directly into a site to be treated. In some embodiments, the compositions are injected or otherwise administered directly to one or more tumors. Typically, local injection causes an increased localized concentration of the compositions which is greater than that which can be achieved by systemic administration. In some embodiments, the compositions are delivered locally to the appropriate cells by using a catheter or syringe. Other means of delivering such compositions locally to cells include using infusion pumps (for example, from Alza Corporation, Palo Alto, Calif.) or incorporating the compositions into polymeric implants (see, for example, P. Johnson and J. G. Lloyd-Jones, eds., Drug Delivery Systems (Chichester, England: Ellis Horwood Ltd., 1987), which can effect a sustained release of the polyplexes to the immediate area of the implant.

The polyplexes can be provided to the cell either directly, such as by contacting it with the cell, or indirectly, such as through the action of any biological process. For example, the polyplexes can be formulated in a physiologically acceptable carrier or vehicle, and injected into a tissue or fluid surrounding the cell. The polyplexes can cross the cell membrane by simple diffusion, endocytosis, or by any active or passive transport mechanism.

The compositions can be used in gene therapy protocols for the treatment of gene related diseases or disorders. Cell dysfunction can also be treated or reduced using the compositions and methods. In some embodiments, diseases amenable to gene therapy are specifically targeted. The disease can be in children, for example individuals less than 18 years of age, typically less than 12 years of age, or adults, for example individuals 18 years of age or more. Thus, embodiments of the present disclosure are directed to treating a host diagnosed with a disease, by transfection of the polyplex including a polynucleotide into the cell affected by the disease and wherein the polynucleotide encodes a therapeutic protein. In another embodiment, an inhibitory RNA is directed to a specific cell type or state to reduce or eliminate the expression of a protein, thereby achieving a therapeutic effect. The present disclosure encompasses manipulating, augmenting or replacing genes to treat diseases caused by genetic defects or abnormalities.

Suitable genetic based diseases that can be treated with the compositions herein include but are not limited to:

Mitochondrial Disease: Alpers Disease; Barth syndrome; (3-oxidation defects; carnitine-acyl-carnitine deficiency; carnitine deficiency; co-enzyme Q10 deficiency; Complex I deficiency; Complex II deficiency; Complex III deficiency; Complex IV deficiency; Complex V deficiency; cytochrome c oxidase (COX) deficiency, LHON—Leber Hereditary Optic Neuropathy; MM—Mitochondrial Myopathy; LIMM—Lethal Infantile Mitochondrial Myopathy; MMC—Maternal Myopathy and Cardiomyopathy; NARP—Neurogenic muscle weakness, Ataxia, and Retinitis Pigmentosa; Leigh Disease; FICP—Fatal Infantile Cardiomyopathy Plus, a MELAS-associated cardiomyopathy; MELAS—Mitochondrial Encephalomyopathy with Lactic Acidosis and Strokelike episodes; LDYT—Leber's hereditary optic neuropathy and Dystonia; MERRF—Myoclonic Epilepsy and Ragged Red Muscle Fibers; MHCM—Maternally inherited Hypertrophic CardioMyopathy; CPEO—Chronic Progressive External Ophthalmoplegia; KSS—Kearns Sayre Syndrome; DM—Diabetes Mellitus; DMDF Diabetes Mellitus+DeaFness; CIPO—Chronic Intestinal Pseudoobstruction with myopathy and Ophthalmoplegia; DEAF—Maternally inherited DEAFness or aminoglycoside-induced DEAFness; PEM—Progressive encephalopathy; SNHL—SensoriNeural Hearing Loss; Encephalomyopathy; Mitochondrial cytopathy; Dilated Cardiomyopathy; GER—Gastrointestinal Reflux; DEMCHO—Dementia and Chorea; AMDF—Ataxia, Myoclonus; Exercise Intolerance; ESOC Epilepsy, Strokes, Optic atrophy, & Cognitive decline; FBSN Familial Bilateral Striatal Necrosis; FSGS Focal Segmental Glomerulosclerosis; LIMM Lethal Infantile Mitochondrial Myopathy; MDM Myopathy and Diabetes Mellitus; MEPR Myoclonic Epilepsy and Psychomotor Regression; MERME MERRF/MELAS overlap disease; MHCM Maternally Inherited Hypertrophic CardioMyopathy; MICM Maternally Inherited Cardiomyopathy; MILS Maternally Inherited Leigh Syndrome; Mitochondrial Encephalocardiomyopathy; Multisystem Mitochondrial Disorder (myopathy, encephalopathy, blindness, hearing loss, peripheral neuropathy); NAION Nonarteritic Anterior Ischemic Optic Neuropathy; NIDDM Non-Insulin Dependent Diabetes Mellitus; PEM Progressive Encephalopathy; PME Progressive Myoclonus Epilepsy; RTT Rett Syndrome; SIDS Sudden Infant Death Syndrome; MIDD Maternally Inherited Diabetes and Deafness; and MODY Maturity-Onset Diabetes of the Young.

Nuclear Disease: Muscular Dystrophies, Ellis-van Creveld syndrome, Marfan syndrome, Myotonic dystrophy, Spinal muscular atrophy, Achondroplasia, Amyotrophic lateral sclerosis, Charcot-Marie-Tooth syndrome, Cockayne syndrome, Diastrophic dysplasia, Duchenne muscular dystrophy, Ellis-van Creveld syndrome, Fibrodysplasia ossificans progressive, Alzheimer disease, Angelman syndrome, Epilepsy, Essential tremor, Fragile X syndrome, Friedreich's ataxia, Huntington disease, Niemann-Pick disease, Parkinson disease, Prader-Willi syndrome, Rett syndrome, Spinocerebellar atrophy, Williams syndrome, Ataxia telangiectasia, Anemia, sickle cell, Burkitt lymphoma, Gaucher disease, Hemophilia, Leukemia, Paroxysmal nocturnal hemoglobinuria, *Porphyria*, Thalassemia, Crohn's disease, Alpha-1-antitrypsin deficiency, Cystic fibrosis, Deafness, Pendred syndrome, Glaucoma, Gyrate atrophy of the choroid and retina, Adrenal hyperplasia, Adrenoleukodystrophy, Cockayne syndrome, Long QT syndrome, Immunodeficiency with hyper-IgM, Alport syndrome, Ellis-van Creveld syndrome, Fibrodysplasia ossificans progressive, Waardenburg syndrome, Werner syndrome.

Infectious Disease: Viral—AIDS, AIDS Related Complex, Chickenpox (Varicella), Common cold, Cytomegalovirus Infection, Colorado tick fever, Dengue fever, Ebola haemorrhagic fever, Epidemic parotitis, Flu, Hand, foot and mouth disease, Hepatitis—Herpes simplex, Herpes zoster, HPV, Influenza, Lassa fever, Measles, Marburg haemorrhagic fever, Infectious mononucleosis, Mumps, Poliomyelitis, Progressive multifocal leukencephalopathy, Rabies, Rubella, SARS, Smallpox (Variola), Viral encephalitis, Viral gastroenteritis, Viral meningitis, Viral pneumonia, West Nile disease—Yellow fever; Bacterial—Anthrax, Bacterial Meningitis, Brucellosis, Bubonic plague, Campylobacteriosis, Cat Scratch Disease, Cholera, Diphtheria, Epidemic Typhus, Gonorrhea, Hansen's Disease, Legionellosis, Leprosy, Leptospirosis, Listeriosis, Lyme Disease, Melioidosis, MRSA infection, Nocardiosis, Pertussis, Pneumococcal pneumonia, Psittacosis, Q fever, Rocky Mountain Spotted Fever or RMSF, Salmonellosis, Scarlet Fever, Shigellosis, Syphilis, Tetanus, Trachoma, Tuberculosis, Tularemia, Typhoid Fever, Typhus, Whooping Cough; Parasitic—African trypanosomiasis, Amebiasis, Ascariasis, Babesiosis, Chagas Disease, Clonorchiasis, Cryptosporidiosis, Cysticercosis, Diphyllobothriasis, Dracunculiasis, Echinococcosis, Enterobiasis, Fascioliasis, Fasciolopsiasis, Filariasis, Free-living amebic infection, Giardiasis, Gnathostomiasis, Hymenolepiasis, Isosporiasis, Kala-azar, Leishmaniasis, Malaria, Metagonimiasis, Myiasis, Onchocerciasis, Pediculosis, Pinworm Infection, Scabies, Schistosomiasis, Taeniasis, Toxocariasis, Toxoplasmosis, Trichinellosis, Trichinosis, Trichuriasis, Trypanosomiasis.

Cancers: Breast and ovarian cancer, Burkitt lymphoma, Chronic myeloid leukemia, Colon cancer, Lung cancer, Malignant melanoma, Multiple endocrine neoplasia, Neurofibromatosis, p53 LieFrauMeni, Pancreatic cancer, Prostate cancer, retinoblastoma, von Hippel-Lindau syndrome, Polycystic kidney disease, Tuberous sclerosis.

Metabolic Disorders: Adrenoleukodystrophy, Atherosclerosis, Best disease, Gaucher disease, Glucose galactose malabsorption, Gyrate atrophy, Juvenile onset diabetes, Obesity, Paroxysmal nocturnal hemoglobinuria, Phenylketonuria, Refsum disease, Tangier disease, Tay-Sachs disease, Adrenoleukodystrophy, Type 2 Diabetes, Gaucher disease, Hereditary hemochromatosis, Lesch-Nyhan syndrome, Maple syrup urine disease, Menkes syndrome, Niemann-Pick disease, Pancreatic cancer, Prader-Willi syndrome, *Porphyria*, Refsum disease, Tangier disease, Wilson's disease, Zellweger syndrome, progerias, SCID.

Autoimmune Disorders: Autoimmune polyglandular syndrome, lupus, type I diabetes, scleroderma, multiple sclerosis, Crohn's disease, chronic active hepatitis, rheumatoid arthritis, Graves' disease, myasthenia gravis, myositis, antiphospholipid syndrome (APS), uveitis, polymyositis, Raynaud's phenomenon, and demyelinating neuropathies, and rare disorders such as polymyalgia rheumatica, temporal arteritis, Sjogren's syndrome, Bechet's disease, Churg-Strauss syndrome, and Takayasu's arteritis.

Inflammatory Disorders: Alopecia, Diastrophic dysplasia, Ellis-van Creveld syndrome, Asthma, Arthritis, including osteoarthritis, rheumatoid arthritis, and spondyloarthropathies.

Age-Related Disorders—Alzheimer Disease, Parkinson's Disease, Atherosclerosis, Age-Related Macular Degeneration, Age-related Osteoporosis.

The methods and compositions can also be used to treat, manage, or reduce symptoms associated with aging, in tissue regeneration/regenerative medicine, stem cell transplantation, inducing reversible genetic modifications, expressing inhibitory RNA, cognitive enhancement, performance enhancement, and cosmetic alterations to human or non-human animal.

D. Transgenic Non-Human Animals

The compositions and methods can also be used to generate transgenic non-human animals. In particular, zygote microinjection, nuclear transfer, blastomere electrofusion and blastocyst injection of embryonic stem (ES) cell cybrids have each provided feasible strategies for creating transgenic animals. In one embodiment an embryonic stem (ES) cell is transfected and injected into the blastocyst of a mammalian embryo as a means of generating chimeric mice. In another embodiment, embryonic stem (ES) cell are first prepared, followed by blastocyst injection into embryos. The use of cells carrying specific genes and modifications of interest allows the creation and study of the consequences of the transfected DNA. In theory, this technique offers the prospect of transferring any polynucleotide into a whole organism. For example, the methods and compositions could be used to create mice possessing the delivered polynucleotide in a specific cell type or cell state.

Single or multicellular non-human organisms, preferably non-human mammals, more preferably mice, can be transfected with the compositions by administering the compositions of the present disclosure to the non-human organism. In one embodiment, the polynucleotide remains episomal and does not stably integrate into the genome of the host organism. In another embodiment, the polynucleotide prevents the expression of a gene of interest. Thus, the expression of the polynucleotide in specific cells of the host can be controlled by the amount of polynucleotide administered to the host.

The transfected non-human organisms have several advantages over traditional transgenic organisms. For example, the transfected organism herein can be produced in less time that traditional transgenic organisms without sexual reproduction. Moreover, the expression of the polynucleotide of interest in the host can be directly regulated by the amount of polynucleotide of interest administered to the host. Dosage controlled expression of a polynucleotide of interest can be correlated to observed phenotypes and changes in the transfected animal. Additionally, inducible expression and/or replication control elements can be included in the polynucleotide of interest to provide inducible and dosage dependent expression and/or replication. Suitable inducible expression and/or replication control elements are known in the art. Furthermore, the effect of genes and gene modifications in specific cell types and states can be studied without affecting the entire cells of the animal.

X. Kits

Kits or packs that supply the elements necessary to conduct transfection of eukaryotic or prokaryotic organisms, in particular the transfection of specific cell types or cell states are also disclosed. In accordance with one embodiment a kit is provided comprising the polymers, and optionally a polyplex coating, for example a target specific coating. The polymer can be combined with a polynucleotide of the user's choosing to form a complex which can be used to transfect a host or a host cell. The polyplex can be further mixed with the coating to provide cell-type or cell-state specific tropism.

The individual components of the kits can be packaged in a variety of containers, e.g., vials, tubes, microtiter well plates, bottles, and the like. Other reagents can be included in separate containers and provided with the kit; e.g., positive control samples, negative control samples, buffers, cell culture media, etc. Preferably, the kits will also include instructions for use.

EXAMPLES

The present invention will be further understood by reference to the following non-limiting examples.

The problem to be solved: Protein therapeutics can be used as highly effective medical treatments for a wide array of diseases (Harris et al., *Pharmacol. Biochem. Behav.* 150e151 48e56 (2016), Jiang et al., *J. Control Release* 213 36e44 (2015), Natarajan et al., *Transl. Res.* 188 10e26 (2017), Efremenko et al., *J. Control Release* 247 175e181 (2017), Jiang et al., *Funct. Mater.* 28 (6) 1703982 (2018), Jiang et al., *J. Control Release* 231 38e49 (2016)). However, the clinical use of this therapeutic class has been limited by their cost and instability after systemic administration, revealing the need for new approaches to ensure sustained, efficient, and safe delivery (Carter, *Exp. Cell Res.* 317 (9) 1261e1269 (2011)). Gene therapies are attractive due to the promise of sustained protein secretion with low administration frequencies (Weissman, *Expert Rev. Vaccines* 14 (2) 265e281 (2015)).

While DNA-based therapies utilizing viruses offer the possibility of longterm protein expression, they also raise numerous safety concerns, especially regarding risks of insertional mutagenesis, induction of severe immune responses, and difficulty in controlling protein expression levels. In contrast to DNA, mRNA elicits the expression of an encoded protein without entering the nucleus, thus demonstrating higher efficiency at transfecting non-dividing cells while reducing the risk of insertional mutagenesis. mRNA therapy has an additional benefit that its dosing is scalable and the treatment is transiently linked to mRNA stability in the cytosol.

The solution to the problem: A "top-down" approach for synthesizing a library of polymeric materials is provided herein. Poly(amineco-ester) (PACE) have been used for gene delivery. PACE:pDNA polyplexes are among the most efficient and least toxic non-viral vectors (Zhou et al., *Nat. Mater.* 11 (1) 82e90 (2012)). PACE polymers were designed to possess several key features: (1) biodegradability, provided by the ester linkage in the main chain of the polymer; (2) low cationic charge density that allows for electrostatic complexation with nucleic acids while avoiding toxicity associated with highly cationic polymers; and (3) hydrophobicity provided by the lactone groups that stabilizes polyplex. The tolerance of the lipase chemistry provides a high chemical versatility, allowing for the modulation of the polymer structure via monomer selection, to readily yield a family of different materials. Such versatility is promising to translate the PACE technology for mRNA delivery.

Example 1: PACE Polymer can Deliver mRNA

Materials and Methods
 Materials
 u-pentadecalactone (PDL), diethyl sebacate (DES), sebacic acid, N-methyldiethanolamine (MDEA), chloroform, dichloromethane, hexane, chloroform-d, chromium (III) acetylacetonate, ethylene diamine, ethanol amine, glycine, and 1,10-carbonyldiimidazole (CDI) were purchased from Sigma Aldrich (Saint Louis, MO) and were used as received. 2[(2-Aminoethyl)(methyl)amino]ethanol (AEMAE) was purchased from ChemBridge Corporation (San Diego, CA) Immobilized *Candida antarctica* lipase B (CALB) supported on acrylic resin (Novozym 435) was also obtained from Sigma Aldrich and was dried at 50° C. under 2.0 mmHg for 20 h prior to use. TransIT-mRNA transfection kit was purchased from Mirus Bio LLC (Madison, WI). Modified Fluc mRNA encoding for luciferase and murine EPO mRNA encoding for erythropoietin (EPO) were purchased from TriLink Biotechnologies (San Diego, CA). HEK293 cells, Daoy cells, and SH-SY5Y cells were purchased from ATCC (Manassas, VA).
 Polymer Synthesis
 PACE synthesis was performed as previously described (Zhou et al., *Nat. Mater.* 11 (1) 82-90 (2012)), including several modifications to produce polymers with different structures. Briefly, (1) to obtain either classic or acidic PACE, diethyl sebacate or sebacic acid were used for the polymerization; (2) to vary the hydrophobicity of classic PACE, different percentages of PDL (10% or 20%) were added to the reactants, and (3) to vary the molecular weight (MW) of classic PACE containing 10% PDL, the second stage reaction time was varied between 8 and 72 h, in order to obtain polymers with MW ranging from 2 kDa to 20 kDa.

Results

PACE is a family of terpolymers formed through enzymatic copolymerization of diesters/diacids with amino-substituted diols and lactones. PACE can efficiently deliver pDNA (Zhou et al., *Nat. Mater.* 11 (1) 82e90 (2012)), microRNA (Adams et al., *Cancer Res.* 76 (4) 927e939 (2016)), and siRNA (Cui et al., *Nat. Commun.* 8 (1) 191 (2017)). However, given the structural differences between mRNA and these other nucleic acids (Kauffman et al., *Nano Lett.* 15 (11) 7300e7306 (2015)), modification of existing PACE structures, and/or development of new PACE variants were considered as a means of improving delivery. The high tolerance of the lipase catalyst offers a versatility of structures, especially in terms of hydrophobicity and MWs. Starting from one of the most efficient PACE compositions for delivery and transfection of DNA (classic PACE), different polymers with varied MWs and lactone contents in order to specifically improve mRNA delivery and transfection.

orders of magnitude ($1.1 \times 10^5$ RLU/mg and $4.4 \times 10^7$ RLU/mg, respectively) were observed. However, this trend appears to plateau at 5 kDa since the level of transfection dramatically decreased using PACE MW of 2 kDa, comparable to the level obtained with free mRNA. Previous studies have reported that the strength and the stability of electrostatic complexation between polycations and polyanions increase exponentially with the length of the polycation (Akinc et al., *Bioconj. Chem.* 14 (5) 979e988 (2003), Tsuchida & Osada, *Makromol. Chem.* 175 (2) 593e601 (1974), Choosakoonkriang et al., *J. Pharmaceut. Sci.* 92 (8) 1710e1722 (2003), Schaffer et al., *Biotechnol. Bioeng.* 67 (5) 598e606 (2000)).

These results show that very short polymers (2 kDa) are inefficient for transfection, likely due to poor complexation of the mRNA. On the other hand, above the 2 kDa threshold, shorter polymers (5 kDa) are more efficient at delivering mRNA than higher MW polymers (10 kDa or 20 kDa), likely due to the inefficient release of mRNA from highMW PACE polyplexes inside the cells. High MW PACE chains contain a large number of positive charges and hydrophobic

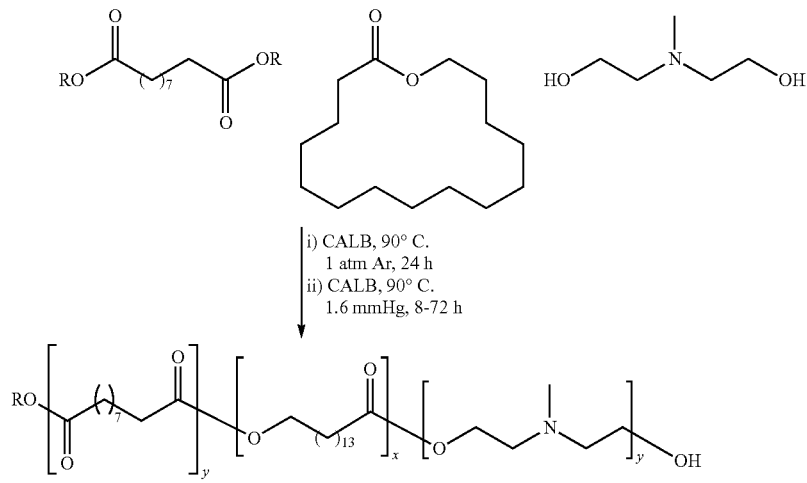

PACE synthesis was modified to vary different parameters in the final polymer. Diethyl sebacate (R=CH2CH3), or sebacic acid (R=H) were used to make classic (ester/OH) ended or acidic (COOH/OH) ended PACE, respectively. With classic PACE, the duration of the second step of the synthesis was varied from 8 to 72 h to vary the MW. The PDL content (10% or 20%) was varied to modify the polymer hydrophobicity.

Gel Permeation Chromatography (GPC) was used to determine polymer MW. All the PACE polymers were able to complex mRNA, and formed nanosized polyplexes with neutral or negative surface charges.

When evaluated using the RiboGreen assay, all the polymers were able to encapsulate mRNA with efficiencies ranging from 55 to 76%. The ability of the different PACE polymers to transfect luciferase (LUC) expressing mRNA in HEK-293 cells was used to screen in vitro transfection performance. None of these PACE polymers, representing different structural modifications, provided transfection levels comparable to the commercial agent TransIT, which was used as a positive control (FIG. 1A-1C). However, a clear trend in transfection levels with the MW of the polymers was observed (FIG. 1A). As polymer MW decreased from 20 kDa to 5 kDa, an increase in transfection efficiency of 2 domains, which lead to thermodynamically stable binding with mRNA and prevent its release from the polyplexes. The results indicate that efficient mRNA delivery comes from a fine balance of the MW of the polymer: polymer chain length needs to be long enough to ensure complexation of the mRNA and stabilization of the polyplex, but short enough for mRNA release inside the cells. On the other hand, increasing the PDL content from 10% to 20% of a 10 kDa PACE polymer did not significantly affect transfection efficiency (FIG. 1B), which is contrary to what has been observed with pDNA, and confirming that the polymer structure benefits from modulation for each genetic material.

This shows that polymers having a molecular weight between greater than 2 kDa and less than 10 kDa, more preferably in the range of 3 kDa to 8 kDa, most preferably 5 kDa, would be most effective.

Example 2: PACE Transfection Efficiency is Highly Dependent on its End Group Composition Materials and Methods Modification of Polymer End Groups To prepare PACE with different end groups, the parent polymer was synthesized with sebacic acid instead of diethyl sebacate, which yields PACE with a mixture of hydroxyl and carboxyl end groups. Both of the end groups were then activated with CDI at a molar ratio of 1:40 by stirring in dry dichloromethane overnight at room temperature. The mixture was washed three times with deionized water, followed by evaporation of DCM under vacuum to obtain the reactant, PACE-CDI (see scheme below).

PACE-CDI was reacted with amine-containing molecules to yield PACE with new end groups. Specifically, glycine and AEMAE was used to generate PACE-COOH and PACE-MAE, respectively. For conjugation, 5 mM glycine or AEMAE was reacted with 0.5 mM of PACE-CDI in DMSO for 40 h at room temperature under constant stirring. After reaction, the mixture was washed with 10-fold volume of deionized water, extracted with DCM, followed by evaporation of DCM under vacuum to obtain PACE-COOH and PACE-MAE. When this protocol was adopted to synthesize 10 kDa acidic PACE, the 5 kDa PACE-CDI and ethylenediamine were added at an exact molar ratio of 2:1.

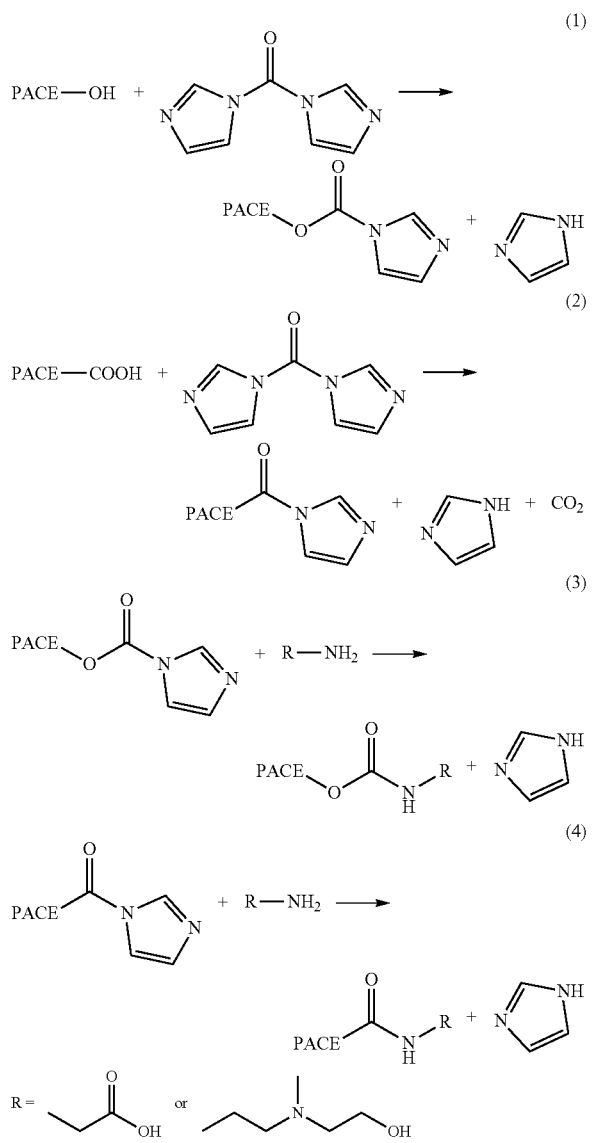

As illustrated above, to obtain PACE with —COOH or -MAE end groups, acidic PACE by CDI activation (1, 2), followed by nucleophilic substitution with an amine-containing molecule (3,4; R=glycine, or AEMAE).

Polymer Characterization 1H and 13C NMR spectrawere recorded on a Bruker AVANCE 500 spectrometer. For inverse gated 13C NMR, samples were prepared at 50 mg/mL of polymer in chloroform-d, and chromium (III) acetylacetonate (Cr (acac)3) was added at a concentration of 5 mg/mL as a relaxation agent. The signal was recorded using a T1 relaxation time of 10 s. The molecular weights (MW) of polymers were measured by gel permeation chromatography (GPC) using a Waters HPLC system equipped with a microSTYRAGEL column (mixed bed; pore sizes 100 Å—$10^6$ Å). Chloroform containing 0.2 wt % triethylamine was used as the eluent at a flow rate of 1 mL/min. Sample concentrations of 2 mg/mL and injection volumes of 100 μL were used. Polymer MW was determined based on a conventional calibration curve generated by narrow polydispersity polystyrene standards from Sigma Aldrich (Saint Louis, MO). Empower II GPC software was used to run the GPC instrument and to perform MW calculations.

Polyplex Preparation and Characterization

Unless specified, polymer:mRNA polyplexes were prepared at a 100:1 polymer:mRNAweight ratio in 25 mM sodium acetate buffer (pH 5.8). For in vitro experiments, a solution at 10 μg mRNA/mL was prepared: 1 μL of polymer solution (100 mg/mL in DMSO) was first diluted in 50 μL sodium acetate buffer. After brief vortexing, the polymer solution was mixed with 1 μg mRNA diluted in 50 mL sodium acetate buffer, and vortexed again. The polymer:mRNA mixture was incubated at room temperature for 10 min before use. For in vivo experiments, a solution at 100 μg mRNA/mL in sodium acetate buffer was prepared by the same method.

The hydrodynamic diameter of the polyplexes was measured by Dynamic Light Scattering (DLS) using a Malvern Nano-ZS (Malvern Instruments, UK), after dilution of polyplexes in DI water at a concentration of 2 μg/mL of mRNA. To measure zeta potential, the same solution was loaded into a disposable capillary cell and analyzed on a Malvern Nano-ZS.

Encapsulation efficiency (EE) of mRNA in the polyplexes was measured using the Quant-IT RiboGreen RNA kit (Invitrogen, #R11491) according to manufacturer instructions. As the RiboGreen assay measures the amount of free mRNA in solution, this amount was subtracted to the initial amount added to form the polyplexes, to obtain the amount of mRNA complexed within the polyplexes.

Cell Culture

HEK293 cells and SH-SY5Y cells were cultured in 4.5 g/L glucose DMEM media (Gibco #11965) supplemented with 10% FBS and 1% pen/strep at 37° C. and 5% $CO_2$. Daoy cells were cultured in 2 mM L-glutamine, 1 mM sodium pyruvate, and 1500 mg/L sodium bicarbonate EMEM media (ATCC #30-2003) supplemented with 10% FBS and 1% pen/strep at 37° C. and 5% $CO_2$.

In Vitro Transfection

For in vitro transfection of Fluc mRNA, cells were seeded in 24-well plates at a density of 75,000 cells/well in 500 μL of media and incubated over-night to ensure adherence. Media was replaced by 400 μL of transfection media (culture media containing 10% FBS, but without pen/strep), and 100 μL of polyplexes (1 μg of mRNA total) was added to each well. For free mRNA control, 1 μg of mRNA was diluted in 100 μL of acetate buffer and added to the wells. The commercial mRNA transfection kit TransIT was used as a control. Briefly, 1 μg of mRNA was mixed with 0.7 μL of Boost reagent and 1.1 μL of TransIT reagent in 100 μL of OPTIMEM media (Gibco #11058021). 24 h after transfection, luciferase expression was measured. Cells were washed and lysed using 200 μL of 1× lysis buffer (Promega, #E397A) and one freeze-thaw cycle at −80° C. 20 μL of the lysate was then mixed with 100 μL of luciferase reporter reagent (Promega, #E1483), and luminescence was read on a Glomax luminometer (Promega). Lysate protein content was measured using a Pierce BCA protein assay kit (ThermoFisher, #23225). All experiments were run three independent trials in duplicate.

Results

Figure 2:
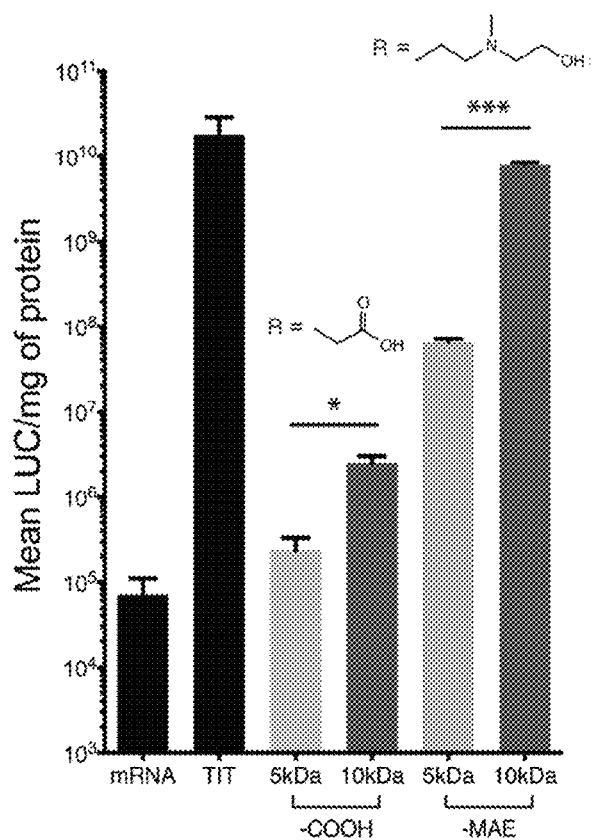
FIG. 2 is a bar graph showing transfection efficiency of PACE-COOH and PACE-MAE with MW of either 5 kDa or 10 kDa, synthesized by methods illustrated in Example 2. Statistical significance was determined by Student's t-test (indicated as follows: *, $P<0.05$; ***, $P<0.001$).

FIG. 2 is a bar graph showing transfection efficiency of PACE-COOH and PACE-MAE with MW of either 5 kDa or 10 kDa, synthesized by methods illustrated in Example 2. Statistical significance was determined by Student's t-test (indicated as follows: *, $P<0.05$; ***, $P<0.001$).

PACE synthesized by terpolymerization of diethyl sebacate, PDL, and MDEA, contains a mixture of methyl (from diethyl sebacate) and hydroxyl (from MDEA) end groups. When the monomer diethyl sebacate was replaced by sebacic acid for PACE synthesis to form acidic PACE, its mRNA transfection efficiency doubled (FIG. 2). Different end groups on the same polymer can dramatically affect transfection efficiency of pDNA (Sunshine et al., *Biomacromolecules* 12 (10) 3592e3600 (2011), Sunshine et al., *Mol. Pharm.* 9 (11) 3375e3383 (2012)). Experiments were designed to determine if end group compositions can also affect mRNA transfection, and more particularly if modified end groups on PACE could improve mRNA delivery.

Acidic PACE, which contains a mixture of carboxyl and hydroxyl end groups with a molecular weight around 5 kDa, was used as the starting material. Both of these two end groups can be activated by 1,10-Carbonyldiimidazole (CDI), which was further substituted by amine-containing molecules including glycine or AEMAE, to form a carboxyl (eCOOH) end group (PACE-COOH) or a (methylamino) ethanol (-MAE) end group (PACE-MAE), respectively.

PACE with —COOH or -MAE end groups, acidic PACE was obtained by CDI activation, followed by nucleophilic substitution with an amine-containing molecule (3,4; R=glycine, or AEMAE).

These two monomers were chosen to mimic the naturally occurring mix of end groups found in acidic PACE, in order to identify the end group with higher transfection efficiency. The reaction mechanism ensured more than 90% conversion rates for both end groups, as confirmed by NMR spectroscopy.

Figure 3A:
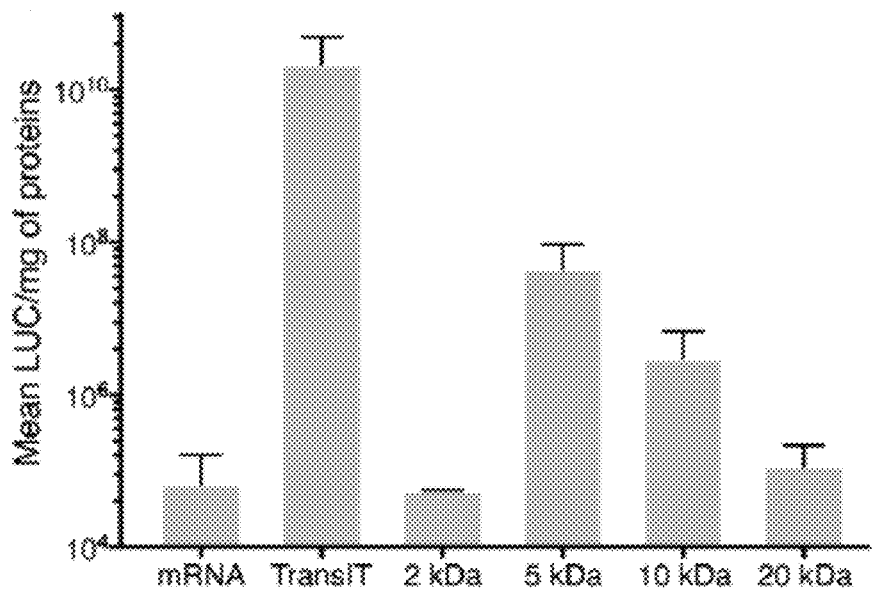
FIG. 3A is a bar graph showing the effect (Mean LUC/mg proteins) of MW using classic PACE with 10% PDL content, molecular weights 2 kDa, 5 kDa, 10 kDa, and 20 kDa.
Figure 3B:
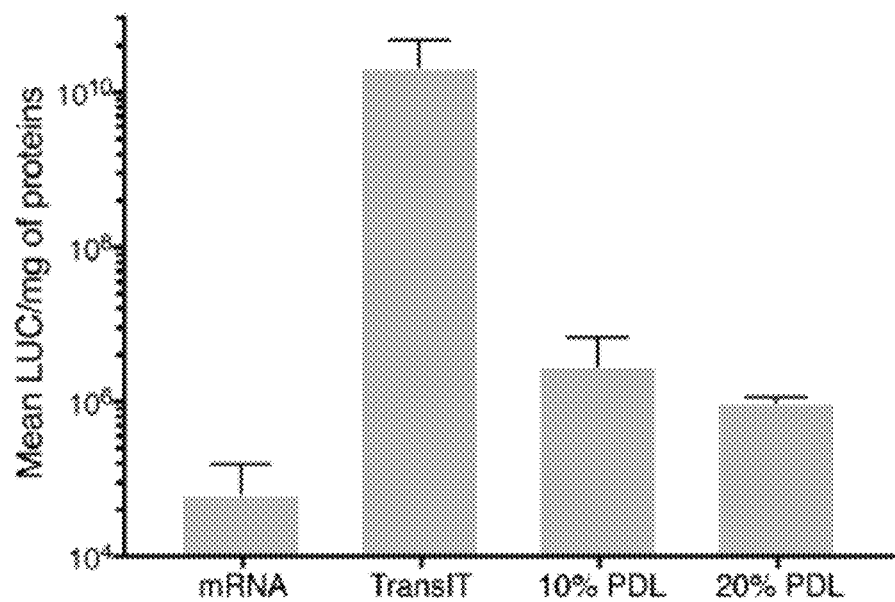
FIG. 3B is a bar graph showing the effect (Mean LUC/mg proteins) of PDL content using a 10 kDa classic PACE polymer.
Figure 3C:
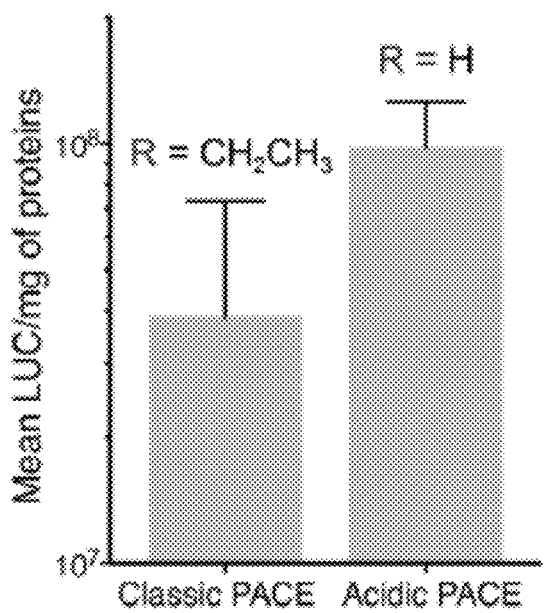
FIG. 3C is a bar graph showing the transfection efficiency (Mean LUC/mg proteins) of acidic PACE and Classic PACE with MW of 5 kDa at 10% PDL content. Results are presented as mean±SD of three independent experiments run in duplicate.

Next, the abilities of these polymers to transfect mRNA in vitro were evaluated. FIG. 3A is a bar graph showing the effect (Mean LUC/mg proteins) of MW using classic PACE with 10% PDL content, molecular weights 2 kDa, 5 kDa, 10 kDa, and 20 kDa. FIG. 3B is a bar graph showing the effect (Mean LUC/mg proteins) of PDL content using 10 or 20% PDL of a 10 kDa classic PACE polymer. FIG. 3C is a bar graph showing the transfection efficiency (Mean LUC/mg proteins) of acidic PACE and Classic PACE with MW of 5 kDa at 10% PDL content. Results are presented as mean±SD of three independent experiments run in duplicate.

Significant differences in transfection efficiency were observed between PACE with different end groups, as the 5 kDa PACE-MAE polymer demonstrated two orders of magnitude higher transfection efficiency than PACE-COOH of the same MW (FIG. 3C). This effect can be explained by the difference in EE of these two polymers, as PACE-MAE encapsulated 98% of total mRNA, PACE-COOH were only able to encapsulate 18%. Although acidic PACE at molecular weights higher than 5 kDa were not directly synthesized due to technical challenges (difficulty in removing the water byproduct as the polymer chain grows longer), 10 kDa acidic PACE can be obtained by CDI activation of the 5 kDa polymers followed by crosslinking two polymer chains with an ethylene diamine molecule. Remarkably, when 10 kDa acidic PACE was modified with either carboxyl or hydroxyl end groups, its transfection efficiency was significantly improved compared with its 5 kDa counterparts (FIG. 3A), meaning that for PACE-COOH and PACE-MAE polymers, transfection efficiency increases when the MW increases. This behavior is dramatically different from classic PACE whose transfection efficiency decreases as MW increases, further demonstrating the importance of end groups in transfection efficiency. Although the EE of PACE-COOH increased from 18% to 45% when its MW increased from 5 kDa to 10 kDa, the EE of PACE-MAE actually did not change much (98% at 5 kDa vs. 95% at 10 kDa), indicating that an increase in EE is not the only explanation for the transfection efficiency improvement.

Considering the complicated biological steps involved in intracellular mRNA delivery, these data show that the contribution of PACE end groups and MW are more than additive. While the nature of PACE end groups appears to contribute to its capability of complexation with mRNA, the MW also plays a role in complexation, and can be involved in down-stream biological steps, such as endosomal escape and/or mRNA release in the cytosol.

Example 3: "Top-Down" Actuation of PACE for mRNA Delivery Actuated PACE Polymers Materials and Methods Actuation of Polymers Polymers (20-30 mg) with different starting MWs were spread evenly on the inner surface of glass vials, forming thin films to ensure efficient air penetration. The vials were then incubated at a controlled temperature (typically 37° C.) with exposure to flowing wet air for different lengths of time.

In Vitro Toxicity

To evaluate the cytotoxicity of PACE polymers and TransIT, HEK293 cells were seeded in 96-well plates at a density of 10,000 cells/well in 100 μL of media and incubated overnight to ensure adherence. The polymer:mRNA polyplexes or TransIT/mRNA complexes were formed using the same w:w ratios as for transfection experiments, and diluted in transfection media at different concentrations. 100 μL of polyplexes containing media were added to the wells to achieve final concentrations of mRNA ranging from 0.01 to 20 μg/mL. After 24 h of incubation, cell viability was measured using a MTT assay. All experiments were run three independent trials in duplicate.

Lyophilization of the Polyplexes

PACE:mRNA polyplexes were prepared using sodium acetate buffer, and trehalose solutions at different concentrations (30 mg/mL or 60 mg/mL in 25 mM sodium acetate buffer, pH=5.8) were added to the polyplex suspension at a 1:1 volume ratio to obtain final trehalose concentrations of 0, 15 or 30 mg/mL. The mixtures were then snap frozen in liquid nitrogen and lyophilized for 2 days. At the end of the lyophilization, the polyplexes were resuspended in sodium acetate buffer and transfection efficiency was evaluated in HEK293 cells. The transfection and characterization of the gene expression were performed using the methods described above.

Results

After an initial screening with the "bottom-up" synthesis of a library of PACE, polymer MW and end group composition were identified as two important parameters that determine the transfection efficiency of this material for mRNA. In particular, the effect of MW appeared to significantly affect the transfection efficiency within a narrow range between 5 kDa and 10 kDa. A "top-down" approach was adapted to simultaneously vary PACE MW and end groups through controlled hydrolysis of high MW polymers. By doing this, PACE end groups with higher transfection efficiency, and MW were modulated and identified.

This method produced a new family of materials called actuated PACE (aPACE). These biodegradable aPACE polymers yielded high transfection levels both in vitro and in vivo with negligible toxicity.

(aPACE) were produced by controlled hydrolysis of the ester backbone. Exposure to air under moderate temperature provides mild conditions for hydrolysis of PACE, thus decreasing its MW and exposing hydroxyl and carboxyl end groups.

Figure 4:
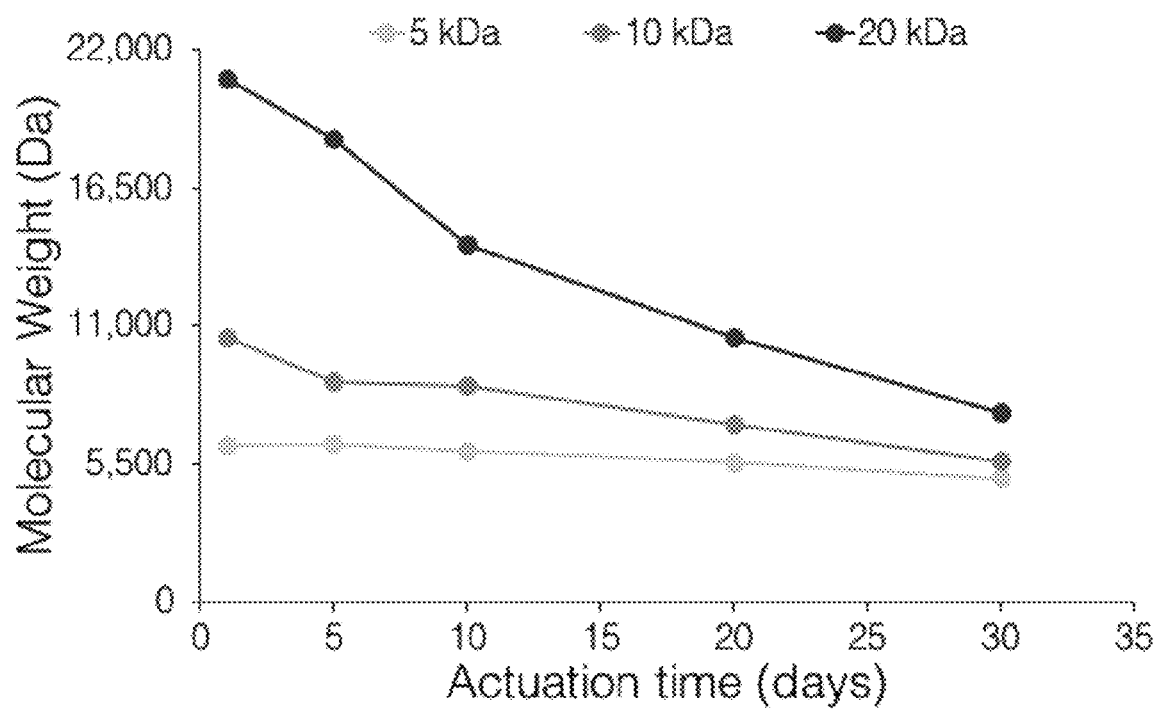
FIG. 4 is a line graph showing evolution of weight-average MW (Da) of aPACE polymers (5 kDa—bottom line; 10 kDa—middle line; 20 kDa—top line) during the actuation process (Actuation time in days).

To confirm this, aPACE was characterized by NMR spectroscopy and GPC. NMR analysis of aPACE demonstrated that the actuation process resulted in the exposure of hydroxyl and carboxyl end groups, as an increase in the area under the hydroxyl group peak (58.2 and 58.9 for aPACE and classic PACE, respectively) and the appearance of a clear carboxyl peak at 178 ppm in aPACE compared to classic non-actuated PACE were observed. GPC showed that the actuation process decreased the MW of all PACE polymers (FIG. 4).

Hydrolysis of polyesters are well known. These reactions can usually proceed at high temperatures, high pressures, and/or in the presence of a catalyst. It was observed that the actuation could be accelerated when performed at 100° C. compared to 37° C. However, using milder temperatures provided for a more reproducible process, that resulted in the desired molecular weights of the aPACE.

Figure 5B:
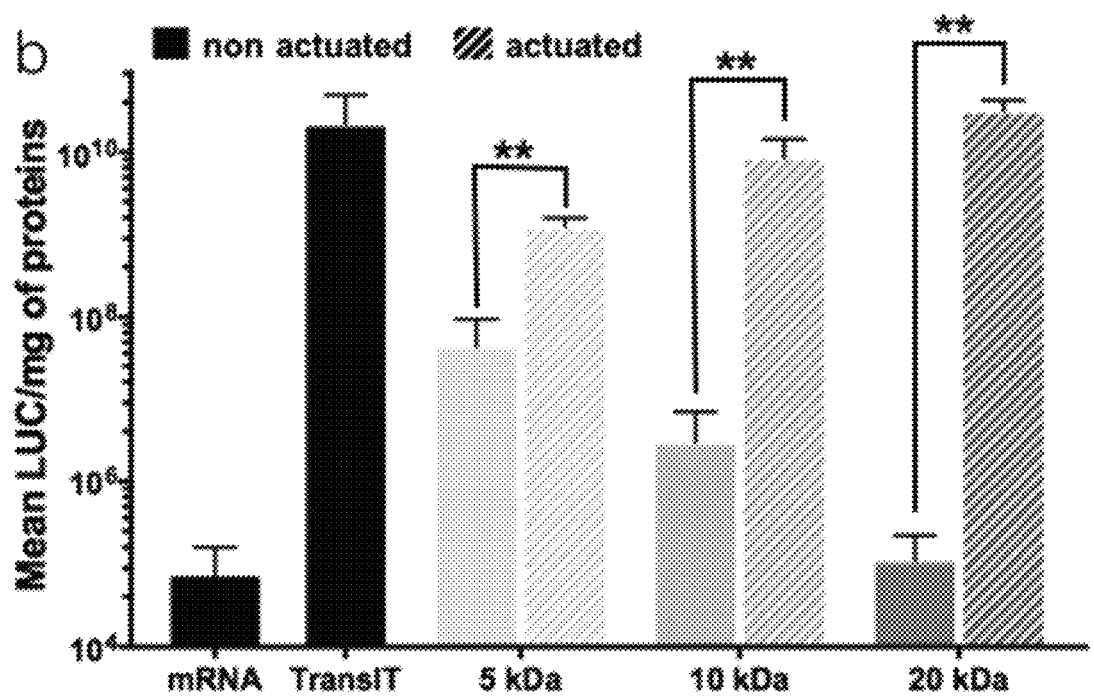
FIG. 5B is a bar graph showing transfection efficiency (Mean LUC/mg proteins) using non-actuated PACE and actuated PACE of different initial MW at their preferred actuation time (5 days for the 5 kDa polymer, 10 days for the 10 kDa polymer, and 30 days for the 20 kDa polymer, $p<0.005$).

To explore the effect of the actuation protocol on PACE transfection efficiency for mRNA, aPACE produced from different starting MW with different periods of actuation were tested. Self-assembled polyplexes produced from aPACE and mRNA were highly effective at transfecting HEK293 cells, leading to levels of luciferase expression comparable to the positive control, TransIT (FIGS. 5A-5B). Transfection efficiency appeared to be dependent on the actuation time, and the initial MW of the actuated polymer, with an optimal actuation time for each initial MW (FIG. 5A: 5 days for the 5 kDa polymer, 10 days for the 10 kDa polymer, and 30 days for the 20 kDa polymer). For these improved actuation times, all aPACE polymers provided comparable levels of transfection to TransIT, and significantly higher transfection levels compared to their non-actuated counterparts (FIG. 2, p<0.005).

Figure 5C:
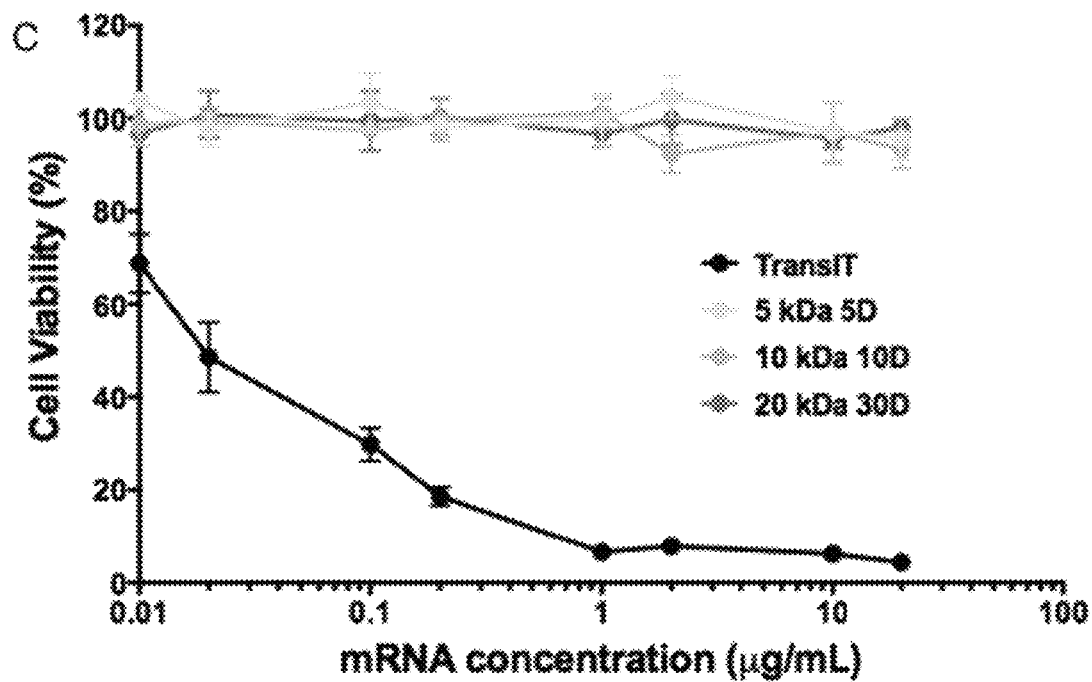
FIG. 5C is a line graph showing cytotoxicity profiles (Cell Viability (%)) of mRNA:aPACE polyplexes (5 kDa 5 D, 10 kDa 10 D, 20 kDa 30 D (cluster of top lines)) compared to the mRNA:TransIT complexes (bottom line).

When tested for cytotoxicity at different concentrations, TransIT induced considerable cell death, while for similar amounts of mRNA delivered, all aPACE formulations were non-cytotoxic (FIG. 5C).

Figure 5D:
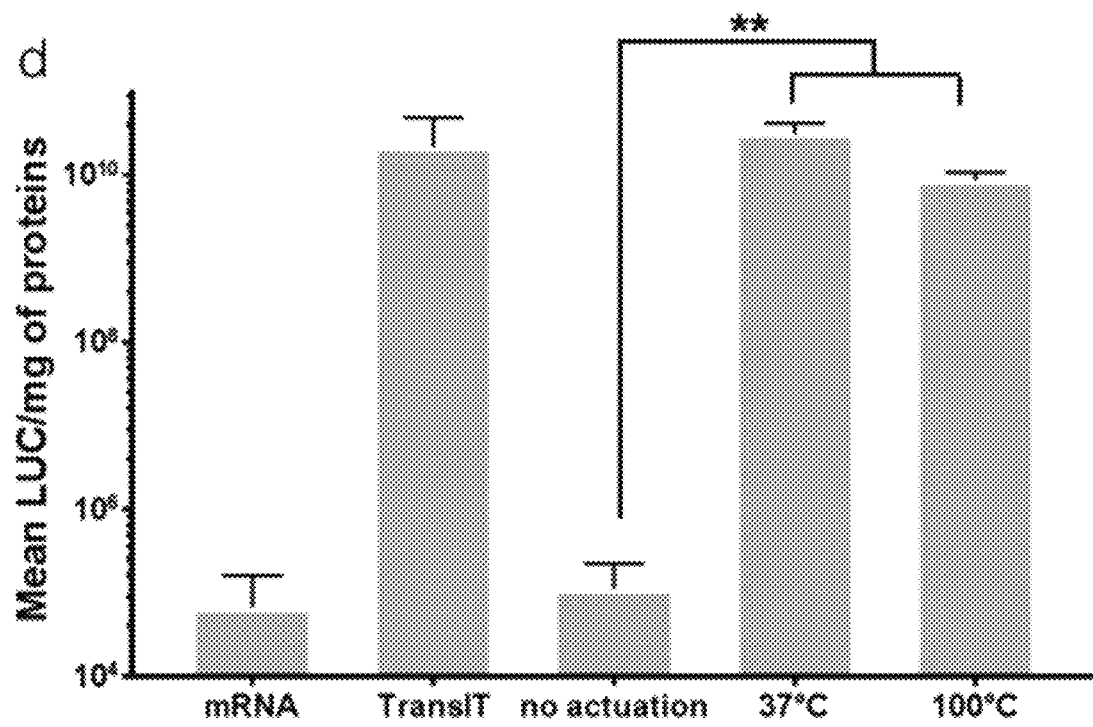
FIG. 5D is a bar graph of transfection efficiency (Mean LUC/mg proteins) of aPACE using different temperature of actuation ($p<0.005$). All results are presented as mean±SD of three independent experiments run in duplicate.

The accelerated actuation process where 20 kDa polymer was actuated for 6 h at 100° C. resulted in similar transfection levels as the 20 kDa polymer actuated for 30 days at 37° C. (FIG. 5D). Despite an accelerated actuation process, a similar kinetic profile was observed when performing the actuation at 100° C. compared to 37° C. Both processes exhibited an increase in transfection efficiency up to an optimum, followed by a drop of activity. This observation indicates that a similar time-dependent process is occurring at both temperatures.

The MW of these aPACEs were close to each other, ranging from 6 kDa to 8 kDa. Considering the differences in their transfection efficiency, the data indicates rapid changes in transfection efficiency within a narrow range of aPACE MW, highlighting the value of using a "top-down" actuation approach for screening. Since delivery vehicles should be modulated for carriage of different genetic materials, a controlled "top-down" actuation process constitutes a straightforward and powerful way to optimize the combination of MW and end-group for each genetic material. The advantage of this process involves the accuracy in fine-tuning key factors like MW, as well as the simplicity of synthesizing a discrete library of polymers at actuation stages from the same starting material. Overall, the results confirmed that the approach provided an optimal combination of MW and end-group tailored for mRNA delivery and transfection.

To ensure broad efficacy of aPACE, these polymers were also tested for transfection in Daoy cells, a human medulloblastoma cell line, and in SH-SY5Y cells, a human neuroblastoma cell line. As observed in the HEK293 cells, the actuation process significantly increased PACE transfection efficiency in both cell lines.

The effect of lyophilization on aPACE:mRNA polyplexes was also tested. Trehalose was used as a cryoprotectant, and transfection efficiency was assessed in HEK293 cells after reconstitution of the polyplexes. Lyophilized polyplexes prepared with aPACE were as efficient as fresh polyplexes, even in the absence of cryoprotectant, while the addition of high concentration of trehalose (6%) slightly increased the transfection efficiency.

Example 4: aPACE is Effective for mRNA Delivery In Vivo

Materials and Methods

In Vivo Studies

All animal work was completed at Yale University in accordance with Yale Animal Resource Center (YARC) and the Institutional Animal Care and Use Committee (IACUC) guidelines. Female BALB/c mice (20 g, Charles River, Willimantic, CT, USA) were used for the experiments.

PACE:mRNA polyplexes (0.1 mg/mL in mRNA, N=3), aPACE:mRNA polyplexes (0.1 mg/mL in mRNA, N=3), TransIT: mRNA complexes (0.1 mg/mL in mRNA, N=3), free mRNA diluted in sodium acetate buffer (0.1 mg/mL in mRNA, N=3) or sodium acetate buffer (25 mM, pH 5.8, N=3) were administered intravenously through the tail vein in a volume of 200 µL.

Retroorbital blood collections (50 µL) were performed before particle administration, and 6 h, 24 h, 48 h, 72 h and 7 days after injection. Immediately after blood collection, plasma was separated by centrifugation (3000 g, 10 min) and frozen at −80° C. until further analysis. EPO concentration in plasma was measured using an ELISA kit (R&D Systems). 24 h and 7 days after injection, liver, kidney and spleen were collected, processed for H&E staining and scored by an external pathologist for any abnormal cellular morphology. GraphPad Software, La Jolla California USA, www.graphpad.com/) was used for graphing and statistical analysis. Statistical significance was tested using a two-tailed unpaired student's t-test with a level of confidence of 95%.

Results

To evaluate aPACE polymers for delivery of therapeutically relevant mRNA, their ability to deliver EPO-expressing mRNA was evaluated in mice. Two aPACE polymers (PACE 5 kDa actuated for 5 days and PACE 10 kDa actuated for 10 days) were tested and compared to the positive control TransIT, which was selected because of its proven effectiveness for mRNA delivery in vivo (Kariko et al., Mol. Ther. 20 (5) 948e953 (2012)). PACE 20 kDa actuated for 30 days was not tested, as the formed polyplexes were not stable enough in terms of size at high concentrations required for in vivo administration.

EPO mRNA:aPACE polyplexes were intravenously administered to wild-type mice to deliver a total dose of 20 mg of mRNA, and blood was collected at different timepoints after injection to measure EPO levels by ELISA. mRNA polyplexes using optimized aPACE polymers demonstrated high efficacy in the delivery of EPO mRNA, as reflected in subsequent EPO production.

Six hours after injection, the non-actuated PACE 5 kDa, which was the best of non-actuated polymers, produced a high level of EPO (530 ng/mL), higher than the positive control TransIT (170 ng/mL). 10 kDa non-actuated PACE produced a lower EPO level (14 ng/mL) at 6 h, confirming the trend observed in vitro: for the non-actuated polymers, that polyplexes formed from polymers with MW higher than 5 kDa provide lower transfection efficiency. In vivo EPO production is used to evaluate the potency of mRNA delivery systems. The commercial transfection agent, TransIT, has been used to deliver mRNA with modified structures (Kariko et al., Mol. Ther. 20 (5) 948e953 (2012)). Administering a total dose of 0.1 mg mRNA per animal intraperitoneally increased EPO levels up to around 10 ng/mL, when measured 6 h after administration.

FIG. 5A is a line graph showing Luciferase mRNA transfection efficiency (Mean LUC/mg proteins) depending on the actuation time (days) demonstrating a preferred actuation time for each MW (lines identified as 20 kDa—bottom data point at 0 days; 10 kDa middle data point at 0 days; 5 kDa—top data point at 0 days). The actuated 5 kDa PACE did not significantly increase the EPO production compared to its non-actuated form, but the actuation of the 10 kDa for 10 days at 37° C., increased the EPO level significantly, to 1100 ng/mL (FIG. 5A, p<0.0001).

FIG. 5B is a bar graph showing transfection efficiency (Mean LUC/mg proteins) using non-actuated PACE and actuated PACE of different initial MW at their preferred actuation time (5 days for the 5 kDa polymer, 10 days for the 10 kDa polymer, and 30 days for the 20 kDa polymer, p<0.005). FIG. 5D is a bar graph of transfection efficiency (Mean LUC/mg proteins) of aPACE using different temperature of actuation (p<0.005).

Figure 6A:
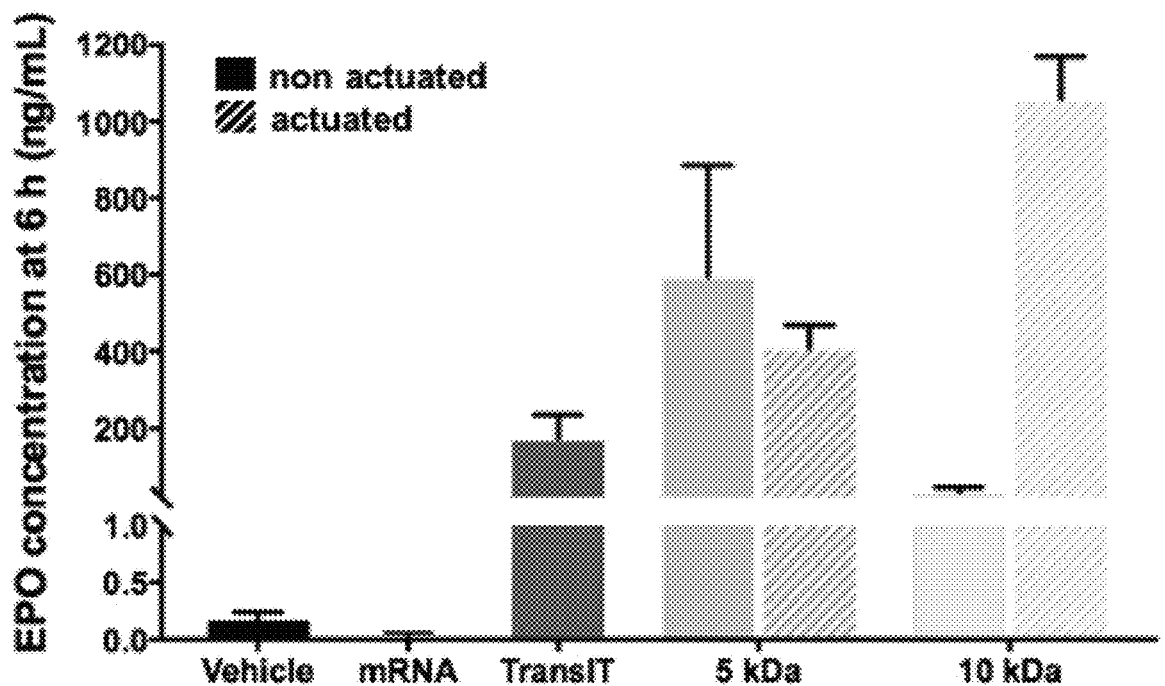
FIG. 6A is a bar graph showing the EPO blood concentration 6 h after IV administration of mRNA (20 mg total) using TransIT, 5 kDa non-actuated PACE, 5 kDa aPACE actuated for 5 days, 10 kDa non-actuated PACE, or 10 kDa aPACE actuated for 10 days. Results are presented as mean±SD of N=3 animals (**$p<0.0001$).
Figure 6B:
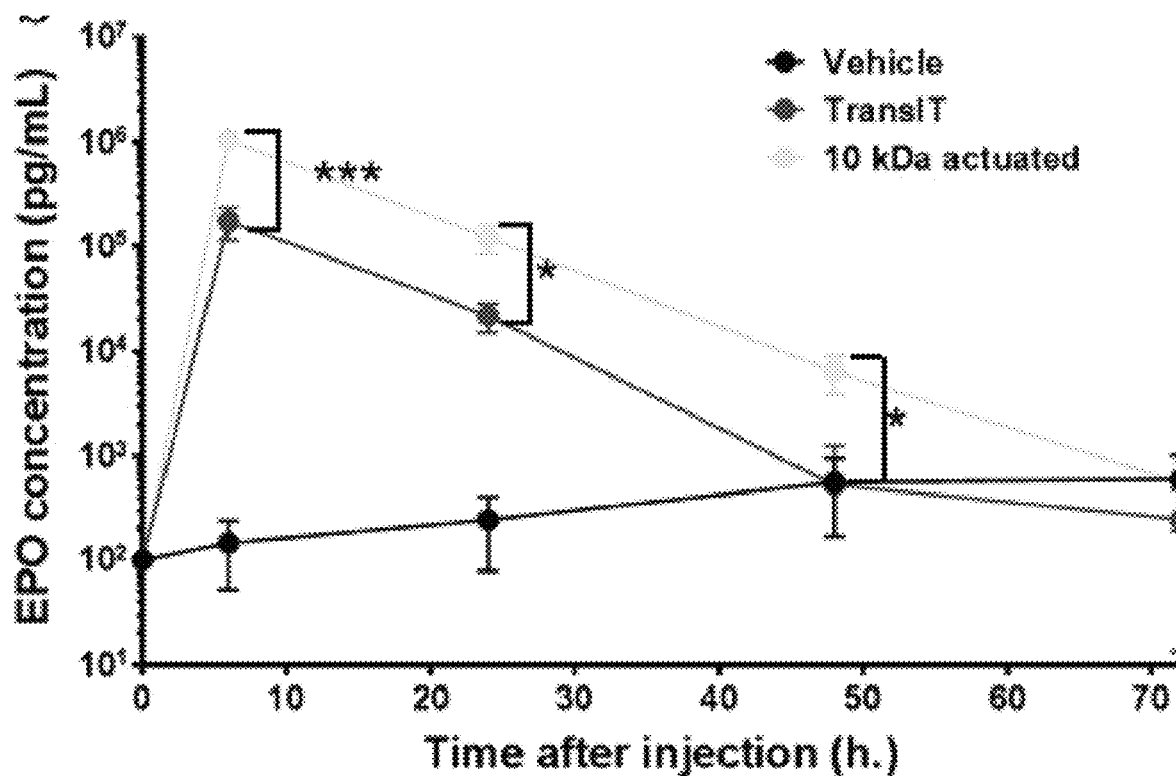
FIG. 6B is a line graph showing a time course of EPO production following IV administration of mRNA (20 mg total) using vehicle (bottom line), TransIT (middle line), 10 kDa aPACE actuated for 10 days (top line). Results are presented as mean±SD of N=3 animals (*$p<0.001$ and *$p<0.05$). FIG.
Figure 6C:
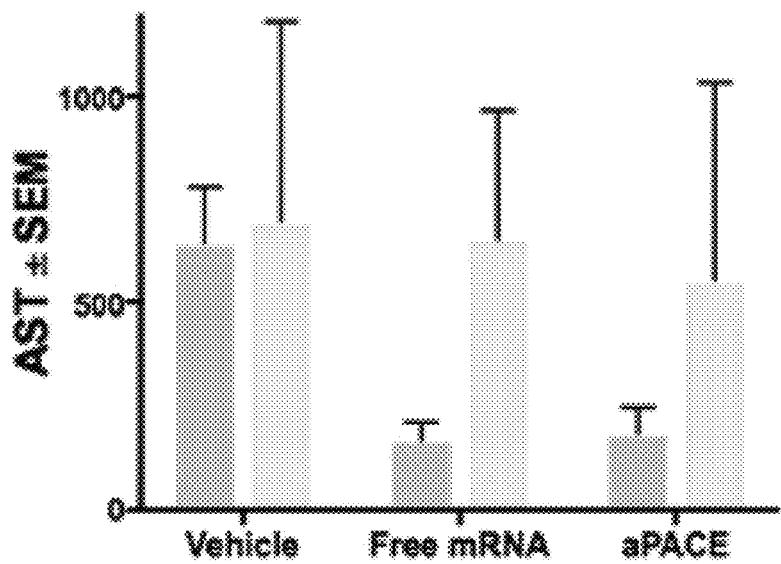
Figure 6D:
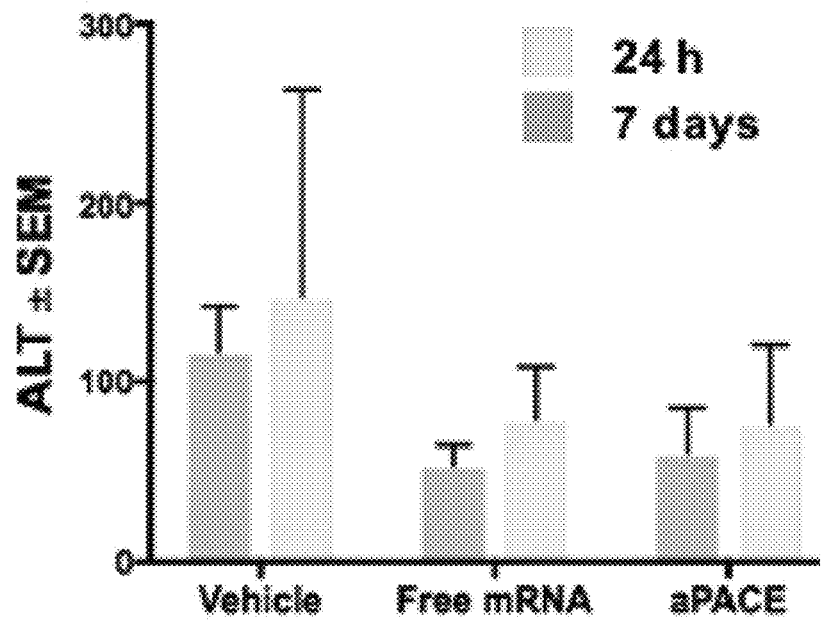
Figure 6E:
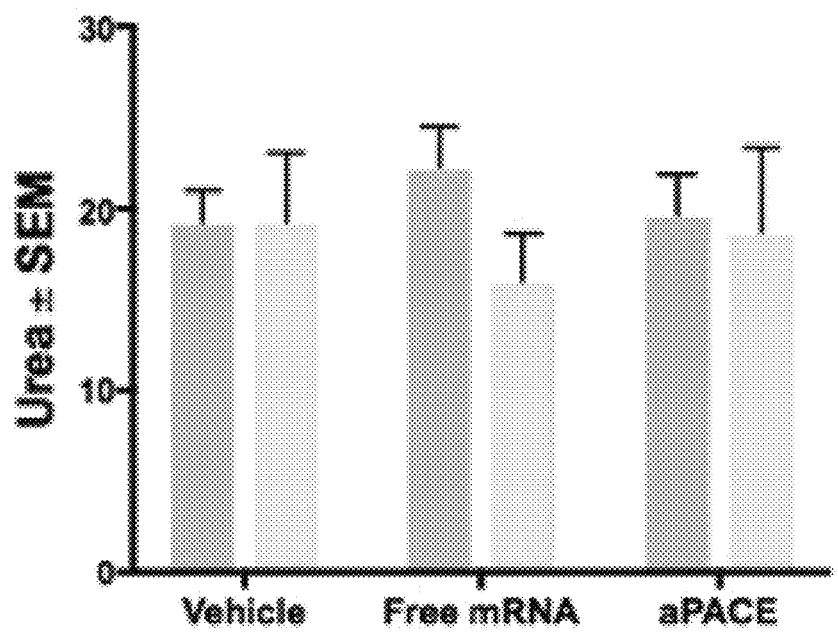
Figure 6F:
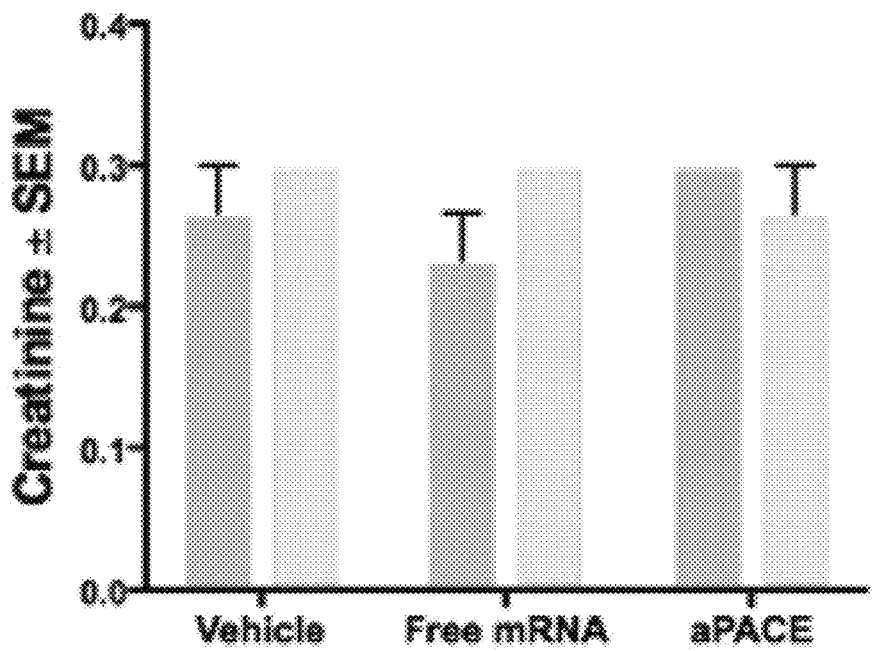

FIG. 6A is a bar graph showing the EPO blood concentration 6 h after IV administration of mRNA (20 mg total) using TransIT, 5 kDa non-actuated PACE, 5 kDa aPACE actuated for 5 days, 10 kDa non-actuated PACE, or 10 kDa aPACE actuated for 10 days. Results are presented as mean±SD of N=3 animals (**p<0.0001). FIG. 6B is a line graph showing a time course of EPO production following IV administration of mRNA (20 mg total) using vehicle (bottom line), TransIT (middle line), 10 kDa aPACE actuated for 10 days (top line). Results are presented as mean±SD of N=3 animals (*p<0.001 and *p<0.05). FIG. 6C-6F are bar graphs showing blood chemistry (AST (FIG. 6C), ALT (FIG. 6D), Urea (FIG. 6E), Creatinine (FIG. 6F)) analysis 24 h and 7 days after IV administration of acetate buffer, free mRNA or mRNA:aPACE polyplexes. Results are presented as mean±SEM of N=3 animals.

For both TransIT and the aPACE polyplexes, the EPO production peaked at 6 h post-injection. The injection of acetate buffer (vehicle) followed by repeated bleeding induced a slight increase in EPO blood levels over time, but the levels of EPO after administration of 10 kDa actuated PACE polyplexes were significantly higher compared to the levels obtained after administration of TransIT for up to 48 h (p<0.001 at 6 h and p<0.05 at 24 h and 48 h).

It has been hypothesized that the duration of EPO expression might be more important than the maximal EPO expression level to induce a physiological response, such as red blood cell production. EPO delivery using DNA has been explored and provided long-term EPO production, however lethal polycythemia due to uncontrolled production of the protein has been reported (Villeval et al., Blood 84 (3) 928e933 (1994), Johnston et al., Mol. Ther. 7 (4) 493e497 (2003)). Using the best aPACE polymer (10 kDa actuated for 10 days), significant EPO production was obtained for up to 48 h, which is significantly longer than the blood half-lifetime of free EPO (around 2 h). FIG. 5C is a line graph showing cytotoxicity profiles (Cell Viability (%)) of mRNA: aPACE polyplexes (5 kDa 5 D, 10 kDa 10 D, 20 kDa 30 D (cluster of top lines)) compared to the mRNA:TransIT complexes (bottom line). Blood chemistry and histology analysis demonstrated that aPACE did not induce systemic toxicity, 24 h or 7 days after administration.

These results demonstrate that the end group and MW of PACE affects its mRNA transfection efficiency more than predicted. Based on this observation, a unique polymeric structure was obtained by "top-down" actuation through the controlled hydrolysis of classic PACE terpolymers. The combination of MW and end groups in the actuated polymers enabled efficient mRNA complexation and transfection in vitro and in vivo, while the low cation density of PACE ensured a low toxicity profile. Actuation of the PACE terpolymer opens the way for mRNA-based treatments using a biodegradable delivery system that has been engineered to safely augment protein production.

Example 5: PACE End Groups Affect Messenger RNA Loading onto Polyplexes

Materials and Methods

Synthesis of End-Group Modified PACE Polymers and Polyplexes

A PACE backbone which is made from cationic diols, diethyl sebacate, and lactones has a mixture of hydroxyl and methyl end groups (Zhou, et al., Nature Materials, 11:82-90 (2012). [PMCID: PMC4180913).

To modify PACE with different end groups, the parent polymer was synthesized with sebacic acid instead of diethyl sebacate, which yields PACE with a mixture of hydroxyl and carboxyl end groups. Both of the two end groups were activated with carbodiimidazole (CDI) at a molar ratio of 1:40 by stirring in dry dichloromethane (DCM) overnight at room temperature. The mixture was washed three times with deionized water, followed by evaporation of DCM under vacuum to obtain the reactant, PACE-CDI: CDI activation (1, 2), followed by nucleophilic substitution with an amine-containing molecule (3,4), as illustrated below, and in Examples 1-4.

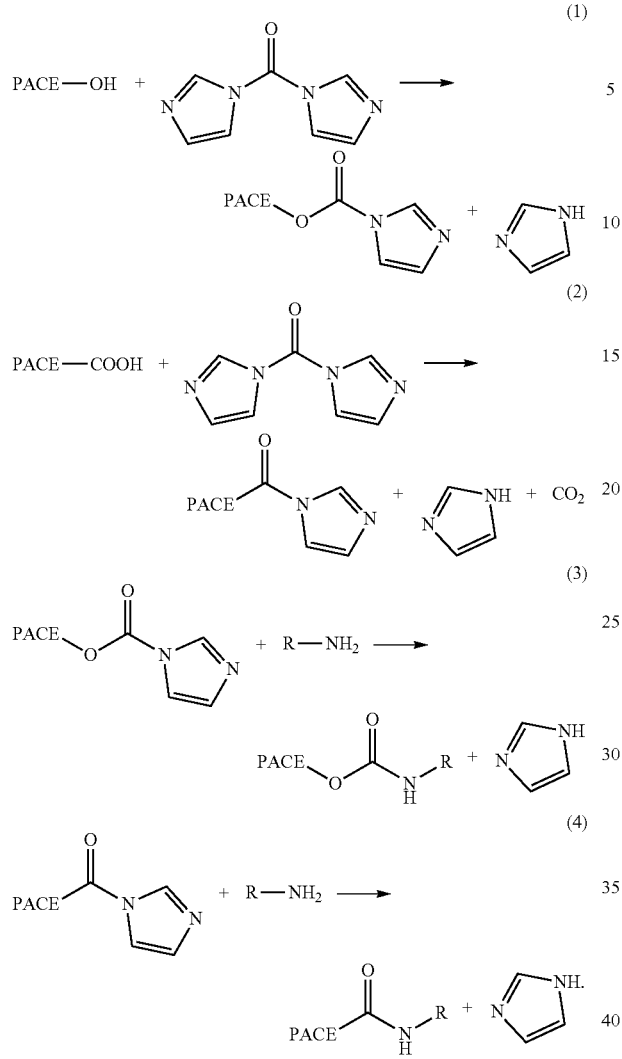

For conjugation, 5 mM of the amine-containing molecule was reacted with 0.5 mM of PACE-CDI in DMSO for 40 hours at room temperature under constant stirring. After reaction, the mixture was washed with 10-fold volume of deionized water, extracted with DCM, followed by evaporation of DCM under vacuum to obtain PACE with new end groups.

The chemical structure of the end groups are illustrated below:

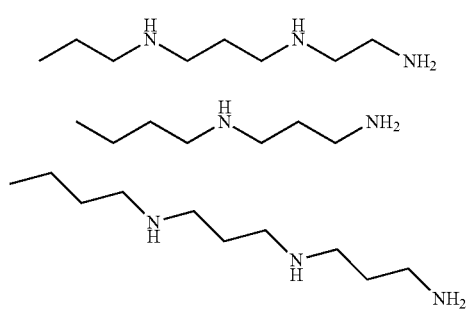

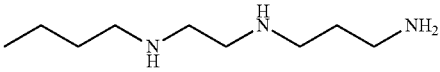
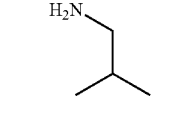
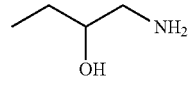
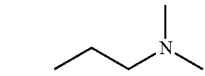
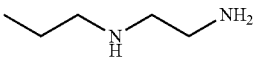
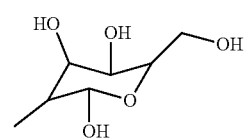
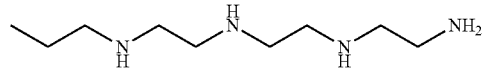
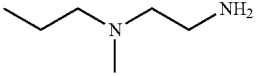
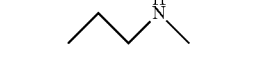
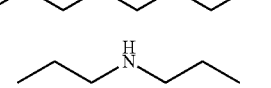
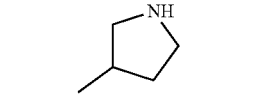
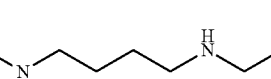
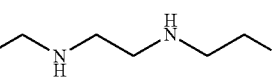
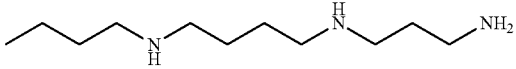
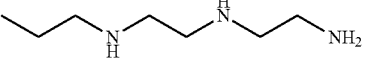

Ribogreen mRNA Loading Assay

Ribogreen is a small dye that emits fluorescence after binding with messenger RNA. After complexation with PACE, messenger RNA becomes inaccessible to the dye, and less fluorescence signal will be observed. mRNA, polyplex, and ribogreen were mixed, and fluorescence monitored.

Cy5 mRNA/Polyplex Uptake Assay ddRLuc-Fc protein and mRNA encoding FLuc were first coencapsulated by PACE polymers and then fed to Expi293F cells for 7 h in the presence of a proteasome inhibitor, Epoxomycin. Cells were then checked by a dual-luciferase assay to reveal RLuc activity (n=4). The data were normalized to TransIT (set to 1).

Cy5-labelled mRNA formed polyplexes with PACE with different end groups, which were fed to HEK293 cells. Cells were monitored for fluorescence.

Endosome Escape Assay

Endosome escape of polyplexes prepared with fLuc mRNA using PACE with different end groups were quantified with the ddRLuc system.

Results

The PACE end group affects messenger RNA loading onto polyplexes. The results of a ribogreen assay are illustrated in FIG. 7, and are very consistent with a corresponding gel retardation assay.

PACE end group affects cellular uptake of polyplexes. The results of a cellular uptake assay are illustrated in FIG. 8A-8D. FIG. 8A shows schematics of what is occurring to produce the results in FIGS. 8B, 8C and 8D, showing the efficiency of mRNA encapsulation, uptake and endosomal escape, and transfection efficiency. The efficiency of mRNA encapsulation was quantified by a Ribogreen assay (n=4). Polymers encapsulating Cy5-labeled mRNA were fed to Expi293F cells followed by FACS to quantify the uptake level (n=3) (FIG. 8B). Statistical differences were analyzed with an unpaired Student's t test between each polymer with mRNA groups; * denotes $p<0.05$,  denotes $p<0.01$, * denotes $p<0.001$, **** denotes $p<0.0001$, and n.s. denotes no significant difference.

PACE with different end groups demonstrated different abilities to be taken up by cells. PACE end group affects endosomal escape of mRNA. The results of an endosomal escape assay using fLuc mRNA and PACE with different end groups is illustrated in FIG. 8C.

PACE end group chemistry affects transfection efficiency of the polymeric delivery system. Transfection efficiencies of PACE were measured by fluc activity produced by HEK293 cells. The results are illustrated in FIG. 8D.

FIGS. 9A-9C, show the linear correlation of transfection efficiency (represented as fluc activity) and different steps of transfection, including mRNA loading (FIG. 9A), uptake (FIG. 9B), and endosome escape (FIG. 9C). As the biological step gets closer to protein production, the R2 values of the linear correlation gets higher, indicating better predicting power.

FIGS. 10A and 10B are plots (data from IVIS images) showing the biodistribution of the polyplexes measured by bioluminescence distribution 6 h after I.P. injection (FIG. 10A) and after I.V. injection (FIG. 10B) for, heart, lung, liver, kidney, spleen, intestine.

Unless defined otherwise, all technical and scientific terms used herein have the same meanings as commonly understood by one of skill in the art to which the invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

---

We claim:

1. A polymer of Formula I:

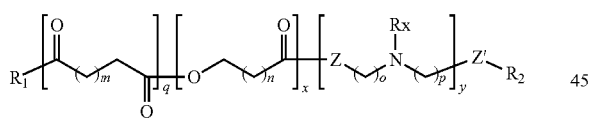

Formula I wherein n is an integer from 1-30, m, o, and p are independently integers from 1-20, x, y, and q are independently integers from 1-1000, Rx is hydrogen, substituted or unsubstituted alkyl, or substituted or unsubstituted aryl, or substituted or unsubstituted alkoxy, Z and Z' are independently O or NR', wherein R' is hydrogen, substituted or unsubstituted alkyl, or substituted or unsubstituted aryl, wherein $R_1$ and $R_2$ are chemical entities containing a hydroxyl group, a primary amine group, a secondary amine group, a tertiary amine group, or combinations thereof.

2. The polymer of claim 1, wherein R1 and/or R2 are not

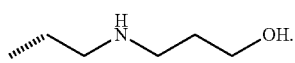

3. The polymer of claim 1, wherein polyplexes or particles formed from the polymer show improved loading, improved cellular transfection, improved intracellular endosomal release, or a combination thereof of a mRNA, relative to corresponding polyplexes or particles wherein R1 and/or R2 consist of

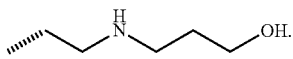

4. The polymer of claim 1, wherein the polymer has a structure of Formula II:

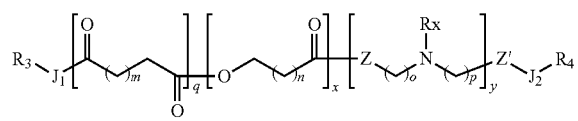

Formula II wherein $J_1$ and $J_2$ are independently linking moieties or absent, wherein at least one of $J_1$ and $J_2$ is present, $R_3$ and $R_4$ are substituted alkyl containing a hydroxyl group, a primary amine group, a secondary amine group, a tertiary amine group, or combinations thereof.

5. The polymer of claim 4, wherein the polymer has a structure of Formula III:

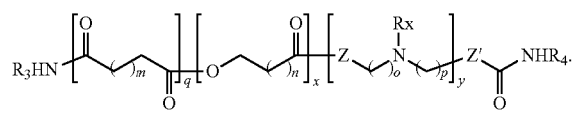

6. The polymer of claim 4, wherein $R_3$ is the same as R4.

7. The polymer of claim 4, wherein R3 and/or R4 are independently selected from the group consisting of

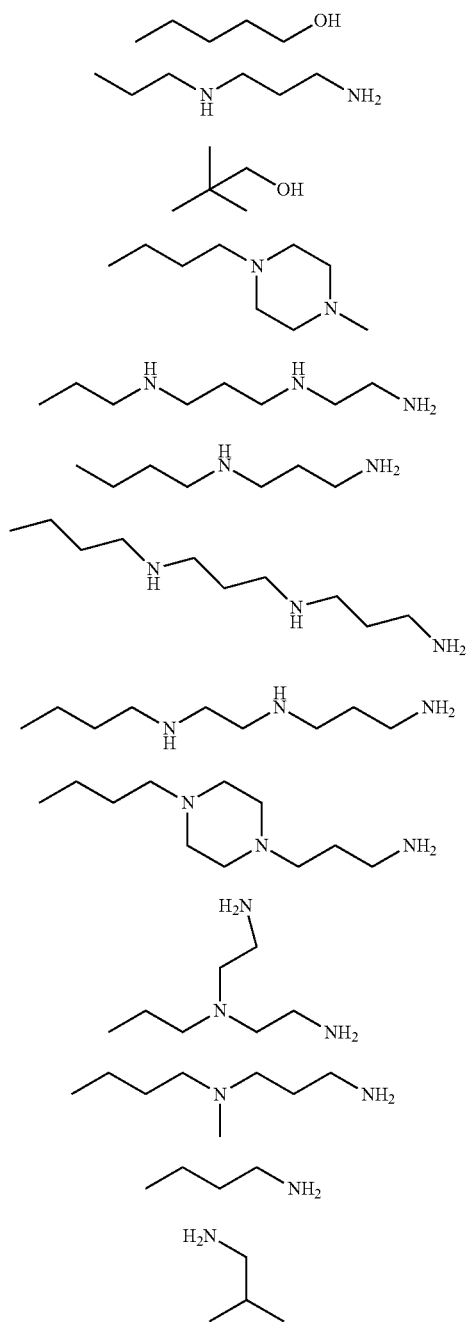

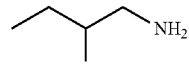
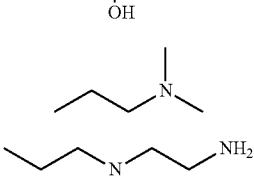
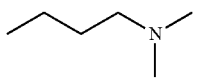
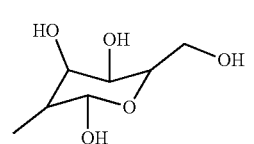
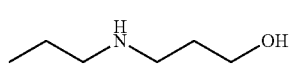
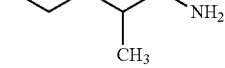
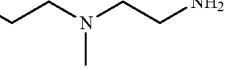
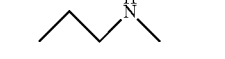
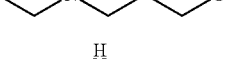
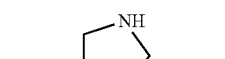
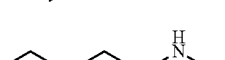
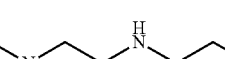
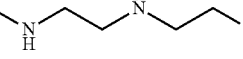
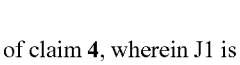

8. The polymer of claim 4, wherein J1 is —O— or —NH, $J_2$ is —C(O)NH— or —C(O)O— or a combination thereof.

9. The polymer of claim 4, wherein $R_3$, $R_4$, or both contain a primary amine group, and optionally one or more secondary or tertiary amine groups.

10. The polymer of claim 4, wherein $R_3$, $R_4$, or both contain a hydroxyl group, and optionally one or more amine groups.

11. The polymer of claim 4, wherein R₃, R₄, or both contain a hydroxyl group and no amine group.

12. The polymer of claim 4, wherein at least one of R₃ and R₄ does not contain a hydroxyl group.

13. The polymer of claim 4, wherein R₃, R₄, or both are -unsubstituted C₁-C₁₀ alkylene-Aq-unsubstituted C₁-C₁₀ alkylene-Bq, -unsubstituted C₁-C₁₀ alkylene-Aq-substituted C₁-C₁₀ alkylene-Bq, -substituted C₁-C₁₀ alkylene-Aq-unsubstituted C₁-C₁₀ alkylene-Bq, or -substituted C₁-C₁₀ alkylene-Aq-substituted C₁-C₁₀ alkylene-Bq, wherein Aq is absent or —NR₅—, and Bq is hydroxyl, primary amine, secondary amine, or tertiary amine, wherein R₅ is hydrogen, substituted or unsubstituted alkyl, or substituted or unsubstituted aryl.

14. The polymer of claim 1, wherein Z is the same as Z'.

15. The polymer of claim 1, wherein n is 4, 10, 13, or 14.

16. The polymer of claim 1, wherein m is 5, 6, or 7.

17. The polymer of claim 1, wherein Rₓ is substituted or unsubstituted alkyl.

18. The polymer of claim 1, wherein the weight average molecular weight, as measured by gel permeation chromatography using narrow polydispersity polystyrene standards, is between about 2,000 Daltons and 20,000 Daltons.

19. A polyplex or solid-core particle comprising the polymer of claim 1, and one or more therapeutic, prophylactic, or diagnostic nucleic acid agents.

20. The polyplex or particle of claim 19, wherein the nucleic acid agent is RNA or DNA.

21. The polyplex or particle of claim 20 wherein the nucleic acid agent comprises a coding sequence that encodes a protein.

22. The polyplex or particle of claim 21 wherein the coding sequence is operably linked to an expression control sequence.

23. The polyplex or particle of claim 20 wherein the nucleic acid agent is a functional nucleic acid, or an expression vector comprising sequence encoding a functional nucleic acid operably linked to an expression control sequence.

24. The polyplex or particle of claim 19 wherein the nucleic acid agent is selected from the group consisting of antisense molecules, siRNA, miRNA, aptamers, ribozymes, triplex forming molecules, RNAi, and external guide sequences.

25. A polymer of Formula I:

Formula I

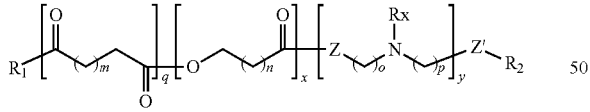

wherein n is an integer from 1-30, m, o, and p are independently integers from 1-20, x, y, and q are independently integers from 1-1000, Rx is hydrogen, substituted or unsubstituted alkyl, or substituted or unsubstituted aryl, or substituted or unsubstituted alkoxy, Z and Z' are independently O or NR', wherein R' is hydrogen, substituted or unsubstituted alkyl, or substituted or unsubstituted aryl, wherein R₁ and R₂ are chemical entities containing a hydroxyl group, a primary amine group, a secondary amine group, a tertiary amine group, or combinations thereof, having a weight average molecular weight, as measured by gel permeation chromatography using narrow polydispersity polystyrene standards, between about 2,000 Daltons and 20,000 Daltons, and at least one terminus of the polymer contains a hydroxyl or carboxyl end group.

26. The polymer of claim 25 complexed with a therapeutic, prophylactic or diagnostic agent.

27. A polymer having a structure of Formula II:

Formula II

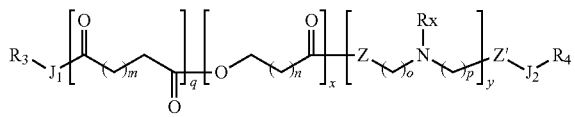

wherein:
J₁ and J₂ are independently linking moieties or absent, and
R3 and/or R4 are independently selected from the group consisting of

21

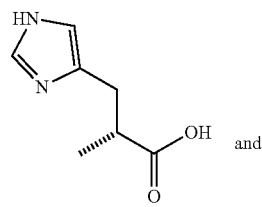 and

22

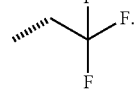.

* * * * *

SEQUENCE LISTING

```
<160> NUMBER OF SEQ ID NOS: 7

<210> SEQ ID NO 1
<211> LENGTH: 26
<212> TYPE: PRT
<213> ORGANISM: Artificial Sequence
<220> FEATURE:
<223> OTHER INFORMATION: synthetic polypeptide

<400> SEQUENCE: 1

Glu Glu Glu Glu Glu Glu Glu Glu Glu Glu Glu Glu Glu Glu Glu Glu
1               5                   10                  15

Gly Gly Gly Gly Gly Gly Arg Gly Asp Lys
            20                  25

<210> SEQ ID NO 2
<211> LENGTH: 26
<212> TYPE: PRT
<213> ORGANISM: Artificial Sequence
<220> FEATURE:
<223> OTHER INFORMATION: synthetic polypeptide

<400> SEQUENCE: 2

Arg Gly Asp Lys Gly Gly Gly Gly Gly Gly Glu Glu Glu Glu Glu Glu
1               5                   10                  15

Glu Glu Glu Glu Glu Glu Glu Glu Glu Glu
            20                  25

<210> SEQ ID NO 3
<211> LENGTH: 22
```

```
<212> TYPE: PRT
<213> ORGANISM: Artificial Sequence
<220> FEATURE:
<223> OTHER INFORMATION: synthetic polypeptide

<400> SEQUENCE: 3

Gly Gly Gly Gly Gly Gly Glu Glu Glu Glu Glu Glu Glu Glu Glu
1               5                   10                  15

Glu Glu Glu Glu Glu Glu
            20

<210> SEQ ID NO 4
<211> LENGTH: 29
<212> TYPE: PRT
<213> ORGANISM: Artificial Sequence
<220> FEATURE:
<223> OTHER INFORMATION: synthetic polypeptide
<220> FEATURE:
<221> NAME/KEY: misc_feature
<222> LOCATION: (2)..(2)
<223> OTHER INFORMATION: D-amino acid
<220> FEATURE:
<221> NAME/KEY: misc_feature
<222> LOCATION: (3)..(3)
<223> OTHER INFORMATION: D-amino acid
<220> FEATURE:
<221> NAME/KEY: misc_feature
<222> LOCATION: (5)..(5)
<223> OTHER INFORMATION: D-amino acid
<220> FEATURE:
<221> NAME/KEY: misc_feature
<222> LOCATION: (6)..(6)
<223> OTHER INFORMATION: D-amino acid
<220> FEATURE:
<221> NAME/KEY: misc_feature
<222> LOCATION: (29)..(29)
<223> OTHER INFORMATION: CONH2 modification

<400> SEQUENCE: 4

Gly Pro Leu Gly Val Arg Gly Gly Gly Gly Gly Gly Glu Glu Glu
1               5                   10                  15

Glu Glu Glu Glu Glu Glu Glu Glu Glu Glu Glu Glu Glu
            20                  25

<210> SEQ ID NO 5
<211> LENGTH: 7
<212> TYPE: PRT
<213> ORGANISM: Artificial Sequence
<220> FEATURE:
<223> OTHER INFORMATION: synthetic polypeptide
<220> FEATURE:
<221> NAME/KEY: misc_feature
<222> LOCATION: (2)..(2)
<223> OTHER INFORMATION: D-amino acid
<220> FEATURE:
<221> NAME/KEY: misc_feature
<222> LOCATION: (3)..(3)
<223> OTHER INFORMATION: D-amino acid
<220> FEATURE:
<221> NAME/KEY: misc_feature
<222> LOCATION: (5)..(5)
<223> OTHER INFORMATION: D-amino acid
<220> FEATURE:
<221> NAME/KEY: misc_feature
<222> LOCATION: (6)..(6)
<223> OTHER INFORMATION: D-amino acid

<400> SEQUENCE: 5

Gly Pro Leu Gly Val Arg Gly
1               5
```

```
<210> SEQ ID NO 6
<211> LENGTH: 5
<212> TYPE: PRT
<213> ORGANISM: Artificial Sequence
<220> FEATURE:
<223> OTHER INFORMATION: synthetic polypeptide

<400> SEQUENCE: 6

Ala Ser Gly Pro Arg
1               5

<210> SEQ ID NO 7
<211> LENGTH: 4
<212> TYPE: PRT
<213> ORGANISM: Artificial Sequence
<220> FEATURE:
<223> OTHER INFORMATION: synthetic polypeptide
<220> FEATURE:
<221> NAME/KEY: misc_feature
<222> LOCATION: (1)..(1)
<223> OTHER INFORMATION: X = R or K
<220> FEATURE:
<221> NAME/KEY: misc_feature
<222> LOCATION: (2)..(2)
<223> OTHER INFORMATION: X = any amino acid
<220> FEATURE:
<221> NAME/KEY: misc_feature
<222> LOCATION: (3)..(3)
<223> OTHER INFORMATION: X = any amino acid
<220> FEATURE:
<221> NAME/KEY: misc_feature
<222> LOCATION: (4)..(4)
<223> OTHER INFORMATION: X = R or K

<400> SEQUENCE: 7

Xaa Xaa Xaa Xaa
1
```